(12) United States Patent
Reich et al.

(10) Patent No.: US 11,826,559 B2
(45) Date of Patent: Nov. 28, 2023

(54) CARDIAC OUTPUT CONTROL APPARATUS AND METHOD OF USE THEREOF

(71) Applicants: Alton Reich, Huntsville, AL (US); Michael Roth, Scottsdale, AZ (US)

(72) Inventors: Alton Reich, Huntsville, AL (US); Michael Roth, Scottsdale, AZ (US)

( * ) Notice: Subject to any disclaimer, the term of this patent is extended or adjusted under 35 U.S.C. 154(b) by 86 days.

(21) Appl. No.: 17/071,665

(22) Filed: Oct. 15, 2020

(65) Prior Publication Data

US 2021/0146117 A1 May 20, 2021

Related U.S. Application Data

(63) Continuation-in-part of application No. 16/533,778, filed on Aug. 6, 2019, which is a continuation-in-part
(Continued)

(51) Int. Cl.
*A61M 60/523* (2021.01)
*A61B 5/029* (2006.01)
(Continued)

(52) U.S. Cl.
CPC ......... *A61M 60/523* (2021.01); *A61B 5/0205* (2013.01); *A61B 5/029* (2013.01); *A61B 5/1118* (2013.01); *A61B 5/1123* (2013.01); *A61B 5/14551* (2013.01); *A61B 5/318* (2021.01); *A61B 5/4839* (2013.01); *A61M 60/515* (2021.01); *A61M 60/531* (2021.01); *A61M 60/585* (2021.01); *G06N 7/01* (2023.01); *G16H 40/63* (2018.01); *G16H 50/20* (2018.01); *A61B 5/022* (2013.01); *A61B 2562/0219* (2013.01); *A61B 2562/0223* (2013.01); *A61M 2205/0283* (2013.01); *A61M 2205/3317* (2013.01); *A61M 2205/3327* (2013.01); *A61M 2205/50* (2013.01);
(Continued)

(58) Field of Classification Search
None
See application file for complete search history.

(56) References Cited

U.S. PATENT DOCUMENTS

2015/0174307 A1* 6/2015 Eckman ............. A61M 60/196
600/17

* cited by examiner

*Primary Examiner* — Erica S Lee
*Assistant Examiner* — Elizabeth K So
(74) *Attorney, Agent, or Firm* — Kevin H. Hazen; Hazen Patent Group, LLC

(57) ABSTRACT

The invention comprises an apparatus and a method for operating a cardiac assist pump, comprising the steps of: (1) providing a cardiac monitor comprising: a cardiac output sensor including an activity sensor and at least two of: a pulse oximeter; an electrocardiogram meter; and a blood pressure monitor; (2) receiving time-varying cardiovascular input data, from the cardiac output sensor, related to a transient hemodynamic state of a cardiovascular system; (3) receiving and operating on time-varying activity input data, from the activity sensor, to generate cardiovascular state information; (4) sensing activity with the activity sensor to generate a target cardiovascular state; (5) repeating both the steps of receiving and operating to update the transient cardiovascular state information and the step of sensing to update the target cardiovascular state; and (6) directing the cardiac assist pump to adjust assisted blood flow, yielding the updated transient cardiovascular state, toward the target cardiovascular state.

18 Claims, 29 Drawing Sheets

Related U.S. Application Data of application No. 15/251,779, filed on Aug. 30, 2016, now Pat. No. 10,460,843, which is a continuation-in-part of application No. 13/181,140, filed on Jul. 12, 2011, now Pat. No. 9,451,886, which is a continuation-in-part of application No. 13/181,027, filed on Jul. 12, 2011, now Pat. No. 8,494,829, which is a continuation-in-part of application No. 12/796,512, filed on Jun. 8, 2010, now Pat. No. 9,060,722, which is a continuation-in-part of application No. 12/640,278, filed on Dec. 17, 2009, now abandoned, application No. 17/071,665 is a continuation-in-part of application No. 14/078,254, filed on Nov. 12, 2013, now abandoned.

(60) Provisional application No. 61/727,586, filed on Nov. 16, 2012, provisional application No. 61/373,809, filed on Aug. 14, 2010, provisional application No. 61/372,190, filed on Aug. 10, 2010, provisional application No. 61/366,437, filed on Jul. 21, 2010, provisional application No. 61/171,802, filed on Apr. 22, 2009.

(51) Int. Cl.
| | |
|---|---|
| *A61B 5/11* | (2006.01) |
| *A61B 5/1455* | (2006.01) |
| *A61B 5/318* | (2021.01) |
| *A61B 5/00* | (2006.01) |
| *A61M 60/531* | (2021.01) |
| *A61M 60/585* | (2021.01) |
| *A61M 60/515* | (2021.01) |
| *G16H 50/20* | (2018.01) |
| *G16H 40/63* | (2018.01) |
| *A61B 5/0205* | (2006.01) |
| *G06N 7/01* | (2023.01) |
| *A61B 5/022* | (2006.01) |

(52) U.S. Cl.
CPC ..... *A61M 2230/04* (2013.01); *A61M 2230/06* (2013.01); *A61M 2230/20* (2013.01); *A61M 2230/63* (2013.01)

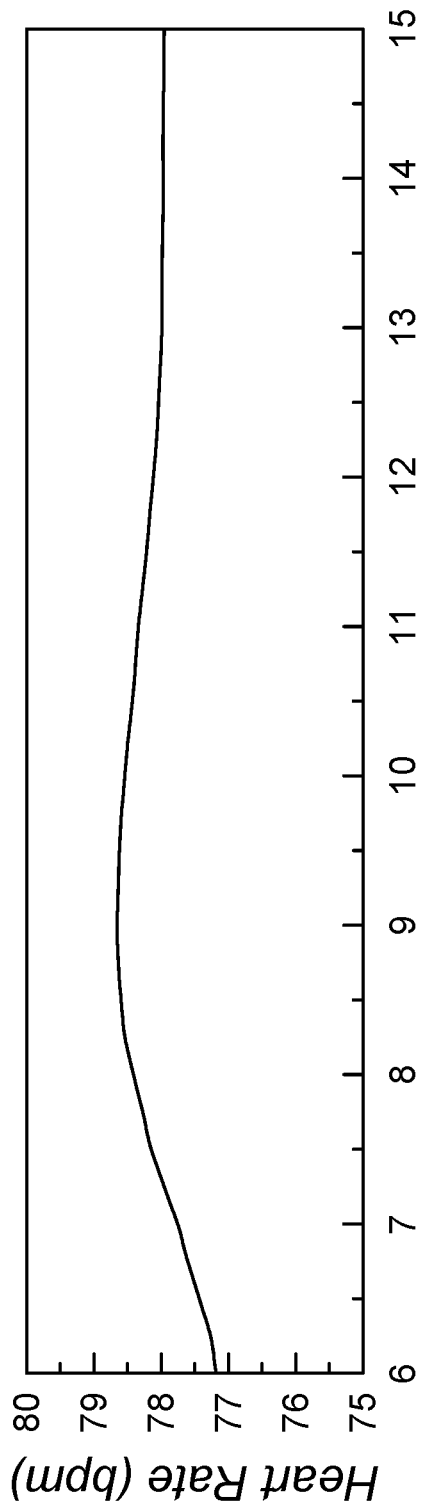
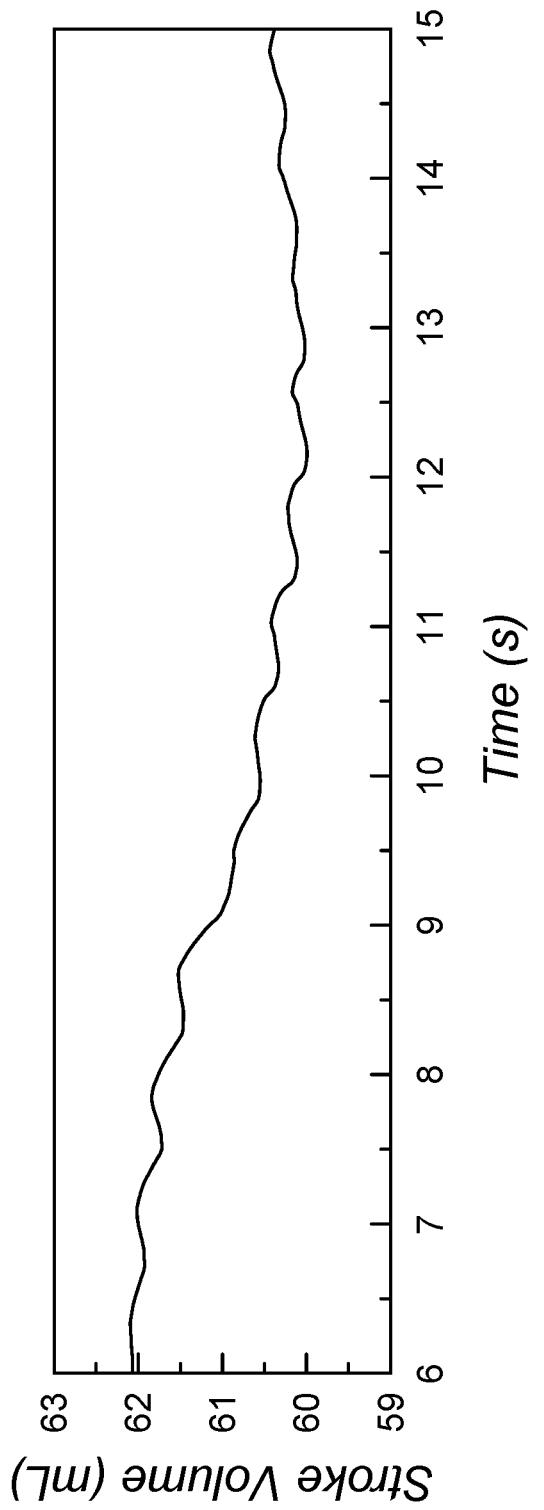
FIG. 9B
FIG. 9C

CARDIAC OUTPUT CONTROL APPARATUS AND METHOD OF USE THEREOF

CROSS-REFERENCES TO RELATED APPLICATIONS

This application is:

a continuation-in-part of U.S. patent application Ser. No. 16/533,778 filed Aug. 6, 2019 (now U.S. Pat. No. 10,751,555), which is a continuation-in-part of U.S. patent application Ser. No. 15/251,779 filed Aug. 30, 2016 (now U.S. patent no. 10,460,843) which is a continuation-in-part of U.S. patent application Ser. No. 13/181,140 filed Jul. 12, 2011 (now U.S. patent application publication no. US201200022336 A1), which is a continuation-in-part of U.S. patent application Ser. No. 13/181,027, filed Jul. 12, 2011 (now U.S. Pat. No. 8,494,829), which:

is a continuation-in-part of U.S. patent application Ser. No. 12/796,512, filed Jun. 8, 2010 (now U.S. Pat. No. 9,060,722), which is a continuation-in-part of U.S. patent application Ser. No. 12/640,278, filed Dec. 17, 2009 (U.S. patent application publication no. US201000274102A1), which claims benefit of U.S. provisional patent application No. 61/171,802, filed Apr. 22, 2009;

is a continuation-in-part of U.S. patent application Ser. No. 14/078,254 filed Nov. 12, 2013 (U.S. patent application publication no. US20150133721A1), which claims the benefit of U.S. provisional patent application No. 61/727,586;

claims benefit of U.S. provisional patent application No. 61/366,437 filed Jul. 21, 2010;

claims benefit of U.S. provisional patent application No. 61/372,190 filed Aug. 10, 2010; and claims benefit of U.S. provisional patent application No. 61/373,809 filed Aug. 14, 2010; and is a continuation-in-part of U.S. patent application Ser. No. 14/078,254 filed Nov. 12, 2013 (U.S. patent application publication no. US20150133721A1, now abandoned), which claims the benefit of U.S. provisional patent application No. 61/727,586, filed Nov. 16, 2012, all of which are incorporated herein in their entirety by this reference thereto.

STATEMENT REGARDING FEDERALLY SPONSORED RESEARCH OR DEVELOPMENT

The U.S. Government may have certain rights to this invention pursuant to Contract Number IIP-0839734 awarded by the National Science Foundation.

BACKGROUND OF THE INVENTION

Field of the Invention

The present invention relates generally to apparatus and methods for processing and/or representing sensor data, such as mechanical or medical sensor data, and applying the processed data to an artificial heart, electroactive polymer assist device, and/or a dosing pump.

Discussion of the Related Art

Mechanical devices and biomedical monitoring devices such as pulse oximeters, glucose sensors, electrocardiograms, capnometers, fetal monitors, electromyograms, electroencephalograms, and ultrasounds are sensitive to noise and artifacts. Typical sources of noise and artifacts include baseline wander, electrode-motion artifacts, physiological artifacts, high-frequency noise, and external interference. Some artifacts can resemble real processes, such as ectopic beats, and cannot be removed reliably by simple filters; however, these are removable by the techniques taught herein. In addition, mechanical devices and biomedical monitoring devices address a limited number of parameters. It would be desirable to expand the number of parameters measured, such as to additional biomedical state parameters.

Patents related to the current invention are summarized herein.

Mechanical Systems

Several reports of diagnostics and prognostics applied to mechanical systems have been reported.

Vibrational Analysis

R. Klein "Method and System for Diagnostics and Prognostics of a Mechanical System", U.S. Pat. No. 7,027,953 B2 (Apr. 11, 2006) describes a vibrational analysis system for diagnosis of health of a mechanical system by reference to vibration signature data from multiple domains, which aggregates several features applicable to a desired fault for trend analysis of the health of the mechanical system.

Intelligent System

S. Patel, et. al. "Process and System for Developing Predictive Diagnostic Algorithms in a Machine", U.S. Pat. No. 6,405,108 B1 (Jun. 11, 2002) describe a process for developing an algorithm for predicting failures in a system, such as a locomotive, comprising conducting a failure mode analysis to identify a subsystem, collecting expert data on the subsystem, and generating a predicting signal for identifying failure modes, where the system uses external variables that affect the predictive accuracy of the system.

C. Bjornson, "Apparatus and Method for Monitoring and Maintaining Plant Equipment", U.S. Pat. No. 6,505,145 B1 (Jan. 11, 2003) describes a computer system that implements a process for gathering, synthesizing, and analyzing data related to a pump and/or a seal, in which data are gathered, the data is synthesized and analyzed, a root cause is determined, and the system suggests a corrective action.

C. Bjornson, "Apparatus and Method for Monitoring and Maintaining Plant Equipment", U.S. Pat. No. 6,728,660 B2 (Apr. 27, 2004) describes a computer system that implements a process for gathering, synthesizing, and analyzing data related to a pump and/or a seal, in which data are gathered, the data is synthesized and analyzed, and a root cause is determined to allow a non-specialist to properly identify and diagnose a failure associated with a mechanical seal and pump.

K. Pattipatti, et. al. "Intelligent Model-Based Diagnostics for System Monitoring, Diagnosis and Maintenance", U.S. Pat. No. 7,536,277 B2 (May 19, 2009) and K. Pattipatti, et. al. "Intelligent Model-Based Diagnostics for System Monitoring, Diagnosis and Maintenance", U.S. Pat. No. 7,260,501 B2 (Aug. 21, 2007) both describe systems and methods for monitoring, diagnosing, and for condition-based maintenance of a mechanical system, where model-based diagnostic methodologies combine or integrate analytical models and graph-based dependency models to enhance diagnostic performance.

Inferred Data

R. Tryon, et. al. "Method and Apparatus for Predicting Failure in a System", U.S. Pat. No. 7,006,947 B2 (Feb. 28, 2006) describe a method and apparatus for predicting system failure or reliability using a computer implemented model relying on probabilistic analysis, where the model uses data obtained from references and data inferred from acquired data. More specifically, the method and apparatus uses a pre-selected probabilistic model operating on a specific load to the system while the system is under operation.

Virtual Prototyping

R. Tryon, et. al. "Method and Apparatus for Predicting Failure of a Component", U.S. Pat. No. 7,016,825 B1 (Mar. 21, 2006) describe a method and apparatus for predicting component failure using a probabilistic model of a material's microstructural-based response to fatigue using virtual prototyping, where the virtual prototyping simulates grain size, grain orientation, and micro-applied stress in fatigue of the component.

R. Tryon, et. al. "Method and Apparatus for Predicting Failure of a Component, and for Determining a Grain Orientation Factor for a Material", U.S. Pat. No. 7,480,601 B2 (Jan. 20, 2009) describe a method and apparatus for predicting component failure using a probabilistic model of a material's microstructural-based response to fatigue using a computer simulation of multiple incarnations of real material behavior or virtual prototyping.

Medical Systems

Several reports of systems applied to biomedical systems have been reported.

Lung Volume

M. Sackner, et. al. "Systems and Methods for Respiratory Event Detection", U.S. patent application no. 2008/0082018 A1 (Apr. 3, 2008) describe a system and method of processing respiratory signals from inductive plethysmographic sensors in an ambulatory setting that filters for artifact rejection to improve calibration of sensor data and to produce output indicative of lung volume.

Pulse Oximeter

J. Scharf, et. al. "Separating Motion from Cardiac Signals Using Second Order Derivative of the Photo-Plethysmograph and Fast Fourier Transforms", U.S. Pat. No. 7,020,507 B2 (Mar. 28, 2006) describes the use of filtering photo-plethysmograph data in the time domain to remove motion artifacts.

M. Diab, et. al. "Plethysmograph Pulse Recognition Processor", U.S. Pat. No. 6,463,311 B1 (Oct. 8, 2002) describe an intelligent, rule-based processor for recognition of individual pulses in a pulse oximeter-derived photo-plethysmograph waveform operating using a first phase to detect candidate pulses and a second phase applying a plethysmograph model to the candidate pulses resulting in period and signal strength of each pulse along with pulse density.

C. Baker, et. al. "Method and Apparatus for Estimating Physiological Parameters Using Model-Based Adaptive Filtering", U.S. Pat. No. 5,853,364 (Dec. 29, 1998) describe a method and apparatus for processing pulse oximeter data taking into account physical limitations using mathematical models to estimate physiological parameters.

Cardiac

J. McNames, et. al. "Method, System, and Apparatus for Cardiovascular Signal Analysis, Modeling, and Monitoring", U.S. patent application publication no. 2009/0069647 A1 (Mar. 12, 2009) describe a method and apparatus to monitor arterial blood pressure, pulse oximetry, and intracranial pressure to yield heart rate, respiratory rate, and pulse pressure variation using a statistical state-space model of cardiovascular signals and a generalized Kalman filter to simultaneously estimate and track the cardiovascular parameters of interest.

M. Sackner, et. al. "Method and System for Extracting Cardiac Parameters from Plethysmograph Signals", U.S. patent application publication no. 2008/0027341 A1 (Jan. 31, 2008) describe a method and system for extracting cardiac parameters from ambulatory plethysmographic signal to determine ventricular wall motion.

Hemorrhage

P. Cox, et. al. "Methods and Systems for Non-Invasive Internal Hemorrhage Detection", International Publication no. WO 2008/055173 A2 (May 8, 2008) describe a method and system for detecting internal hemorrhaging using a probabilistic network operating on data from an electrocardiogram, a photoplethysmogram, and oxygen, respiratory, skin temperature, and blood pressure measurements to determine if the person has internal hemorrhaging.

Disease Detection

V. Karlov, et. al. "Diagnosing Inapparent Diseases From Common Clinical Tests Using Bayesian Analysis", U.S. patent application publication no. 2009/0024332 A1 (Jan. 22, 2009) describe a system and method of diagnosing or screening for diseases using a Bayesian probability estimation technique on a database of clinical data.

Anti-Embolism Stocking

C. Brown III, "Anti-Embolism Stocking Device", U.S. Pat. No. 6,123,681 (Sep. 26, 2000) describes an anti-embolism stocking made from a polymer that constricts in response to a stimulus.

Statement of the Problem

Mechanical and biomedical sensors are typically influenced by multiple sources of contaminating signals that often overlap the frequency of the signal of interest, making it difficult, if not impossible, to apply conventional filtering. Severe artifacts such as occasional signal dropouts due to sensor movement or large periodic artifacts are also difficult to filter in real time. Biological sensor hardware can be equipped with a computer comprising software for post-processing data and reducing or rejecting noise and artifacts. Current filtering techniques typically use some knowledge of the expected frequencies of interest where the sought-after physiological information should be found.

Adaptive filtering has been used to attenuate artifacts in pulse oximeter signals corrupted with overlapping frequency noise bands by estimating the magnitude of noise caused by patient motion and other artifacts and canceling its contribution from pulse oximeter signals during patient movement. Such a time correlation method relies on a series of assumptions and approximations to the expected signal, noise, and artifact spectra, which compromises accuracy, reliability, and general applicability.

Filtering techniques based on Kalman and extended Kalman techniques offer advantages over conventional methods and work well for filtering linear systems or systems with small nonlinearities and Gaussian noise. These filters, however, are not adequate for filtering highly nonlinear systems and non-Gaussian/non-stationary noise. Therefore, obtaining reliable biomedical signals continue to present problems, particularly when measurements are made in mobile, ambulatory, and physically active patients.

Existing data processing techniques, including adaptive noise cancellation filters, are unable to extract information that is hidden or embedded in biomedical signals and also discard some potentially valuable information.

Existing medical sensors sense a narrow spectrum of medical parameters and states. What is needed is a system readily expanding the number of biomedical states determined and application of the determined biomedical state(s) to a cardiac assist pump and/or a dosing pump.

A method or apparatus for extracting additional useful information from a mechanical sensor in a mechanical system, a biomedical system, and/or a system component or sub-component is needed to provide users additional and/or clearer information.

SUMMARY OF THE INVENTION

The invention comprises use of fused data to extract, filter, estimate and/or add additional information about a system based on data from a sensor and use a determined state of the system as a control, such as a control of a cardiac assist pump and/or a dosing pump.

DESCRIPTION OF THE FIGURES

A more complete understanding of the present invention is derived by referring to the detailed description and claims when considered in connection with the Figures, wherein like reference numbers refer to similar items throughout the figures.

FIG. 9B illustrates processed output data of heart rate; FIG. 9C illustrates processed stroke volume.

DETAILED DESCRIPTION OF THE INVENTION

Figure 1:
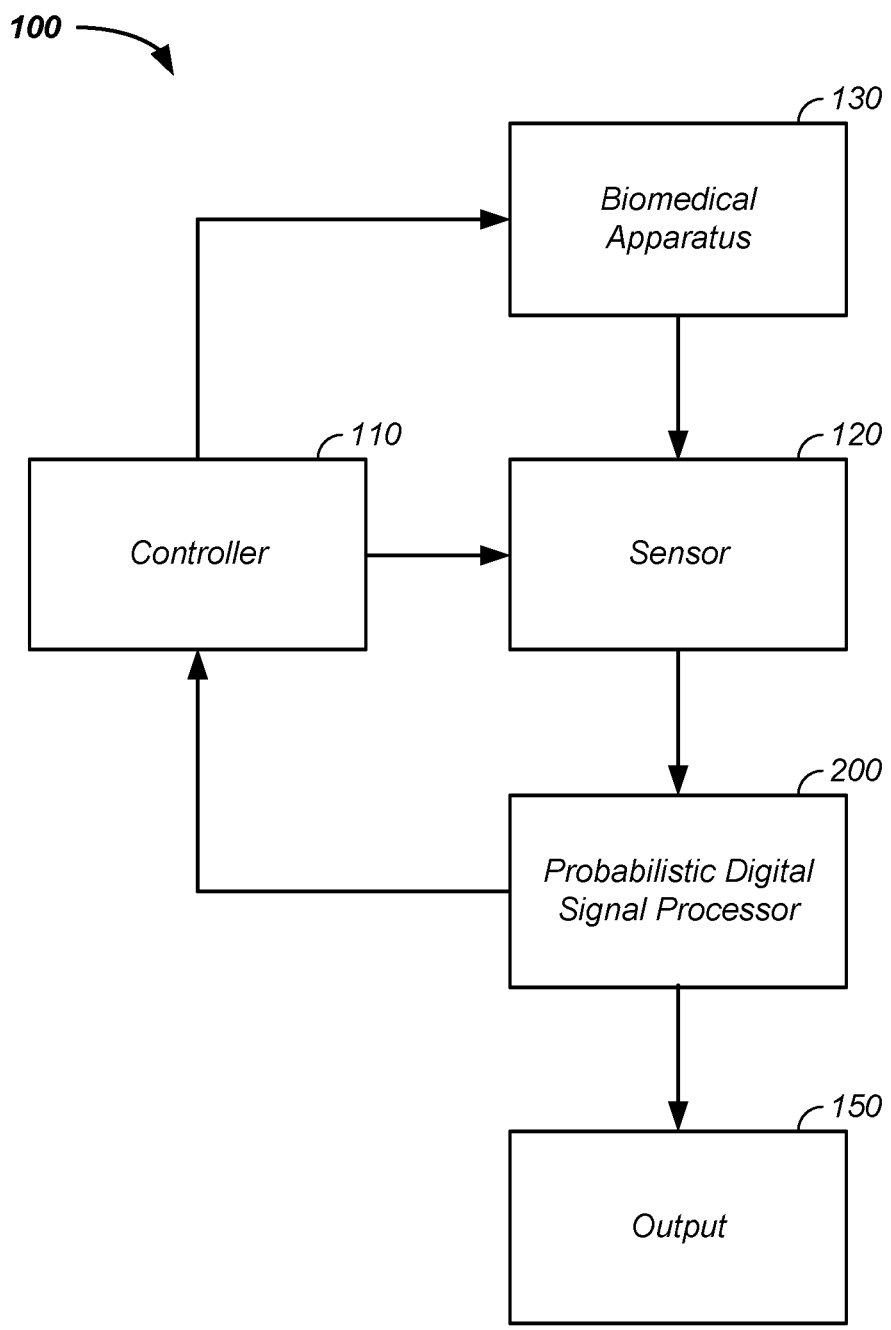
FIG. 1 illustrates operation of the intelligent data extraction algorithm on a biomedical apparatus.

The invention comprises an apparatus and a method for operating a cardiac assist pump, comprising the steps of: (1) providing a cardiac monitor comprising: a cardiac output sensor including an activity sensor and at least two of: a pulse oximeter; an electrocardiogram meter; and a blood pressure monitor; (2) receiving time-varying cardiovascular input data, from the cardiac output sensor, related to a transient hemodynamic state of a cardiovascular system; (3) receiving and operating on time-varying activity input data, from the activity sensor, to generate transient cardiovascular state information, comprising at least one of: a current left ventricle stroke volume; a current blood pressure; and a current blood flow rate; (4) sensing activity with the activity sensor to generate a target cardiovascular state; (5) repeating both the steps of receiving and operating to update the transient cardiovascular state information and the step of sensing to update the target cardiovascular state; and (6) directing the cardiac assist pump to adjust assisted blood flow, yielding the updated transient cardiovascular state, toward the target cardiovascular state.

The system applies to the mechanical and medical fields. Herein, for clarity the system is applied to biomedical devices, though the system concepts apply to mechanical apparatus.

In one embodiment, an intelligent data extraction algorithm (IDEA) is used in a system, which combines a dynamic state-space model with a probabilistic digital signal processor to estimate a parameter, such as a biomedical parameter. Initial probability distribution functions are input to a dynamic state-space model, which iteratively operates on probability distribution functions (PDFs), such as state and model probability distribution functions, to generate a prior probability distribution function, which is input into a probabilistic updater. The probabilistic updater integrates sensor data with the prior probability distribution function to generate a posterior probability distribution function passed to a probabilistic sampler, which estimates one or more parameters using the posterior, which is output or re-sampled and used as an input to the dynamic state-space model in the iterative algorithm. In various embodiments, the probabilistic data signal processor is used to filter output and/or estimate a value of a new physiological parameter from a biomedical device using appropriate physical models, which optionally include biomedical, chemical, electrical, optical, mechanical, and/or fluid based models. For clarity, examples of heart and cardiovascular medical devices are provided.

In one example, an analyzer is configured to: (1) receive discrete first input data, related to a first sub-system of the system, from a first instrument and (2) receive discrete second input data, related to a second sub-system of the system, from a second instrument. The analyzer optionally includes a system processor configured to fuse the first input data and the second input data into fused data. The system processor optionally includes: (1) a probabilistic processor configured to convert the fused data into at least two probability distribution functions and (2) a dynamic state-space model, the dynamic state-space model including at least one probabilistic model configured to operate on the at least two probability distribution functions. The system processor iteratively circulates the at least two probability distribution functions in the dynamic state-space model in synchronization with receipt of at least one of: (1) updated first input data and (2) updated second input data. The system processor is further configured to process the probability distribution functions to generate an output related to the state of the system.

In another example, an analyzer is configured for processing sensor data representative of a body where the analyzer includes: a physical model representative of function of a body constituent; the physical model coded into a digital signal processor electrically connected, optionally wirelessly, to a computer embedded in the analyzer. The digital signal processor is configured to: (1) generate a prior probability distribution function using the physical model and (2) repetitively fuse input data originating from at least two types of medical instruments with the prior probability distribution function to generate a posterior probability distribution function. Further, the processor is configured to process the posterior probability distribution function to generate an output of at least one of: (1) a monitored parameter value representative of the body and (2) an estimated parameter value representative of the body.

In various embodiments, the probabilistic digital signal processor comprises one or more of a dynamic state-space model, a dual or joint updater, and/or a probabilistic sampler, which process input data, such as sensor data and generates an output. Preferably, the probabilistic digital signal processor (1) iteratively processes the data and/or (2) uses a mathematical model of the physical system in processing the input data.

The probabilistic digital signal processor optionally:
operates on or in conjunction with a sensor in a mechanical system;
filters input data;
operates using data from a medical meter, where the medical meter yields a first physical parameter from raw data, to generate a second physical parameter not output by the medical meter;
operates on discrete/non-probabilistic input data, such as from a mechanical device or a medical device to generate a probabilistic output function;
iteratively circulates or dynamically circulates a probability distribution function through at least two of the dynamic state-space model, the dual or joint updater, and/or the probabilistic sampler;
fuses or combines output from multiple sensors, such as two or more medical devices; and
prognosticates probability of future events.

To facilitate description of the probabilistic digital signal processor, a non-limiting example of a hemodynamics process model is provided. In this example, the probabilistic digital signal processor is provided:
raw sensor data, such as current, voltage, and/or resistance; and/or
output from a medical device to a first physical or chemical parameter.

In this example, the medical device is a pulse oximeter and the first parameter from the pulse oximeter provided as input to the probabilistic digital signal processor is one or more of:
raw data, such as a voltage waveform that correlates to light absorption by blood;
heart rate; and/or
blood oxygen saturation.

The probabilistic digital signal processor uses a physical model, such as a probabilistic model, to operate on the first physical parameter to generate a second physical parameter, where the second physical parameter is not the first physical parameter. For example, the output of the probabilistic digital signal processor when provided with the pulse oximeter data is one or more of:
a heart stroke volume;
a cardiac output flow rate;
an aortic blood pressure; and/or
a radial blood pressure.

Optionally, the output from the probabilistic model is an updated, an error filtered, and/or a smoothed version of the original input data, such as a smoothed blood oxygen saturation percentage as a function of time. The hemodynamics model is further described, infra.

To facilitate description of the probabilistic digital signal processor, another non-limiting example of an electrocardiograph process model is provided. In this example, the probabilistic digital signal processor is provided:
raw sensor data, such as intensity, an electrical current, and/or a voltage; and/or
output from a medical device, such as an electrocardiogram, to a first physical or electrical parameter.

In this example, the medical device is a electrocardiograph and the first physical or electrical parameter from the electrocardiograph system provided as input to the probabilistic digital signal processor is one or more of:
raw data; and/or
an electrocardiogram.

The probabilistic digital signal processor uses a physical model, such as a probabilistic model, to operate on the first physical parameter to generate a second physical parameter or an indicator, where the second physical parameter is not the first physical parameter. For example, the output of the probabilistic digital signal processor when provided with the electrocardiogram or raw data is one or more of:
an arrhythmia detection;
an ischemia warning; and/or
a heart attack prediction.

Optionally, the output from the probabilistic model is an updated, error filtered, or smoothed version of the original input data. For example, the probabilistic processor uses a physical model where the output of the model processes low signal-to-noise ratio events to yield an early warning of any of the arrhythmia detection, the ischemia warning, and/or the heart attack prediction. The electrocardiograph model is further described, infra.

To still further facilitate description of the probabilistic digital signal processor, non-limiting fusion examples are provided, which combine data from one or more of:
a mechanical system;
a sensor monitoring a mechanical device;
an electrodynamics based medical device;
a hemodynamic based medical device;
accelerometer data; and
an environmental meter.

As further described, supra, fusion of signals or sensor data from a plurality of devices allows:
- detection of a false positive or false negative signal from a first device with a second device;
- noise recognized in first sensor data as the noise is not present in a second sensor type or is correlated with noise of the second sensor type;
- fusion of environmental data with medical data;
- determination of an additional parameter not independently measured with individual data types of the fused data;
- electrocardiograph data to aid in analysis of pulse oximeter data and vise-versa; and/or
- electrodynamic information to aid in analysis of hemodynamic information and vise-versa.

Deterministic vs. Probabilistic Models

Typically, computer-based systems use a mapping between observed symptoms of failure and the equipment where the mapping is built using deterministic techniques. The mapping typically takes the form of a look-up table, a symptom-problem matrix, trend analysis, and production rules. In stark contrast, alternatively probabilistic models are used to analyze a system. An example of a probabilistic model, referred to herein as an intelligent data extraction system is provided, infra.

Intelligent Data Extraction System

Referring now to FIG. 1, an algorithm based intelligent data extraction system 100 is illustrated. The intelligent data extraction system 100 uses a controller 110 to control a sensor 120. The sensor 120 is used to measure a parameter and/or is incorporated into a biomedical apparatus 130. Optionally, the controller 110 additionally controls the medical apparatus and/or is built into the biomedical apparatus 130. The sensor 120 provides readings to a data processor or a probabilistic digital signal processor 200, which provides feedback to the controller 110 and/or provides output 150. In one embodiment, the controller 110 comprises a microprocessor in a computer or computer system, an embedded device, and/or an embedded processor.

Herein, to enhance understanding and for clarity of presentation, non-limiting examples of an intelligent data extraction system operating on a hemodynamics biomedical devices are used to illustrate methods, systems, and apparatus described herein. Generally, the methods, systems, and apparatus described herein extend to any apparatus having a moveable part and/or to any medical device. Examples of the dynamic state-space model with a probabilistic digital signal processor used to estimate parameters of additional biomedical systems are provided after the details of the processing engine are presented.

Still referring to FIG. 1, in a pulse oximeter example the controller 110 controls a sensor 120 in the pulse oximeter apparatus 130. The sensor 120 provides readings, such as a spectral reading to the probabilistic digital signal processor 200, which is preferably a probability based data processor. The probabilistic digital signal processor 200 optionally operates on the input data or provides feedback to the controller 110, such as state of the patient, as part of a loop, iterative loop, time series analysis, and/or generates the output 150, such as a smoothed biomedical state parameter or a new biomedical state parameter. For clarity, the pulse oximeter apparatus is used repetitively herein as an example of the biomedical apparatus 130 upon which the intelligent data extraction system 100 operates. The probabilistic digital signal processor 200 is further described, infra.

Data Processor

Figure 2:
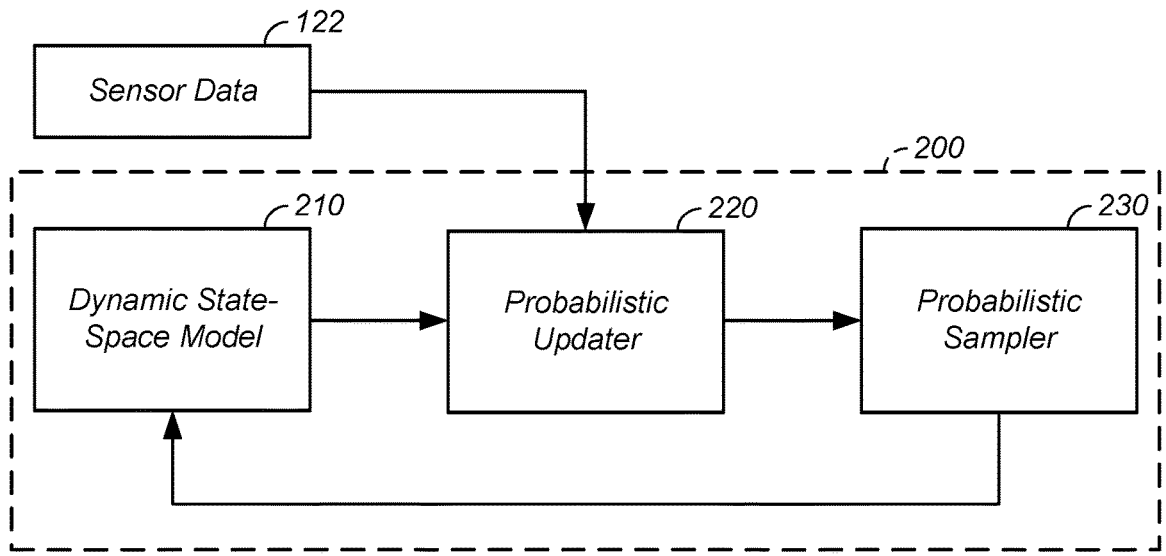
FIG. 2 provides a block diagram of a data processor.

Referring now to FIG. 2, the probabilistic digital signal processor 200 of the intelligent data extraction system 100 is further described. Generally, the data processor includes a dynamic state-space model 210 (DSSM) and a probabilistic updater 220 that iteratively or sequentially operates on sensor data 122 from the sensor 120. The probabilistic updater 220 outputs a probability distribution function to a parameter updater or a probabilistic sampler 230, which generates one or more parameters, such as an estimated diagnostic parameter, which is sent to the controller 110, is used as part of an iterative loop as input to the dynamic state-space model 210, and/or is a basis of the output 150. The dynamic state-space model 210 and probabilistic updater 220 are further described, infra.

Figure 3:
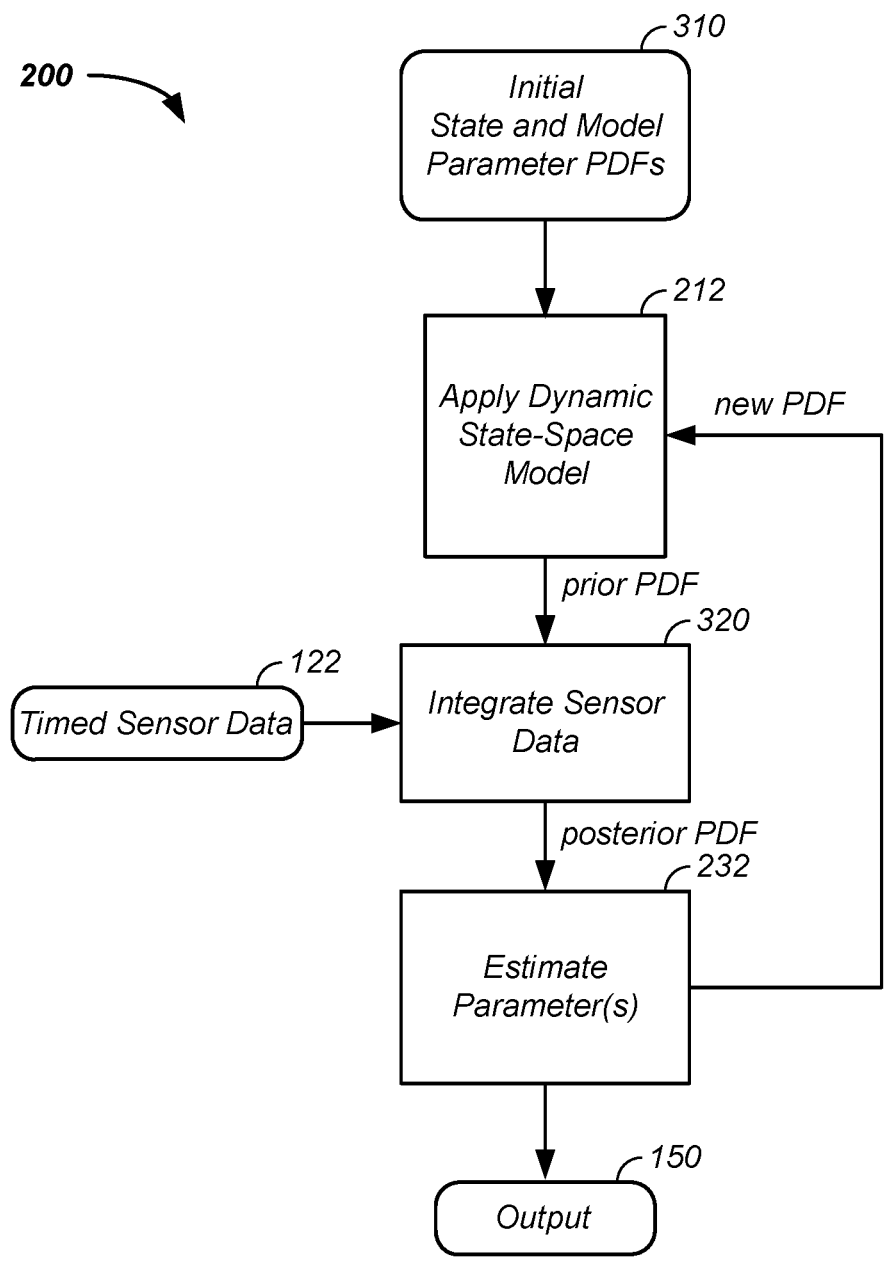
FIG. 3 is a flow diagram of a probabilistic digital signal processor.

Referring now to FIG. 3, the probabilistic digital signal processor 200 is further described. Generally, a probability function, a probability distribution function (PDF), an initial probability distribution function, or a set of initial probability distribution functions 310 are input to the dynamic state-space model 210. In a process 212, the dynamic state-space model 210 operates on the initial probability distribution functions 310 to generate a prior probability distribution function, hereinafter also referred to as a prior or as a prior PDF. For example, an initial state parameter 312 probability distribution function and an initial model parameter 314 probability distribution function are provided as initial inputs to the dynamic state-space model 210. The dynamic state-space model 210 operates on the initial state parameter 312 and/or initial model parameter 314 to generate the prior probability distribution function, which is input to the probabilistic updater 220. In a process 320, the probabilistic updater 220 integrates sensor data, such as timed sensor data 122, by operating on the sensor data and on the prior probability distribution function to generate a posterior probability distribution function, herein also referred to as a posterior or as a posterior PDF. In a process 232, the probabilistic sampler 230 estimates one or more parameters using the posterior probability distribution function. The probabilistic sampler 230 operates on the state and model parameter probability distribution functions from the state and model parameter updaters 224, 226, respectively or alternatively operates on the joint parameter probability distribution function and calculates an output. The output is optionally:
- the state or joint parameter PDF, passed to the PDF resampler 520; and/or;
- output values resulting from an operation on the inputs to the output 150 or output display or to the 110 controller.

In one example, expectation values such as a mean and a standard deviation of a state parameter are calculated from the state parameter PDF and output to the user, such as for diagnosis. In another example, expectation values, such as a mean value of state and model parameters, are calculated and then used in a model to output a more advanced diagnostic or prognostic parameter. In a third example, expectation values are calculated on a PDF that is the result of an operation on the state parameter PDF and/or model parameter PDF. Optionally, the output is to the same parameter as the state parameter PDF or model parameter PDF. Other data, such as user-input data, is optionally used in the output operation. The estimated parameters of the probabilistic sampler 230 are optionally used as a feedback to the dynamic state-space model 210 or are used to estimate a biomedical parameter. The feedback to the dynamic state-space model 210 is also referred to as a new probability distribution function or as a new PDF, which is/are updates of the initial state parameter 312 and/or are updates of the initial model parameter 314. Again, for clarity, an example of an estimated parameter 232 is a measurement of the heart/cardiovascular system, such as a heartbeat stroke volume.

Dual Estimator

Figure 4:
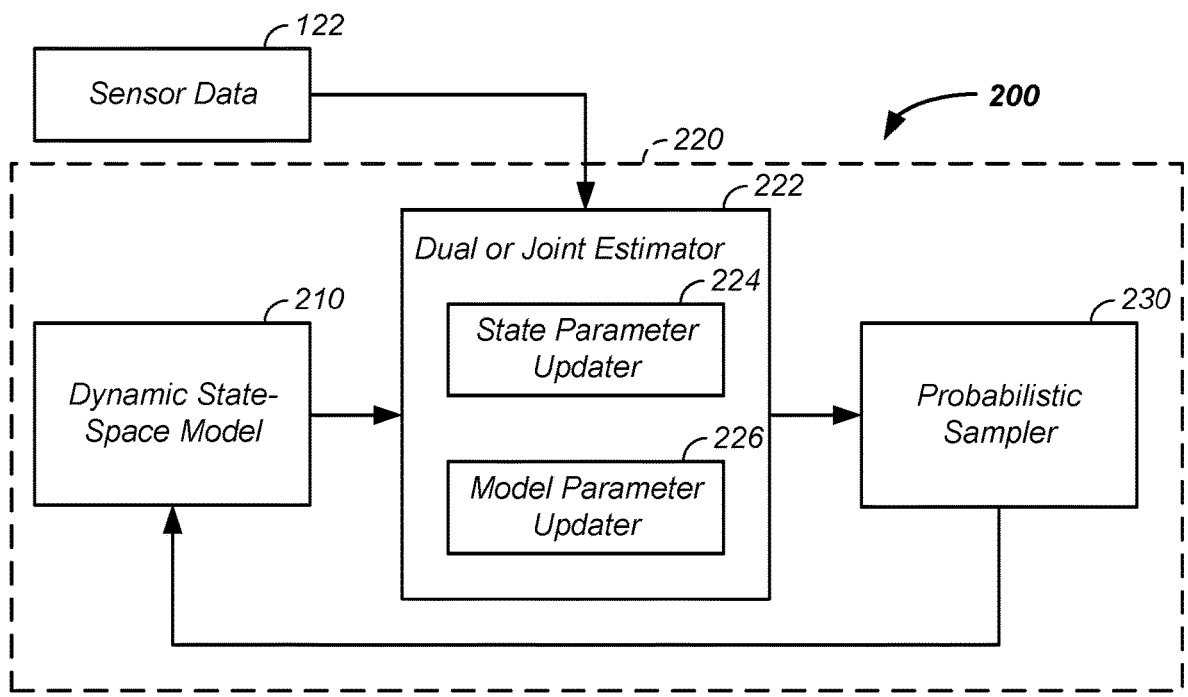
FIG. 4 illustrates a dual estimator.

In another embodiment, the probabilistic updater 220 of the probabilistic digital signal processor 200 uses a dual or joint estimator 222. Referring now to FIG. 4, the joint estimator 222 or dual estimation process uses both a state parameter updater 224 and a model parameter updater 226. Herein, for clarity, a dual estimator 222 is described. However, the techniques and steps described herein for the dual estimator are additionally applicable to a joint estimator as the state parameter and model parameter vector and/or matrix of the dual estimator are merely concatenated in a joint parameter vector and/or are joined in a matrix in a joint estimator.

State Parameter Updater

A first computational model used in the probabilistic updater 220 includes one or more state variables or state parameters, which correspond to the parameter being estimated by the state parameter updater 224. In the case of the hemodynamics monitoring apparatus, state parameters include time, intensity, reflectance, and/or a pressure. Some or all state parameters are optionally selected such that they represent the "true" value of noisy timed sensor data. In this case, calculation of such a posterior state parameter PDF constitutes a noise filtering process and expectation values of the PDF optionally represent filtered sensor values and associated confidence intervals.

Model Parameter Updater

A second computational model used in the probabilistic updater 220 includes one or more model parameters updated in the model parameter updater 226. For example, in the case of the hemodynamics monitoring apparatus, model parameters include: a time interval, a heart rate, a stroke volume, and/or a blood oxygenation percentage.

Hence, the dual estimator 222 optionally simultaneously or in a processing loop updates or calculates one or both of the state parameters and model parameters. The probabilistic sampler 230 is used to determine the estimated value for the biomedical parameter, which is optionally calculated from a state parameter, a model parameter, or a combination of one or more of the state parameter and/or the model parameter.

Figure 5:
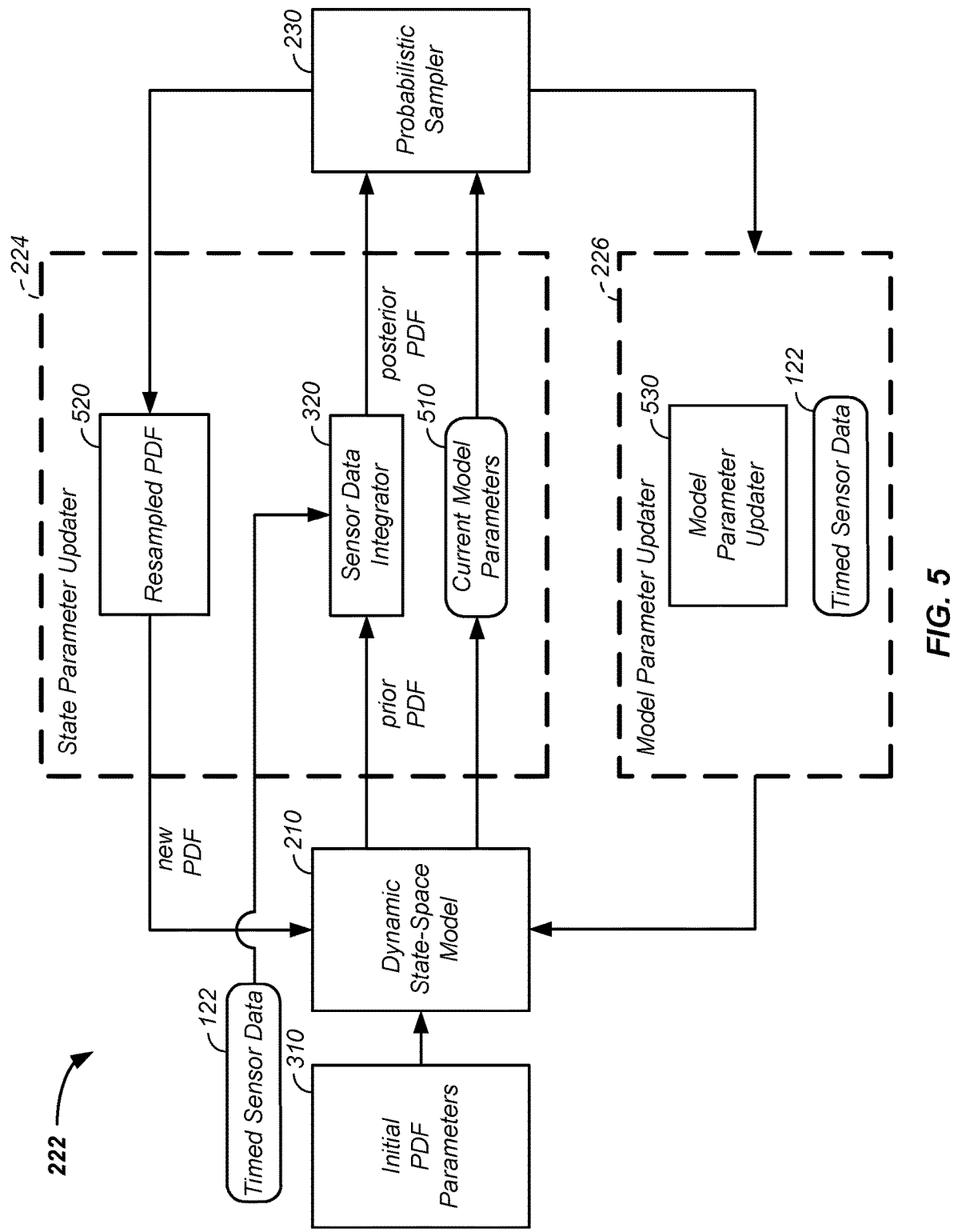
FIG. 5 expands the dual estimator.

Referring still to FIGS. 3 and 4 and now referring to FIG. 5, a first example of the dual estimator 222 is described and placed into context of the dynamic state-space model 210 and probabilistic sampler 230 of the probabilistic digital signal processor 200. The state parameter updater 224 element of the dual estimator 222 optionally:

uses a sensor data integrator 320 operating on the prior PDF being passed from the dynamic state-space model 210 and optionally operates on new timed sensor data 122, to produce the posterior PDF passed to the probabilistic sampler 230;

operates on current model parameters 510; and/or in a process 520, the state parameter updater 224 optionally re-samples a probability distribution function passed from the probabilistic sampler 230 to form the new probability distribution function passed to the dynamic state-space model 210.

In addition, in a process 530 the model parameter updater 226 optionally integrates new timed sensor data 122 with output from the probabilistic sampler 230 to form new input to the dynamic state-space model 210.

Figure 6:
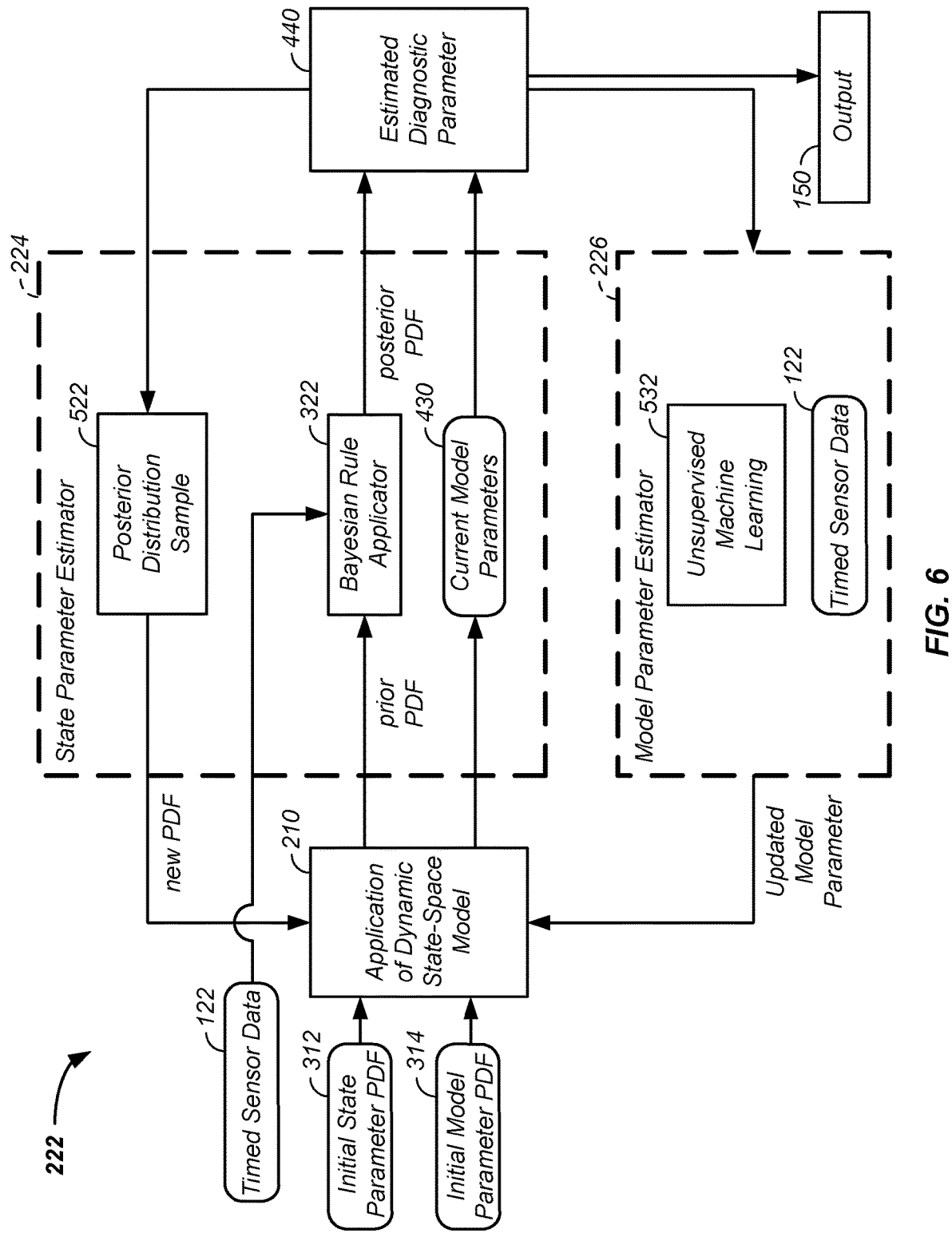
FIG. 6 illustrates state and model parameter estimators.

Referring now to FIG. 6, a second example of a dual estimator 222 is described. In this example:

initial state parameter probability distribution functions 312 are passed to the dynamic state-space model 210; and/or initial model parameter probability distribution functions 314 are passed to the dynamic state-space model 210.

Further, in this example:

a Bayesian rule applicator 322 is used as an algorithm in the sensor data integrator 320;

a posterior distribution sample algorithm 522 is used as the algorithm in the resampling of the PDF process 520; and a supervised or unsupervised machine learning algorithm 532 is used as the algorithm in the model parameter updater 530.

Filtering

In various embodiments, algorithms, data handling steps, and/or numerical recipes are used in a number of the steps and/or processes herein. The inventor has determined that several algorithms are particularly useful: sigma point Kalman filtering, sequential Monte Carlo filtering, and/or use of a sampler. In a first example, either the sigma point Kalman filtering or sequential Monte Carlo algorithms are used in generating the probability distribution function. In a second example, either the sigma point Kalman filtering or sequential Monte Carlo algorithms are used in the unsupervised machine learning 532 step in the model parameter updater 530 to form an updated model parameter. The sigma point Kalman filtering, sequential Monte Carlo algorithms, and use of a sampler are further described, infra.

Sigma Point Kalman Filter

Filtering techniques based on Kalman and extended Kalman techniques offer advantages over conventional methods and work well for filtering linear systems or systems with small nonlinearities and Gaussian noise. These Kalman filters, however, are not optimum for filtering highly nonlinear systems and/or non-Gaussian/non-stationary noise. In stark contrast, sigma point Kalman filters are well suited to data having nonlinearities and non-Gaussian noise.

Herein, a sigma point Kalman filter (SPKF) refers to a filter using a set of weighted sigma-points that are deterministically calculated, such as by using the mean and square-root decomposition, or an equivalent, of the covariance matrix of a probability distribution function to about capture or completely capture at least the first and second order moments. The sigma-points are subsequently propagated in time through the dynamic state-space model 210 to generate a prior sigma-point set. Then, prior statistics are calculated using tractable functions of the propagated sigma-points, weights, and new measurements.

Sigma point Kalman filter advantages and disadvantages are described herein. A sigma point Kalman filter interprets a noisy measurement in the context of a mathematical model describing the system and measurement dynamics. This gives the sigma point Kalman filter inherent superior performance to all "model-less" methods, such as Wiener filtering, wavelet de-noising, principal component analysis, independent component analysis, nonlinear projective filtering, clustering methods, adaptive noise cancelling, and many others.

A sigma point Kalman filter is superior to the basic Kalman filter, extended Kalman filter, and related variants of the Kalman filters. The extended Kalman filter propagates the random variable using a single measure, usually the mean, and a first order Taylor expansion of the nonlinear dynamic state-space model 210. Conversely, a sigma point Kalman filter decomposes the random variable into distribution moments and propagates those using the unmodified nonlinear dynamic state-space model 210. As a result, the sigma point Kalman filter yields higher accuracy with equal algorithm complexity, while also being easier to implement in practice.

In the sigma-point formalism the probability distribution function is represented by a set of values called sigma points, those values represent the mean and other moments of the distribution which, when input into a given function, recovers the probability distribution function.

Sequential Monte Carlo

Sequential Monte Carlo (SMC) methods approximate the prior probability distribution function through use of a set of weighted sample values without making assumptions about its form. The samples are then propagated in time through the unmodified dynamic state-space model 210. The resulting samples are used to update the posterior via Bayes rule and the latest noisy measurement or timed sensor data 122.

In the sequential Monte Carlo formalism the PDF is actually discretized into a collection of probability "particles" each representing a segment of the probability density in the probability distribution function.

SPKF and SMC

In general, sequential Monte Carlo methods have analysis advantages compared to the sigma point Kalman filters, but are more computationally expensive. However, the SPKF uses a sigma-point set, which is an exact representation only for Gaussian probability distribution functions (PDFs). As a result, SPKFs lose accuracy when PDFs depart heavily from the Gaussian form, such as with bimodal, heavily-tailed, or nonstationary distributions. Hence, both the SMC and SPKF filters have advantages. However, either a SMC analysis or SPKF is used to propagate the prior using the unmodified DSSM. Herein, generally when a SMC filter is used a SPKF filter is optionally used and vise-versa.

A SPKF or a SMC algorithm is used to generate a reference signal in the form of a first probability distribution from the model's current (time=t) physiological state. The reference signal probability distribution and a probability distribution generated from a measured signal from a sensor at a subsequent time (time=t+n) are convoluted using Bayesian statistics to estimate the true value of the measured physiological parameter at time=t+n. The probability distribution function is optionally discrete or continuous. The probability distribution function is optionally used to identify the probability of each value of an unidentified random variable, such as in a discrete function, or the probability of the value falling within a particular interval, such as in a continuous function.

Sampler

Probability distribution functions (PDFs) are optionally continuous or discrete. In the continuous case the probability distribution function is represented by a function. In the discrete case, the variable space is binned into a series of discrete values. In both the continuous and discrete cases, probability distribution functions are generated by first decomposing the PDF into a set of samplers that are characteristic of the probability distribution function and then the samplers are propagated via computations through the DSSM (prior generation) and sensor data integrator (posterior generation). Herein, a sampler is a combination of a value and label. The value is associated with the x-axis of the probability distribution function, which denotes state, model, or joint parameters. The label is associated with the y-axis of the probability distribution function, which denotes the probability. Examples of labels are: weight, frequency, or any arbitrary moment of a given distribution, such as a first Gaussian moment. A powerful example of characteristic sampler use is decomposing the PDF into a series of state values with attached first Gaussian moment labels. This sum of several Gaussian distributions with different values and moments usually gives accurate approximations of the true probability distribution function.

Probabilistic Digital Signal Processor

As described, supra, in various embodiments, the probabilistic digital signal processor 200 comprises one or more of a dynamic state-space model 210, a dual or joint estimator 222, and/or a probabilistic sampler 230, which processes input data, such as sensor data 122 and generates an output 150. Preferably, the probabilistic digital signal processor 200 (1) iteratively processes the data and/or (2) uses a physical model in processing the input data.

The probabilistic digital signal processor 200 optionally:
filters input data;
operates using data from a medical meter, where the medical meter yields a first physical parameter from raw data, to generate a second physical parameter not output by the medical meter;
operates on discrete/non-probabilistic input data from a medical device to generate a probabilistic output function;
iteratively circulates a probability distribution function through at least two of the dynamic state-space model, the dual or joint updater, and/or the probabilistic sampler;
fuses or combines output from multiple medical devices; and/or
prognosticates probability of future events.

A hemodynamics example of a probabilistic digital signal processor 200 operating on data from a pulse oximeter is used to describe these processes, infra.

Dynamic State-Space Model

The dynamic state-space model 210 is further described herein.

Figure 7:
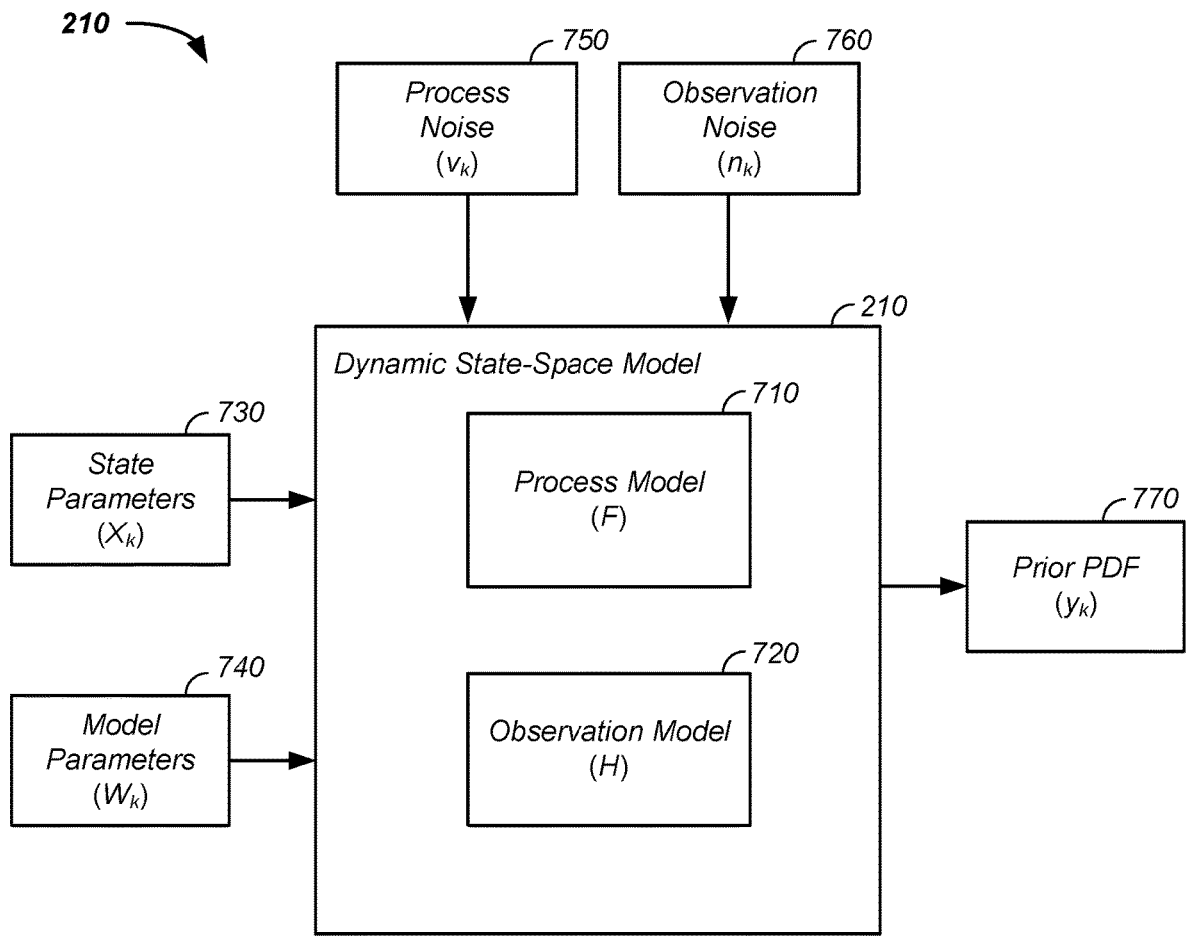
FIG. 7 provides inputs and internal operation of a dynamic state-space model.

Referring now to FIG. 7, schematics of an exemplary dynamic state-space model 210 (DSSM) used in the processing of data is provided. The dynamic state-space model 210 typically and optionally includes a process model 710 and/or an observation model 720. The process model 710, F, which mathematically represents mechanical processes involved in generating one or more biomedical parameters, is measured by a sensor, such as a sensor sensing a mechanical component and describes the state of the biomedical apparatus, output of the biomedical apparatus, and/or state of the patient over time in terms of state parameters. This mathematical model optimally includes mathematical representations accounting for process noise 750, such as mechanically caused artifacts that may cause the sensor to produce a digital output that does not produce an accurate measurement for the biomedical parameter being sensed. The dynamic state-space model 210 also comprises an observational model 720, H, which mathematically represents processes involved in collecting sensor data measured by the mechanical sensor. This mathematical model optimally includes mathematical representations accounting for observation noise produced by the sensor apparatus that may cause the sensor to produce a digital output that does not produce an accurate measurement for a biomedical parameter being sensed. Noise terms in the mathematical models are not required to be additive.

While the process and observation mathematical models 710, 720 are optionally conceptualized as separate models, they are preferably integrated into a single mathematical model that describes processes that produce a biomedical parameter and processes involved in sensing the biomedical parameter. The integrated process and observation model, in turn, is integrated with a processing engine within an executable program stored in a data processor, which is configured to receive digital data from one or more sensors and to output data to a display and/or to another output format.

Still referring to FIG. 7, inputs into the dynamic state-space model 210 include one or more of:
- state parameters 730, such as the initial state parameter probability distribution function 312 or the new PDF;
- model parameters 740, such as the initial noise parameter probability distribution function 314 or an updated model parameter from the unsupervised machine learning module 532;
- process noise 750; and/or
- observation noise 760.

Hemodynamics Dynamic State-Space Model

Figure 8:
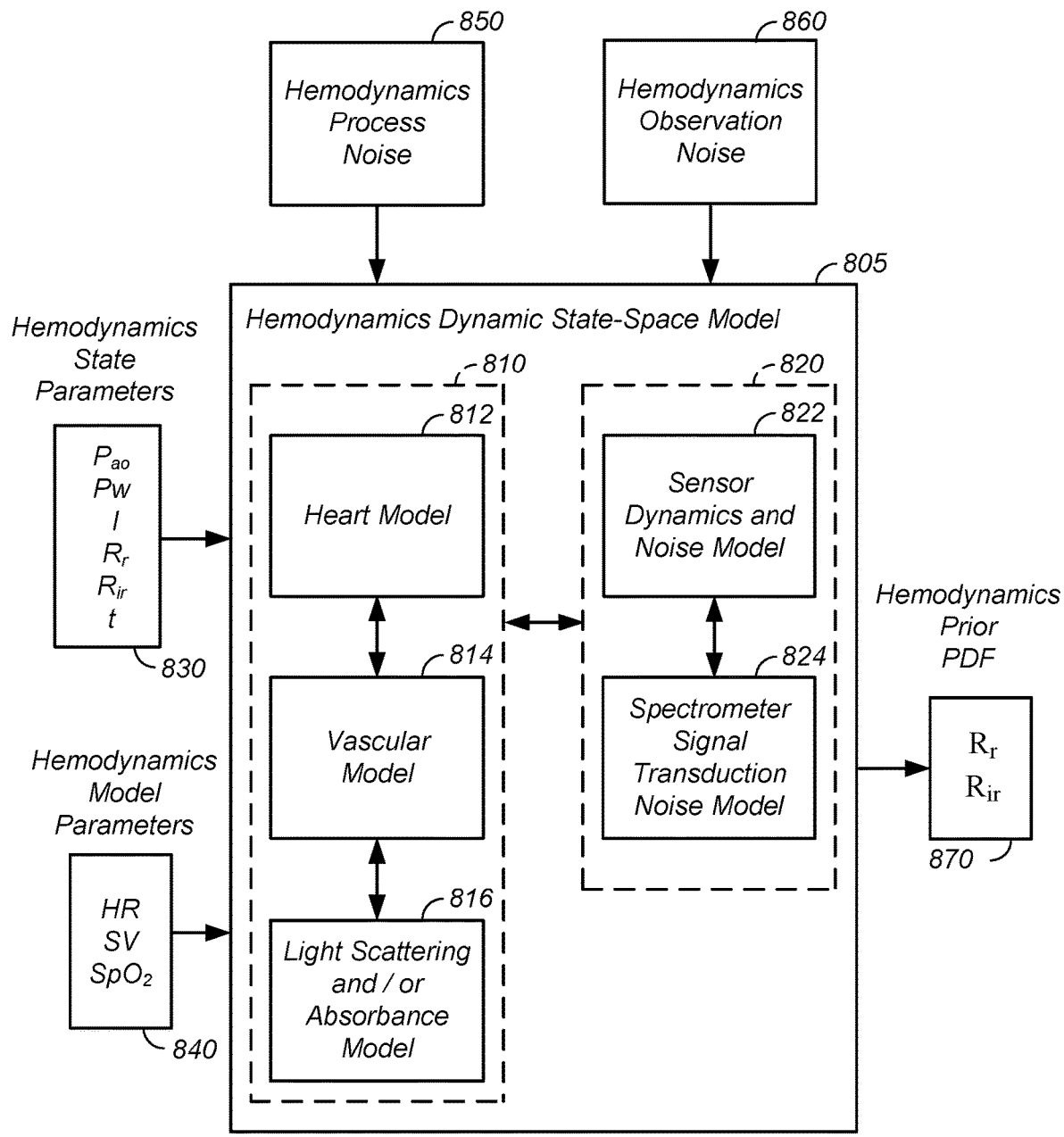
FIG. 8 is a flow chart showing the components of a hemodynamics dynamic state-space model.

A first non-limiting specific example is used to facilitate understanding of the dynamic state-space model 210. Referring now to FIG. 8, a hemodynamics dynamic state-space model 805 flow diagram is presented. Generally, the hemodynamics dynamic state-space model 805 is an example of a dynamic state-space model 210. The hemodynamics dynamic state-space model 805 combines sensor data 122, such as a spectral readings of skin, with a physical parameter based probabilistic model. The hemodynamics dynamic state-space model 805 operates in conjunction with the probabilistic updater 220 to form an estimate of heart/cardiovascular state parameters.

To facilitate description of the probabilistic digital signal processor, a non-limiting example of a hemodynamics process model is provided. In this example, the probabilistic digital signal processor is provided:
- raw sensor data, such as current, voltage, and/or resistance; and/or
- a first physical parameter output from a medical device.

In this example, the medical device is a pulse oximeter collecting raw data and the first physical parameter from the pulse oximeter provided as input to the probabilistic digital signal processor is one or more of:
- a heart rate; and/or
- a blood oxygen saturation.

The probabilistic digital signal processor uses a physical model, such as a probabilistic model, to operate on the first physical parameter and/or the raw data to generate a second physical parameter, where the second physical parameter is optionally not the first physical parameter. For example, the output of the probabilistic digital signal processor using a physical hemodynamic model, when provided with the pulse oximeter data, is one or more of:
- a heart stroke volume;
- a cardiac output flow rate;
- an aortic blood pressure; and/or
- a radial blood pressure.

Optionally, the output from the probabilistic model is an updated, error filtered, and/or smoothed version of the original input data, such as a smoothed blood oxygen saturation percentage as a function of time.

Still referring to FIG. 8, to facilitate description of the hemodynamics dynamic state-space model 805, a non-limiting example is provided. In this example, the hemodynamics dynamic state-space model 805 is further described. The hemodynamics dynamic state-space model 805 preferably includes a hemodynamics process model 810 corresponding to the dynamic state-space model 210 process model 710. Further, the hemodynamics dynamic state-space model 805 preferably includes a hemodynamics observation model 820 corresponding to the dynamic state-space model 210 observation model 720. The hemodynamics process model 810 and hemodynamics observation model 820 are further described, infra.

Still referring to FIG. 8, the hemodynamics process model 810 optionally includes one or more of a heart model 812, a vascular model 814, and/or a light scattering or light absorbance model 816. The heart model 812 is a physics based probabilistic model of the heart and movement of blood in and/or from the heart. The vascular model 814 is a physics based probabilistic model of movement of blood in arteries, veins, and/or capillaries. The various models optionally share information. For example, blood flow or stroke volume exiting the heart in the heart model 812 is optionally an input to the arterial blood in the vascular model 814.

The light scattering and/or absorbance model 816 relates spectral information, such as from a pulse oximeter, to additional hemodynamics dynamic state-space model parameters, such as heart rate (HR), stroke volume (SV), and/or whole-blood oxygen saturation ($SpO_2$) or oxyhemoglobin percentage.

Still referring to FIG. 8, the hemodynamics observation model 820 optionally includes one or more of a sensor dynamics and noise model 822 and/or a spectrometer signal transduction noise model 824. Each of the sensor dynamics and noise model 822 and the spectrometer signal transduction noise model 824 are physics based probabilistic models related to noises associated with the instrumentation used to collect data, environmental influences on the collected data, and/or noise due to the human interaction with the instrumentation, such as movement of the sensor. As with the hemodynamics process model 810, the sub-models of the hemodynamics observation model 820 optionally share information. For instance, movement of the sensor noise is added to environmental noise.

Optionally and preferably, the hemodynamics observation model 820 shares information with and/provides information to the hemodynamics process model 810.

The hemodynamics dynamic state-space model 805 receives inputs, such as one or more of:
- hemodynamics state parameters 830;
- hemodynamics model parameters 840;
- hemodynamics process noise 850; and
- hemodynamics observation noise 860.

Examples of hemodynamics state parameters 830, corresponding to state parameters 730, include: radial pressure ($P_w$), aortic pressure ($P_{ao}$), time (t), a spectral intensity (I) or a related absorbance value, a reflectance or reflectance ratio, such as a red reflectance ($R_r$) or an infrared reflectance ($R_{ir}$), and/or a spectral intensity ratio ($I_R$). Examples of hemodynamics model parameters 840, corresponding to the more generic model parameters 740, include: heart rate (HR), stroke volume (SV), and/or whole-blood oxygen saturation ($SpO_2$). In this example, the output of the hemodynamics dynamic state-space model 805 is a prior probability distribution function with parameters of one or more of the input hemodynamics state parameters 830 after operation on by the heart dynamics model 812, a static number, and/or a parameter not directly measured or output by the sensor data. For instance, an input data stream is optionally a pulse oximeter yielding spectral intensities, ratios of intensities, and a percent oxygen saturation. However, the output of the hemodynamics dynamic state-space model is optionally a second physiological value, such as a stroke volume of the heart, which is not measured by the input biomedical device.

The hemodynamics dynamic state-space model 805 optionally receives inputs from one or more additional models, such as an irregular sampling model, which relates information collected at irregular or non-periodic intervals to the hemodynamics dynamic state-space model 805.

Generally, the hemodynamics dynamic state-space model 805 is an example of a dynamic state-space model 210, which operates in conjunction with the probabilistic updater 220 to form an estimate of a heart state parameter and/or a cardiovascular state parameter.

Generally, the output of the probabilistic signal processor 200 optionally includes a measure of uncertainty, such as a confidence interval, a standard deviation, and/or a standard error. Optionally, the output of the probabilistic signal processor 200 includes:

- a filtered or smoothed version of the parameter measured by the medical meter; and/or
- a probability function associated with a parameter not directly measured by the medical meter.

Example I

An example of a pulse oximeter with probabilistic data processing is provided as an example of the hemodynamics dynamic state-space model 805. The model is suitable for processing data from a pulse oximeter model. In this example, particular equations are used to further describe the hemodynamics dynamic state-space model 805, but the equations are illustrative and non-limiting in nature.

Heart Model

An example of the heart model 812 is used to further described an example of the hemodynamics dynamic state-space model 805. In this example, cardiac output is represented by equation 1, $$Q_{CO}(t) = \overline{Q}_{CO} \sum_{1}^{\delta} a_k \exp\left[\frac{-(t-b_k)^2}{c_k^2}\right] \tag{1}$$

where cardiac output $Q_{co}(t)$, is expressed as a function of heart rate (HR) and stroke volume (SV) and where $Q_{co}$=(HR×SV)/60. The values $a_k$, $b_k$, and $c_k$ are adjusted to fit data on human cardiac output.

Vascular Model

An example of the vascular model 814 of the hemodynamics state-space model 805 is provided. The cardiac output function pumps blood into a Windkessel 3-element model of the vascular system including two state variables: aortic pressure, $P_{ao}$, and radial (Windkessel) pressure, $P_w$, according to equations 2 and 3, $$P_{w,k+1} = \frac{1}{C_w R_p}((R_P + Z_0)Q_{CO} - P_{CO,k})\delta t + P_{w,k} \tag{2}$$

$$P_{ao,k+1} = P_{w,k+1} Z_0 Q_{CO} \tag{3}$$

where $R_p$ and $Z_0$ are the peripheral resistance and characteristic aortic impedance, respectively. The sum of these two terms is the total peripheral resistance due to viscous (Poiseuille-like) dissipation according to equation 4, $$Z_0 = \sqrt{\rho/AC_l} \tag{4}$$

where $\rho$ is blood density and $C_l$ is the compliance per unit length of artery. The elastic component due to vessel compliance is a nonlinear function including thoracic aortic cross-sectional area, A: according to equation 5, $$A(P_{CO}) = A_{max}\left[\frac{1}{2} + \frac{1}{\pi}\arctan\left(\frac{P_{CO} - P_0}{P_1}\right)\right] \tag{5}$$

where $A_{max}$, $P_0$, and $P_1$ are fitting constants correlated with age and gender according to equations 6-8.

$$A_{max} = (5.62 - 1.5(\text{gender})) \cdot \text{cm}^2 \tag{6}$$

$$P_0 = (76 - 4(\text{gender}) - 0.89(\text{age})) \cdot \text{mmHg} \tag{7}$$

$$P_1(57 - 0.44(\text{age})) \cdot \text{mmHg} \tag{8}$$

The time-varying Windkessel compliance, $C_w$, and the aortic compliance per unit length, $C_l$, are related in equation 9, $$C_w = lC_l = l\frac{dA}{dP_\infty} = l\frac{A_{max}/(\pi P_1)}{1 + \left(\frac{P_\infty - P_0}{P_1}\right)} \tag{9}$$

where l is the aortic effective length. The peripheral resistance is defined as the ratio of average pressure to average flow. A set-point pressure, $P_{set}$, and the instantaneous flow related to the peripheral resistance, $R_p$, according to equation 10, $$R_P = \frac{P_{set}}{(HR \cdot SV)/60} \tag{10}$$

are used to provide compensation to autonomic nervous system responses. The value for $P_{set}$ is optionally adjusted manually to obtain 120 over 75 mmHg for a healthy individual at rest.

Light Scattering and Absorbance Model

The light scattering and absorbance model 816 of the hemodynamics dynamic state-space model 805 is further described. The compliance of blood vessels changes the interactions between light and tissues with pulse. This is accounted for using a homogenous photon diffusion theory for a reflectance or transmittance pulse oximeter configuration according to equation 11, $$R = \frac{I_{ac}}{I_{dc}} = \frac{\Delta I}{I} = \frac{3}{2}\sum_{s}^{1} K(\alpha, d, r) \sum_{a}^{art} \Delta V_0 \tag{11}$$

for each wavelength. In this example, the red and infrared bands are centered at about 660±100 nm and at about 880±100 nm. In equation 11, I (no subscript) denotes the detected intensity, R, is the reflected light, and the alternating current intensity, $I_{ac}$, is the pulsating signal, ac intensity, or signal; and the background intensity, $I_{dc}$, is the direct current intensity or dc intensity; $\alpha$, is the attenuation coefficient; d, is the illumination length scale or depth of photon penetration into the skin; and r is the distance between the source and detector.

Referring again to the vascular model 814, $V_a$ is the arterial blood volume, which changes as the cross-sectional area of illuminated blood vessels, $\Delta A_w$, according to equation 12, $$\Delta V_a \approx r \cdot \Delta A_w \quad (12)$$

where r is the source-detector distance.

Referring again to the light scattering and absorbance model 816, the tissue scattering coefficient, $\Sigma'_s$, is assumed constant but the arterial absorption coefficient, $\Sigma_a^{art}$, which represents the extinction coefficients, depends on blood oxygen saturation, $SpO_2$, according to equation 13, $$\sum_a^{art} = \frac{H}{v_i}[SpO_2 \cdot \sigma_0^{100\%} + (1-SpO_2) \cdot \sigma_0^{0\%}] \quad (13)$$

which is the Beer-Lambert absorption coefficient, with hematocrit, H, and red blood cell volume, $v_i$. The optical absorption cross-sections, proportional to the absorption coefficients, for red blood cells containing totally oxygenated (HbO$_2$) and totally deoxygenated (Hb) hemoglobin are $\sigma_a^{100\%}$ and $\sigma_a^{0\%}$, respectively.

The function $K(\alpha, d, r)$, along with the scattering coefficient, the wavelength, sensor geometry, and oxygen saturation dependencies, alters the effective optical pathlengths, according to equation 14.

$$K(\alpha, d, r_s) \approx \frac{-r^2}{1+\alpha r} \quad (14)$$

The attenuation coefficient $\alpha$ is provided by equation 15, $$\alpha = \sqrt{3\Sigma_a(\Sigma_s + \Sigma_a)} \quad (15)$$

where $\Sigma_a$ and $\Sigma_s$ are whole-tissue absorption and scattering coefficients, respectively, which are calculated from Mie Theory.

Red, $\overline{K}_r$, and infrared, $\overline{K}_{ir}$, K values as a function of $SpO_2$ are optionally represented by two linear fits, provided in equations 16 and 17

$$\overline{K}_r \approx -4.03 \cdot SpO_2 - 1.17 \quad (16)$$

$$\overline{K}_{ir} \approx 0.102 \cdot SpO_2 - 0.753 \quad (17)$$

in mm$^2$. The overbar denotes the linear fit of the original function. Referring yet again to the vascular model 814, the pulsatile behavior of $\Delta A_w$, which couples optical detection with the cardiovascular system model, is provided by equation 18, $$\Delta A_w = \frac{A_{w,max}}{\pi} \frac{P_{w,1}}{P_{w,1}^2 + (P_{w,k+1} - P_{w,0})^2} \Delta P_w \quad (18)$$

where $P_{w,0} = (\frac{1}{3})P_0$ and $P_{w,i} = (\frac{1}{3})P_1$ account for the poorer compliance of arterioles and capillaries relative to the thoracic aorta. The subscript k is a data index and the subscript k+1 or k+n refers to the next or future data point, respectively.

Referring yet again to the light scattering and absorbance models, third and fourth state variables, the red and infrared reflected intensity ratios, $R = I_{ac}/I_{dc}$, are provided by equations 19 and 20.

$$R_{r,k+1} = c\Sigma'_{s,r}\overline{K}_r \Sigma_{a,r}^{art} \Delta A_w + R_{r,k} + v_r \quad (19)$$

$$R_{ir,k+1} = c\Sigma'_{s,ir}\overline{K}_{ir} \Sigma_{a,ir}^{art} \Delta A_w + R_{ir,k} + v_{ir} \quad (20)$$

Here, v is a process noise, such as an added random number or are Gaussian-distributed process noises intended to capture the baseline wander of the two channels, $\Sigma'_{s,r}$ and $\Sigma'_{s,ir}$ are scattering coefficients, and $\Sigma_{a,r}^{art}$ and $\Sigma_{a,ir}^{art}$ are absorption coefficients.

Sensor Dynamics and Noise Model

The sensor dynamics and noise model 822 is further described. The constant c subsumes all factors common to both wavelengths and is treated as a calibration constant. The observation model adds noises, n, with any probability distribution function to $R_r$ and $R_{ir}$, according to equation 21.

$$\begin{bmatrix} y_{r,k} \\ y_{ir,k} \end{bmatrix} = \begin{bmatrix} R_{r,k} \\ R_{ir,k} \end{bmatrix} + \begin{bmatrix} n_{r,k} \\ n_{ir,k} \end{bmatrix} \quad (21)$$

A calibration constant, c, was used to match the variance of the real $I_{ac}/I_{dc}$ signal with the variance of the dynamic state-space model generated signal for each wavelength. After calibration, the age and gender of the patient was entered. Estimates for the means and covariances of both state and parameter PDFs are optionally entered.

Figure 9A:
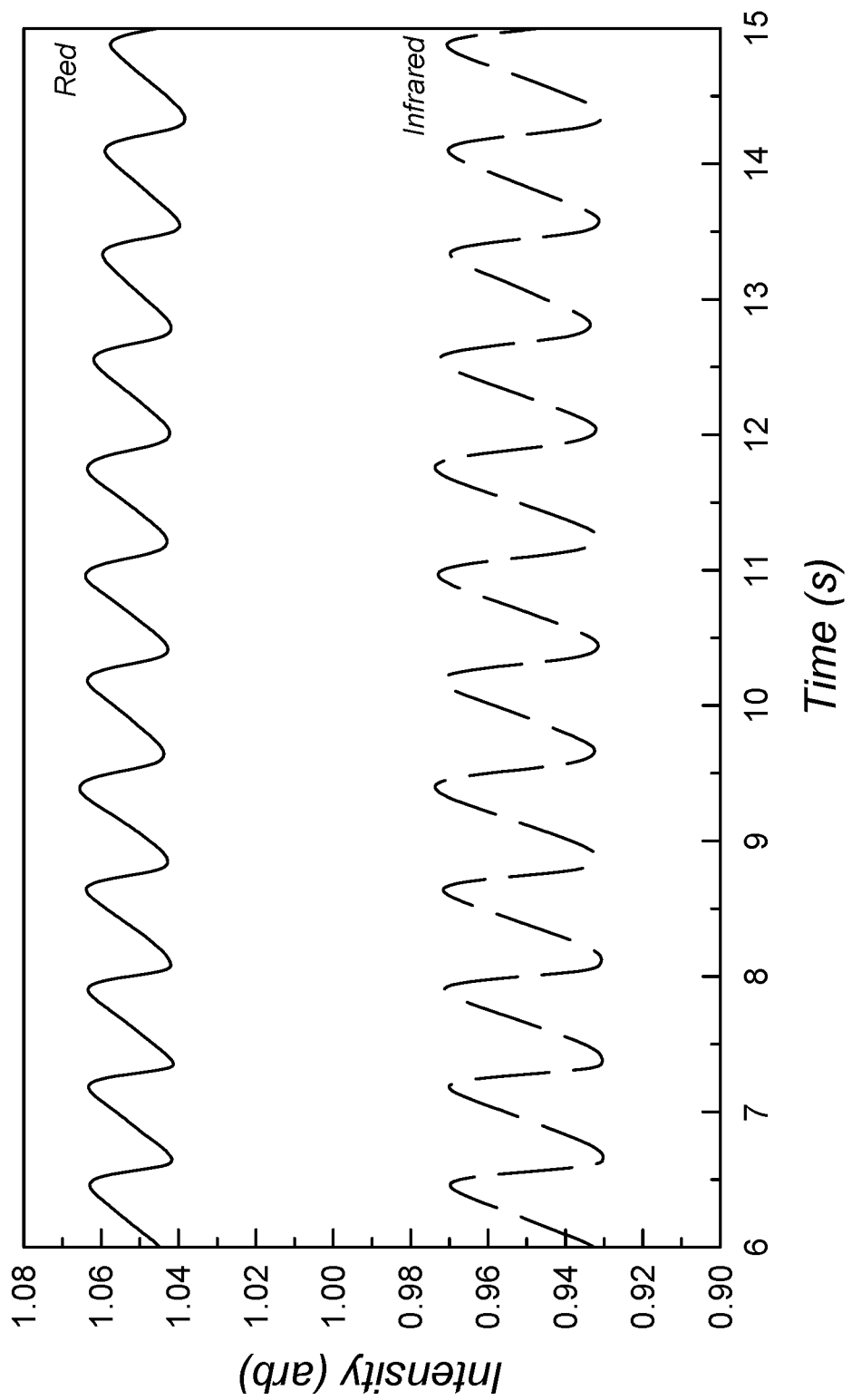
FIG. 9A illustrates input sensor data.
Figure 9D:
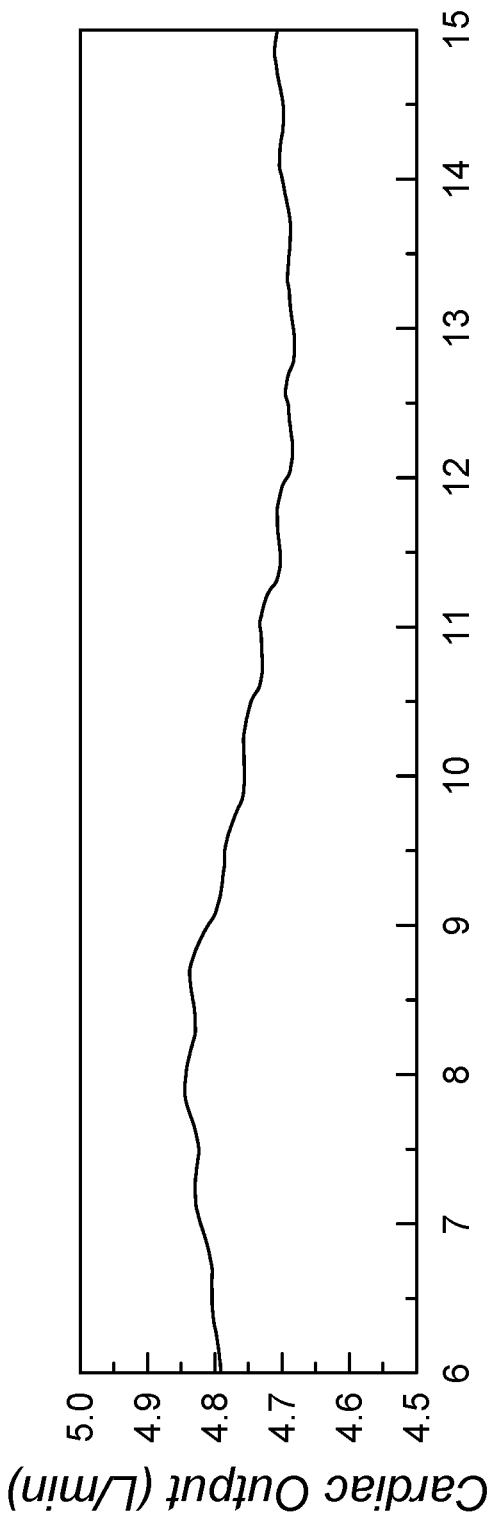
FIG. 9D illustrates processed cardiac output.
Figure 9E:
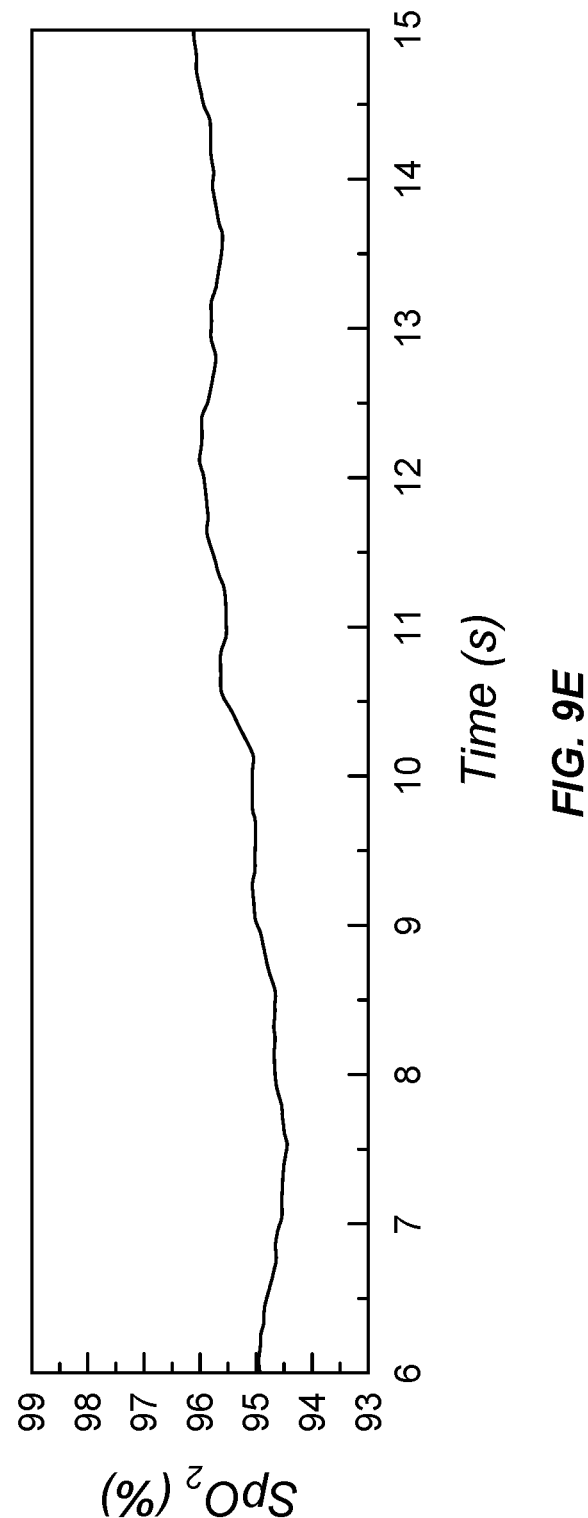
FIG. 9E illustrates processed oxygen.
Figure 9F:
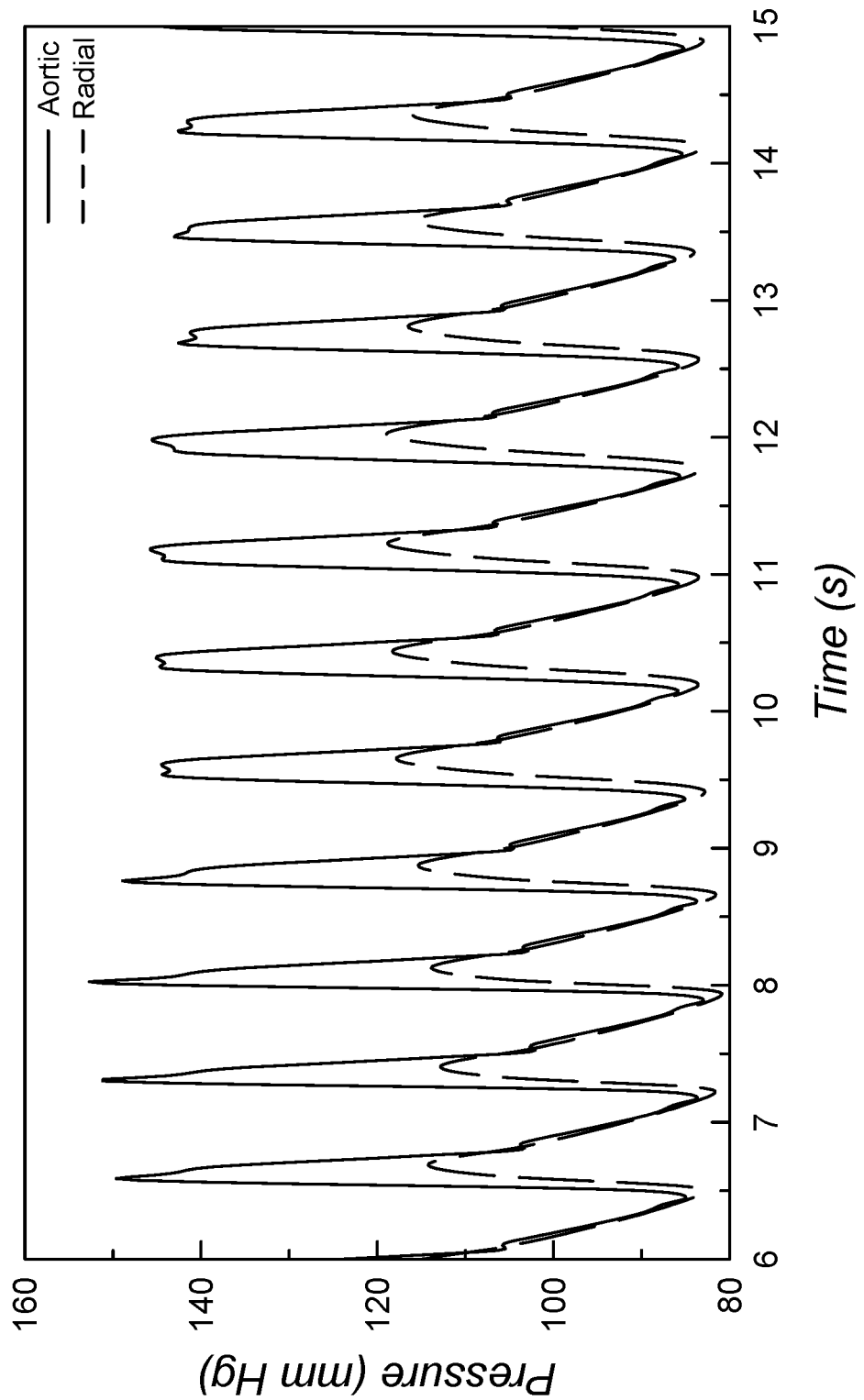
FIG. 9F illustrates processed pressure, from a data processor configured to process pulse oximetry data.

Processed data from a relatively high signal-to-noise ratio pulse oximeter data source is provided for about a fifteen second stretch of data is described. Referring now to FIG. 9A, input photoplethysmographic waveforms are provided. Using the hemodynamics dynamic state-space model 805, the input waveforms were used to extract heart rate (FIG. 9B), left-ventricular stroke volume (FIG. 9C), cardiac output (FIG. 9D), blood oxygen saturation (FIG. 9E), and aortic and systemic (radial) pressure waveforms (FIG. 9F). Several notable points are provided. First, the pulse oximeter provided a first physical value of a hemoglobin oxygen saturation percentage. However, the output blood oxygen saturation percentage, FIG. 9E, was processed by the probabilistic digital signal processor 200. Due to the use of the sensor dynamics and noise model 822 and the spectrometer signal transduction noise model, noisy data, such as due to ambulatory movement of the patient, is removed in the smoothed and filtered output blood oxygen saturation percentage. Second, some pulse oximeters provide a heart rate. However, in this case the heart rate output was calculated using the physical probabilistic digital signal processor 200 in the absence of a heart rate input data source 122. Third, each of the stroke volume, FIG. 9C, cardiac output flow rate, FIG. 9D, aortic blood pressure, FIG. 9E, and radial blood pressure, FIG. 9E, are second physical parameters that are different from the first physical parameter measured by the pulse oximeter photoplethysmographic waveforms.

Figure 10A:
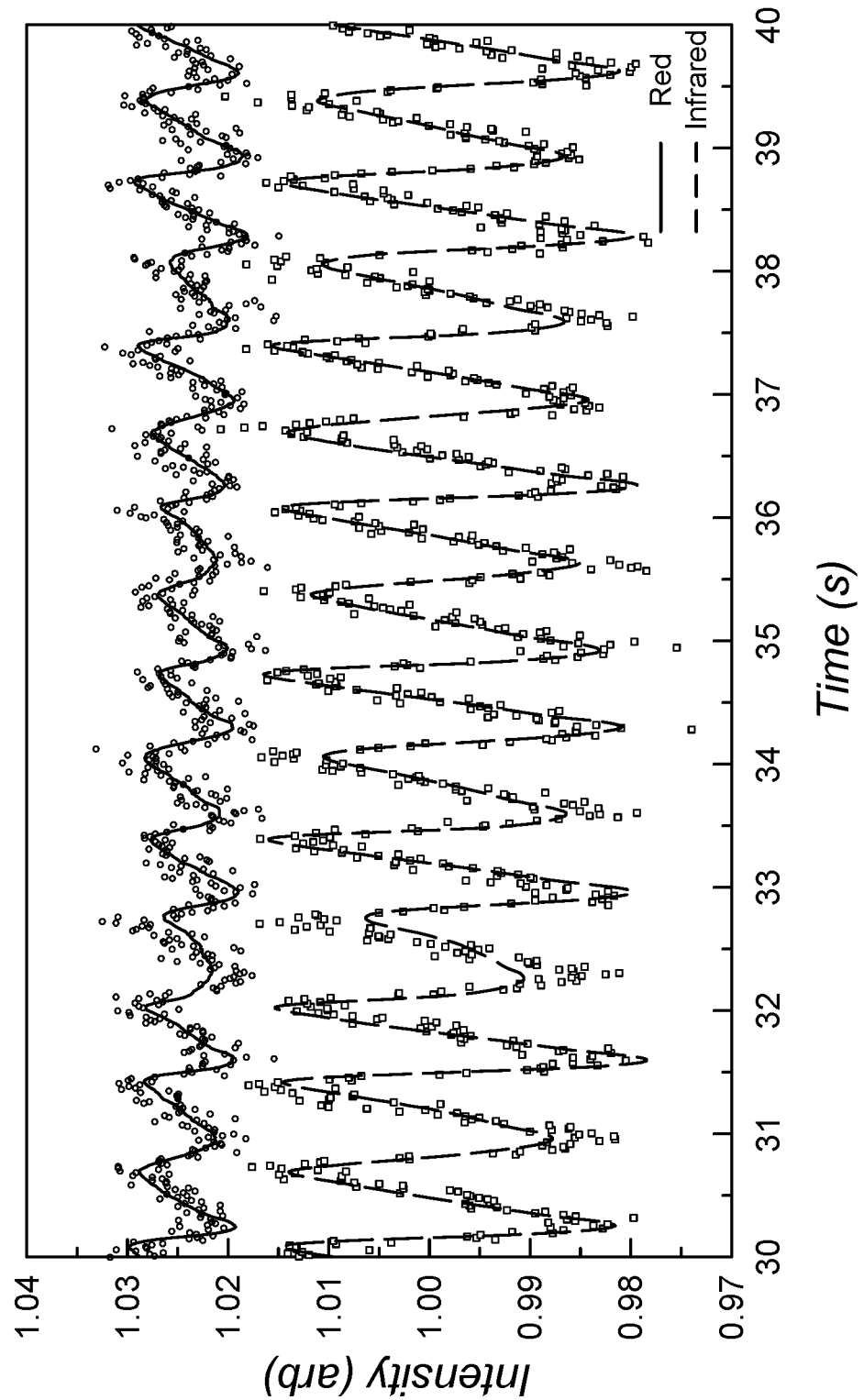
FIG. 10A illustrates input sensor data, FIG. 10A, and FIG. 10B, FIG. 10C, FIG. 10D, and FIG. 10E each illustrate processed output data; from a data processor configured to process pulse oximetry data under a low blood perfusion condition.
Figure 10B:
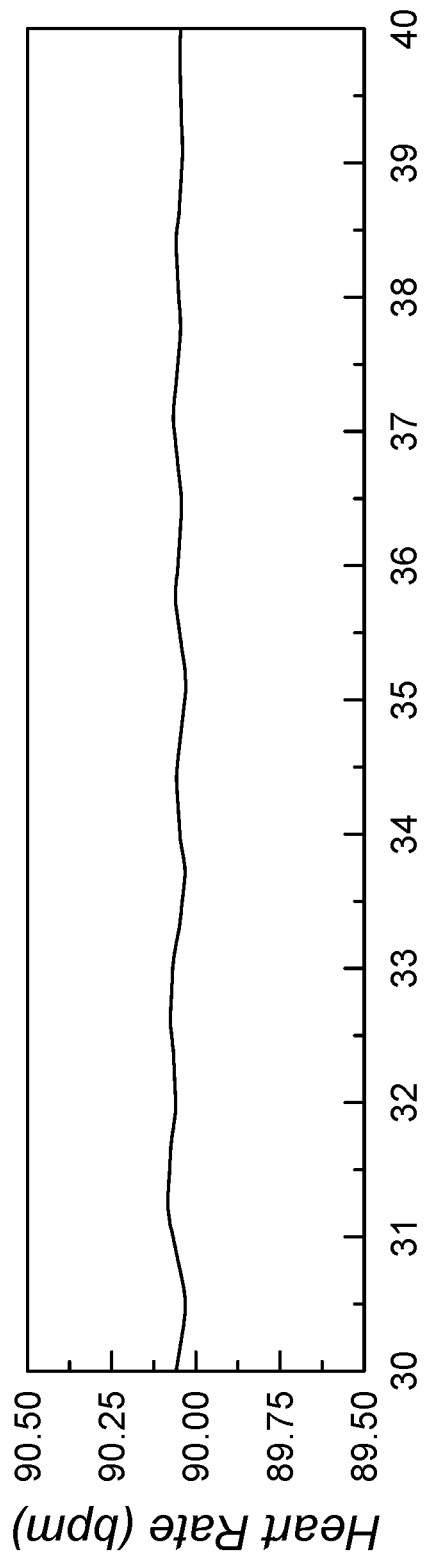
Figure 10C:
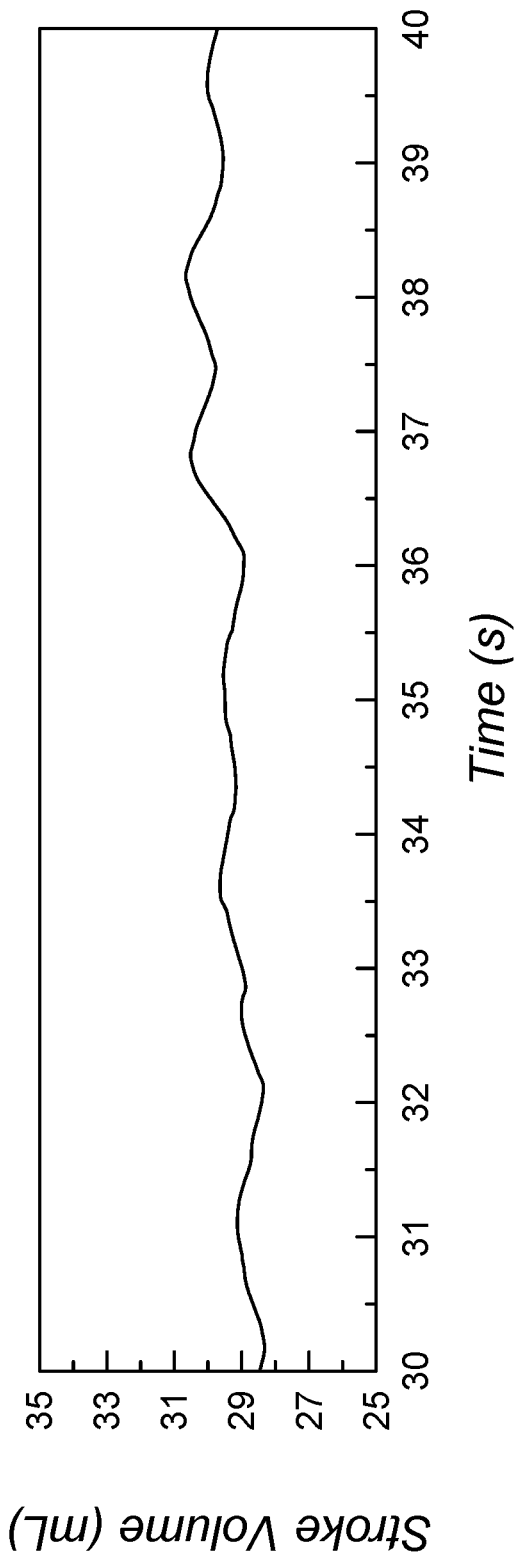
Figure 10D:
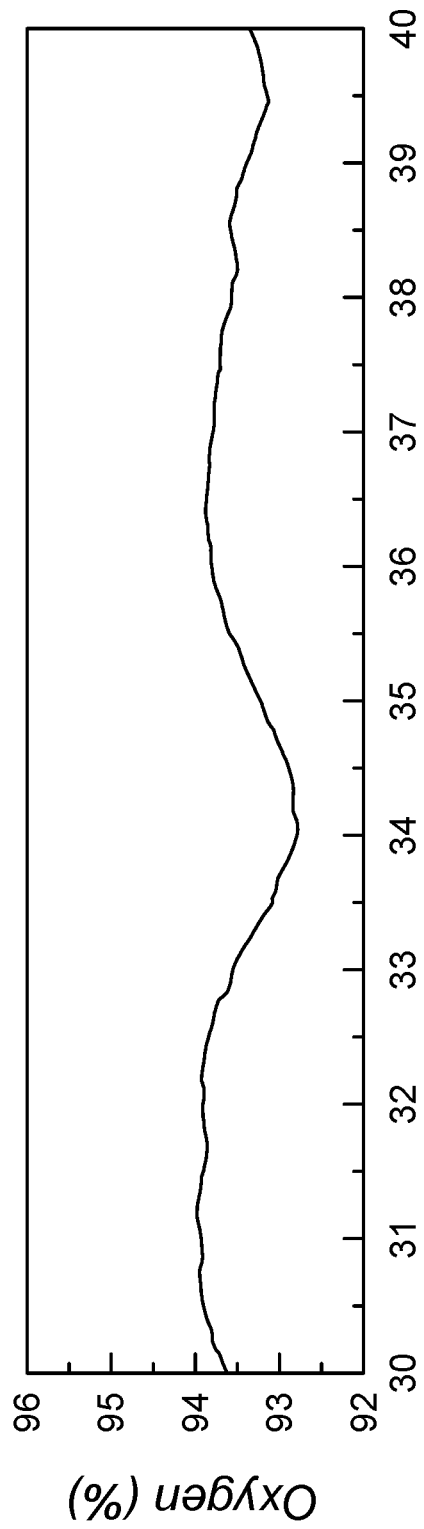
Figure 10E:
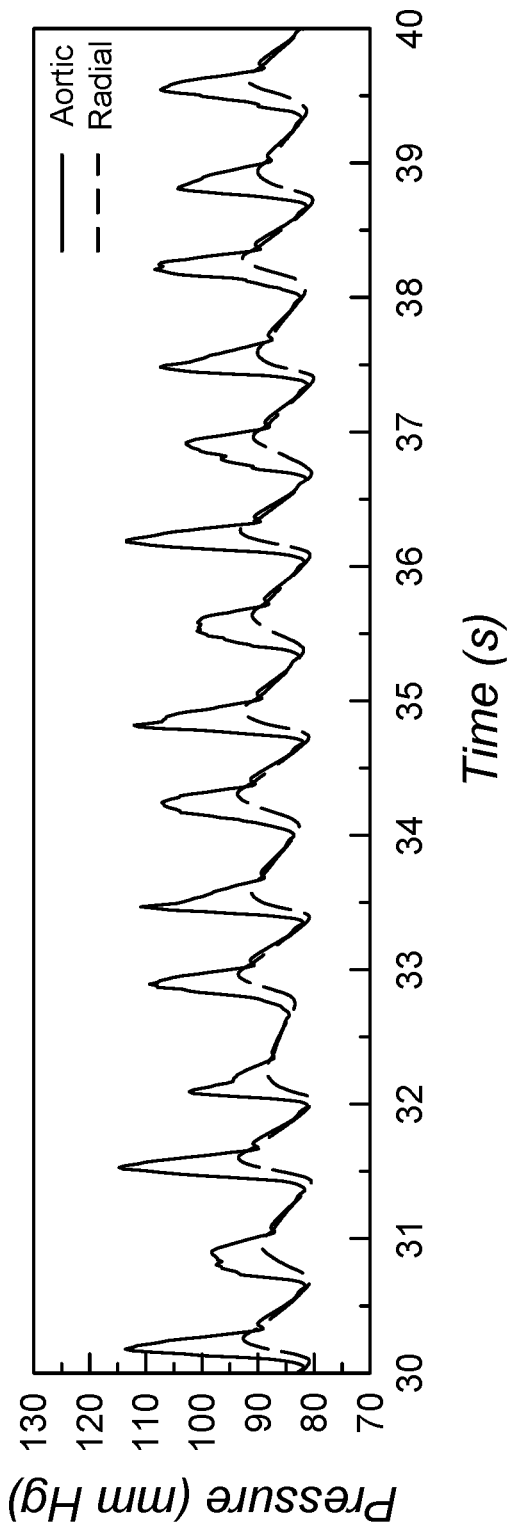

A second stretch of photoplethysmographic waveforms are provided that represent a low signal-to-noise ratio signal from a pulse oximeter. Low signal-to-noise photoplethysmographic waveforms (FIG. 10A) were used to extract heart rate (FIG. 10B), left-ventricular stroke volume (FIG. 10C), blood oxygen saturation (FIG. 10D), and aortic and systemic (radial) pressure waveforms (FIG. 10E) using the hemodynamics dynamic state-space model 805. In each case, the use of the probabilistic digital signal processor 200 configured with the optional sensor dynamics and noise model 822 and spectrometer signal transduction model 824 overcame the noisy input stream to yield smooth and functional output data for medical use.

The various models relate measurement parameters from a source medical device to a second parameter not measured by the source medical device. For example, an oxygen level is related to a heart stroke volume.

Electrocardiography

Electrocardiography is a noninvasive transthoracic interpretation of the electrical activity of the heart over time as measured by externally positioned skin electrodes. An electrocardiographic device produces an electrocardiogram (ECG or EKG).

The electrocardiographic device operates by detecting and amplifying the electrical changes on the skin that are caused when the heart muscle depolarizes, such as during each heartbeat. At rest, each heart muscle cell has a charge across its outer wall or cell membrane. Reducing the charge toward zero is called de-polarization, which activates the mechanisms in the cell that cause it to contract. During each heartbeat a healthy heart will has orderly progression of a wave of depolarization that is triggered by the cells in the sinoatrial node, spreads out through the atrium, passes through intrinsic conduction pathways, and then spreads all over the ventricles. The conduction is detected as increases and decreases in the voltage between two electrodes placed on either side of the heart. The resulting signal is interpreted in terms of heart health, function, and/or weakness in defined locations of the heart muscles.

Examples of electrocardiograph device lead locations and abbreviations include:

right arm (RA);
left arm (LA);
right leg (RL);
left leg (LL);
in fourth intercostal space to right of sternum ($V_1$);
in fourth intercostal space to left of the sternum ($V_2$);
between leads $V_2$ and $V_4$ ($V_3$);
in the fifth intercostal space in the mid clavicular line ($V_4$);
horizontally even with $V_4$, but in the anterior axillary line ($V_5$); and
horizontally even with $V_4$ and $V_5$ in the midaxillary line ($V_6$).

Usually more than two electrodes are used and they are optionally combined into a number of pairs. For example, electrodes placed at the left arm, right arm, and left leg form the pairs LA+RA, LA+LL, and RA+LL. The output from each pair is known as a lead. Each lead examines the heart from a different angle. Different types of ECGs can be referred to by the number of leads that are recorded, for example 3-lead, 5-lead, or 12-lead ECGs.

Electrocardiograms are used to measure and diagnose abnormal rhythms of the heart, such as abnormal rhythms caused by damage to the conductive tissue that carries electrical signals or abnormal rhythms caused by electrolyte imbalances. In a myocardial infarction (MI) or heart attack, the electrocardiogram is used to identify if the heart muscle has been damaged in specific areas. Notably, traditionally an ECG cannot reliably measure the pumping ability of the heart, for which additional tests are used, such as ultrasound-based echocardiography or nuclear medicine tests. Along with other uses of an electrocardiograph model, the probabilistic mathematical electrocardiograph model, described infra, shows how this limitation is overcome.

Example II

A second example of a dynamic state-space model 210 coupled with a dual or joint estimator 222 and/or a probabilistic updater 220 or probabilistic sampler 230 in a medical or biomedical application is provided.

Ischemia and Heart Attack

For clarity, a non-limiting example of prediction of ischemia using an electrocardiograph dynamic state-space model is provided. A normal heart has stationary and homogenous myocardial conducting pathways. Further, a normal heart has stable excitation thresholds resulting in consecutive beats that retrace with good fidelity. In an ischemic heart, conductance bifurcations and irregular thresholds give rise to discontinuous electrophysiological characteristics. These abnormalities have subtle manifestations in the electrocardiograph morphology that persist long before shape of the electrocardiograph deteriorates sufficiently to reach detection by a skilled human operator. Ischemic abnormalities are characterized dynamically by non-stationary variability between heart beats, which are difficult to detect, especially when masked by high frequency noise, or similarly non-stationary artifact noise, such as electrode lead perturbations induced by patient motion.

Detection performance is improved substantially relative to the best practitioners and current state-of-the-art algorithms by integrating a mathematical model of the heart with accurate and rigorous handling of probabilities. An example of an algorithm for real time and near-optimal ECG processing is the combination of a sequential Monte Carlo algorithm with Bayes rule. Generally, an electrodynamic mathematical model of the heart with wave propagation through the body is used to provide a "ground truth" for the measured signal from the electrocardiograph electrode leads. Use of a sequential Monte Carlo algorithm predicts a multiplicity of candidate values for the signal, as well as other health states, at each time point, and each is used as a prior to calculate the truth estimate based on sensor input via a Bayesian update rule. Since the model is electrodynamic and contains state and model parameter variables corresponding to a normal condition and an ischemic condition, such events can be discriminated by the electrocardiograph model, described infra.

Unlike simple filters and algorithms, the electrocardiograph dynamic state-space model coupled with the probabilistic updater 220 or probabilistic sampler 230 is operable without the use of assumptions about the regularity of morphological variation, spectra of noise or artifact, or the linearity of the heart electrodynamic system. Instead, the dynamic response of the normal or ischemic heart arises naturally in the context of the model during the measurement process. The accurate and rigorous handling of probabilities of this algorithm allows the lowest possible detection limit and false positive alarm rate at any level of noise and/or artifact corruption.

Electrocardiograph with Probabilistic Data Processing

Figure 11:
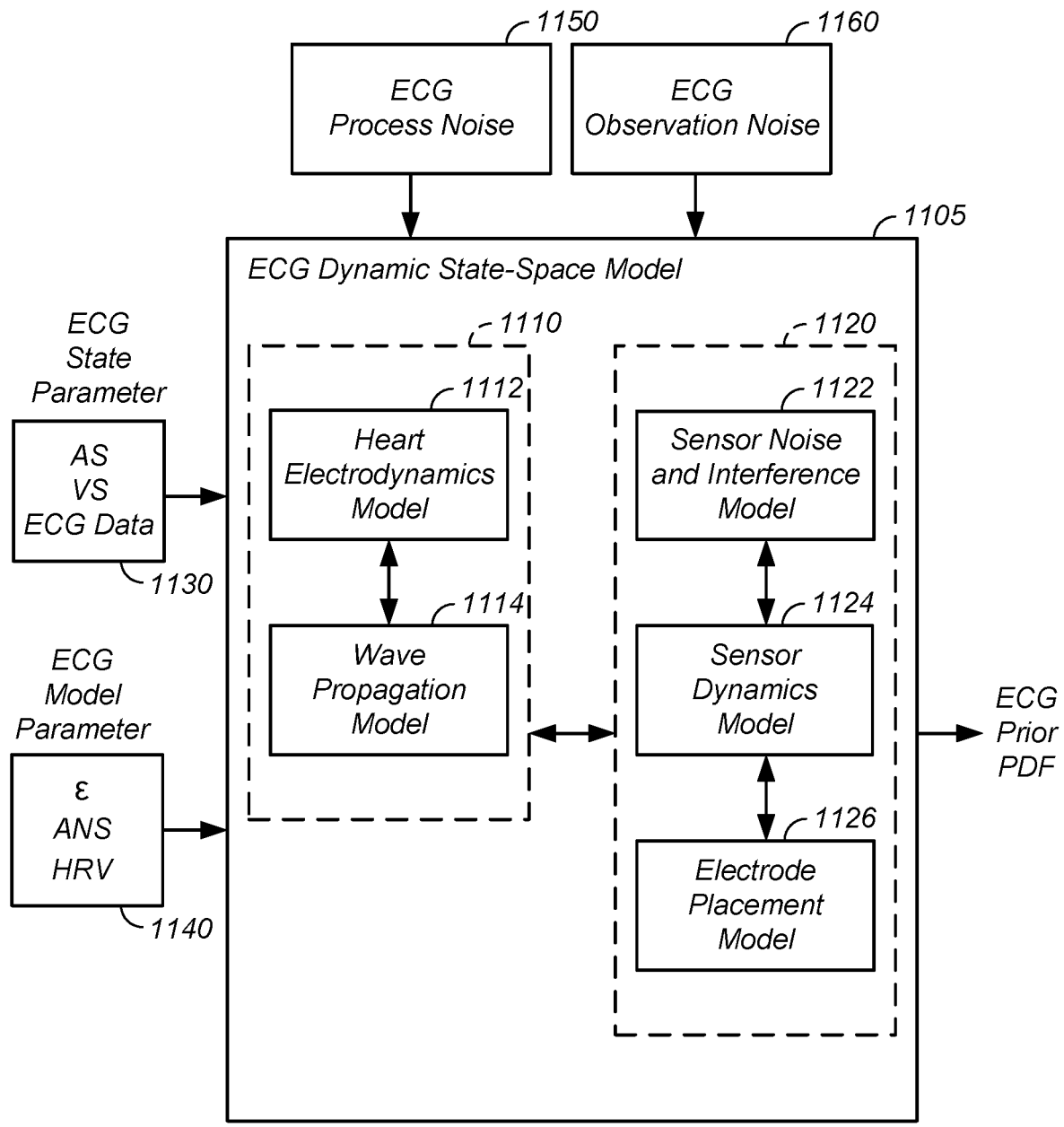
FIG. 11 is a flow chart showing the components of a electrocardiograph dynamic state-space model.

FIG. 11 is a schematic of an electrocardiograph dynamic state-space model suitable for processing electrocardiogram data, including components required to describe the processes occurring in a subject. The combination of SPKF or SMC filtering in state, joint, or dual estimation modes is optionally used to filter electrocardiograph (ECG) data. Any physiology model adequately describing the ECG signal is optionally used, as well as any model of noise and artifact sources interfering or contaminating the signal. One non-limiting example of such a model is a model using a sum of arbitrary wave functions with amplitude, center and width, respectively, for each wave (P, Q, R, S, T) in an ECG. The observation model comprises the state plus additive Gaussian noise, but more realistic pink noise or any other noise probability distributions is optionally used.

Still referring to FIG. 11, to facilitate description of the electrocardiograph dynamic state-space model 1105, a non-limiting example is provided. In this example, the electrocardiograph dynamic state-space model 1105 is further described. The electrocardiograph dynamic state-space model 1105 preferably includes a heart electrodynamics model 1110 corresponding to the dynamic state-space model 210 process model 710. Further, the electrocardiograph dynamic state-space model 1105 preferably includes a heart electrodynamics observation model 1120 corresponding to the dynamic state-space model 210 observation model 720. The electrocardiograph process model 1110 and electrocardiogram observation model 1120 are further described, infra.

Still referring to FIG. 11, the electrocardiograph process model 1110 optionally includes one or more of a heart electrodynamics model 1112 and a wave propagation model 1114. The heart electrodynamics model 1112 is a physics based model of the electrical output of the heart. The wave propagation model 1114 is a physics based model of movement of the electrical pulses through the lungs, fat, muscle, and skin. An example of a wave propagation model 1114 is a thorax wave propagation model modeling electrical wave movement in the chest, such as through an organ. The various models optionally share information. For example, the electrical pulse of the heart electrodynamics model 1112 is optionally an input to the wave propagation model 1114, such as related to one or more multi-lead ECG signals. Generally, the process model 710 components are optionally probabilistic, but are preferentially deterministic. Generally, the observation model 720 components are probabilistic.

Still referring to FIG. 11, the electrocardiogram observation model 1120 optionally includes one or more of a sensor noise and interference model 1122, a sensor dynamics model 1124, and/or an electrode placement model 1126. Each of the sensor noise and interference model 1122 and the sensor dynamics models 1124 are optionally physics based probabilistic models related to noises associated with the instrumentation used to collect data, environmental influences on the collected data, and/or noise due to the human interaction with the instrumentation, such as movement of the sensor. A physics based model uses at least one equation relating forces, electric fields, pressures, or light intensity to sensor provided data. The electrode placement model 1126 relates to placement of the electrocardiograph leads on the body, such as on the arm, leg, or chest. As with the electrocardiograph process model 1110, the sub-models of the electrocardiograph observation model 1120 optionally share information. For instance, a first source of noise, such as sensor noise related to movement of the sensor, is added to a second source of noise, such as a signal transduction noise.

Optionally and preferably, the electrocardiograph observation model 1120 shares information with and/provides information to the electrocardiograph process model 1110.

The electrocardiograph dynamic state-space model 1105 receives inputs, such as one or more of:
electrocardiograph state parameters 1130;
electrocardiograph model parameters 1140;
electrocardiograph process noise 1150; and
electrocardiograph observation noise 1160.

Examples of electrocardiograph state parameters 1130, corresponding to state parameters 730, include: atrium signals (AS), ventricle signals (VS) and/or ECG lead data. Examples of electrocardiograph model parameters 1140, corresponding to the more generic model parameters 740, include: permittivity, c, autonomic nervous system (ANS) tone or visceral nervous system, and a heart rate variability (HRV). Heart rate variability (HRV) is a physiological phenomenon where the time interval between heart beats varies and is measured by the variation in the beat-to-beat interval. Heart rate variability is also referred to as heart period variability, cycle length variability, and RR variability, where R is a point corresponding to the peak of the QRS complex of the electrocardiogram wave and RR is the interval between successive Rs. In this example, the output of the electrocardiograph dynamic state-space model 1105 is a prior probability distribution function with parameters of one or more of the input electrocardiograph state parameters 1130 after operation on by the heart electrodynamics model 1112, a static number, a probability function, and/or a parameter not measured or output by the sensor data.

An example of an electrocardiograph with probabilistic data processing is provided as an example of the electrocardiogram dynamic state-space model 1105. The model is suitable for processing data from an electrocardiograph. In this example, particular equations are used to further describe the electrocardiograph dynamic state-space model 1105, but the equations are illustrative and non-limiting in nature.

Heart Electrodynamics

The heart electrodynamics model 1112 of the ECG dynamic state-space model 1105 is further described. The transmembrane potential wave propagation in the heart is optionally simulated using FitzHugh-Nagumo equations. The heart model 1112 is optionally implemented, for instance, as a coarse-grained three-dimensional heart anatomical model or as a compartmental, zero-dimensional model of the heart. The latter could take the form, for instance, of separate atrium and ventricle compartments.

In a first example of a heart electrodynamics model 1112, a first set of equations for cardiac electrodynamics are provided by equations 22 and 23, $$\dot{u} = div(D\nabla u) + ku(1-u)(u-a) - uz \quad (22)$$

$$\dot{z} = -\left(e + \frac{u_1 z}{u + u_2}\right)(ku(u-a-1) + z) \quad (23)$$

where D is the conductivity, u is a normalized transmembrane potential, and z is a secondary variable for the repolarization. In the compartmental model, $u_i$ becomes either the atrium potential, $u_{as}$, or the ventricle potential, $u_{vs}$. The repolarization is controlled by k and e, while the stimulation threshold and the reaction phenomenon is controlled by the value of a. The parameters $\mu_1$ and $\mu_2$ are preferably empirically fitted.

A second example of a heart electrodynamics model is presented, which those skilled in the art will understand is related to the first heart electrodynamics model. The second heart electrodynamics model is expanded to include a restitution property of cardiac tissue, where restitution refers to a return to an original physical condition, such as after elastic deformation of heart tissue. The second heart electrodynamics model is particularly suited to whole heart modeling and is configured for effectiveness in computer simulations or models.

The second heart electrodynamics model includes two equations, equations 24 and 25, describing fast and slow processes and is useful in adequately representing the shape of heart action potential, $$\frac{\partial u}{\partial t} = \frac{\partial}{\partial x_i} d_{ij} \frac{\partial u}{\partial x_j} - ku(u-a)(u-1) - uv \quad (24)$$

$$\frac{\partial v}{\partial t} = \varepsilon(u,v)(-v - ku(u-a-1)) \quad (25)$$

where $\varepsilon(u,v) = \varepsilon_0 + u_1 v/(u+u_2)$. Herein, the approximate values of $k=8$, $a=0.15$, and $\varepsilon_0 = 0.002$ are used, but the values are optionally set for a particular model. The parameters $u_1$ and $u_2$ are set for a given model and $d_{ij}$ is the conductivity tensor accounting for the heart tissue anisotropy.

Further, the second heart electrodynamics model involves dimensionless variables, such as u, v, and t. The actual transmembrane potential, E, and time, t, are obtained using equations 26 and 27 or equivalent formulas.

$$e[mV] = 100u - 80 \quad (26)$$

$$t[ms] = 12.9t[t.u.] \quad (27)$$

In this particular case, the rest potential $E_{rest}$ is about −80 mV and the amplitude of the pulse is about 100 mV. Time is scaled assuming a duration of the action potential, APD, measured at the level of about ninety percent of repolarization, $APD_0 = 330$ ms. The nonlinear function for the fast variable u optionally has a cubic shape.

The dependence of ε on u and v allows the tuning of the restitution curve to experimentally determined values using $u_1$ and $u_2$. The shape of the restitution curve is approximated by equation 28, $$APD = \frac{CL}{(aCL+b)} \quad (28)$$

where the duration of the action potential, APD, is related to the cycle length, CL. In dimensionless form, equation 28 is rewritten according to equation 29, $$\frac{1}{apd} = 1 + \frac{b}{cl} \quad (29)$$

where $apd = APD/APD_0$, and $APD_0$ denotes APD of a free propagating pulse.

Restitution curves with varying values of parameters $u_1$ and $u_2$ are used, however, optional values for parameters $u_1$ and $u_2$ are about $u_1=0.2$ and $u_2=0.3$. One form of a restitution curve is a plot of apd vs. cl, or an equivalent. Since a restitution plot using apd vs. cl is a curved line, a linear equivalent is typically preferred. For example, restitution curve is well fit by a straight line according to equation 30.

$$\frac{1}{apd} = k_1 + \frac{k_2}{cl} \quad (30)$$

Optional values of $k_1$ and $k_2$ are about 1.0 and 1.05, respectively, but are preferably fit to real data for a particular model. Generally, the parameter $k_2$ is the slope of the line and reflects the restitution at larger values of CL.

The use of the electrodynamics equations, the restitutions, and/or the restitution curve is subsequently used to predict or measure arrhythmia. Homogeneous output is normal. Inhomogeneous output indicates a bifurcation or break in the conductivity of the heart tissue, which has an anisotropic profile, and is indicative of an arrhythmia. Hence, the slope or shape of the restitution curve is used to detect arrhythmia.

Wave Propagation

The electric wave model 1114 of the ECG dynamic state-space model 1105 is further described. The propagation of the heart electrical impulse through lung and other tissues before reaching the sensing electrodes is optionally calculated using Gauss' Law, $$\nabla \cdot E(t) = \frac{u_i(t)}{\varepsilon_0} \quad (31)$$

where $\mu_i(t)$ is the time-varying charge density given by the heart electrodynamics model and $\varepsilon_0$ is the permittivity of free space, which is optionally scaled to an average tissue permittivity.

Sensor Dynamics

The sensor dynamics model 1124 of the ECG dynamic state-space model 1105 is further described. The ECG sensor is an electrode that is usually interfaced by a conducting gel to the skin. When done correctly, there is little impedance from the interface and the wave propagates toward a voltage readout. The overall effect of ancillary electronics on the measurement should be small. The relationship between the wave and readout can be written in general as:

$$V(t) = G(E(t)) + N(p) + D(s,c) \quad (32)$$

where G is the map from the electrical field reaching the electrode and voltage readout. This includes the effect of electronics and electrode response timescales, where N is the sensor noise and interference model and D is the electrode placement model.

Sensor Noise and Interference Model

The sensor noise and interference model 1122 of the ECG dynamic state-space model 1105 is further described. The sensor noise enters the DSSM as a stochastic term (Langevin) that is typically additive but with a PDF that is both non-Gaussian and non-stationary. Optionally non-stationarity is modeled from the perturbation, p, representing both external interference and cross-talk. One way to accomplish this is to write:

$$N(E(t),p) = \alpha n_1 + \beta p n_2 \quad (33)$$

where alpha, α, and beta, β, are empirical constants and $n_1$ and $n_2$ are stochastic parameters with a given probability distribution function.

Electrode Placement Model

The electrode placement model 1126 of the ECG dynamic state-space model 1105 is further described. This model is an anatomical correction term to the readout equation operating on the sagittal and coronal coordinates, s and c, respectively. This model varies significantly based on distance to the heart and anatomical structures between the heart and sensor. For instance, the right arm placement is vastly different than the fourth intercostal.

Optionally, the output from the electrocardiograph probabilistic model is an updated, error filtered, or smoothed version of the original input data. For example, the probabilistic processor uses a physical model where the output of the model processes low signal-to-noise ratio events to yield any of: an arrhythmia detection, arrhythmia monitoring, an early arrhythmia warning, an ischemia warning, and/or a heart attack prediction.

Optionally, the model compares shape of the ECG with a reference look-up table, uses an intelligent system, and/or uses an expert system to estimate, predict, or produce one or more of: an arrhythmia detection, an ischemia warning, and/or a heart attack warning.

Figure 12A:
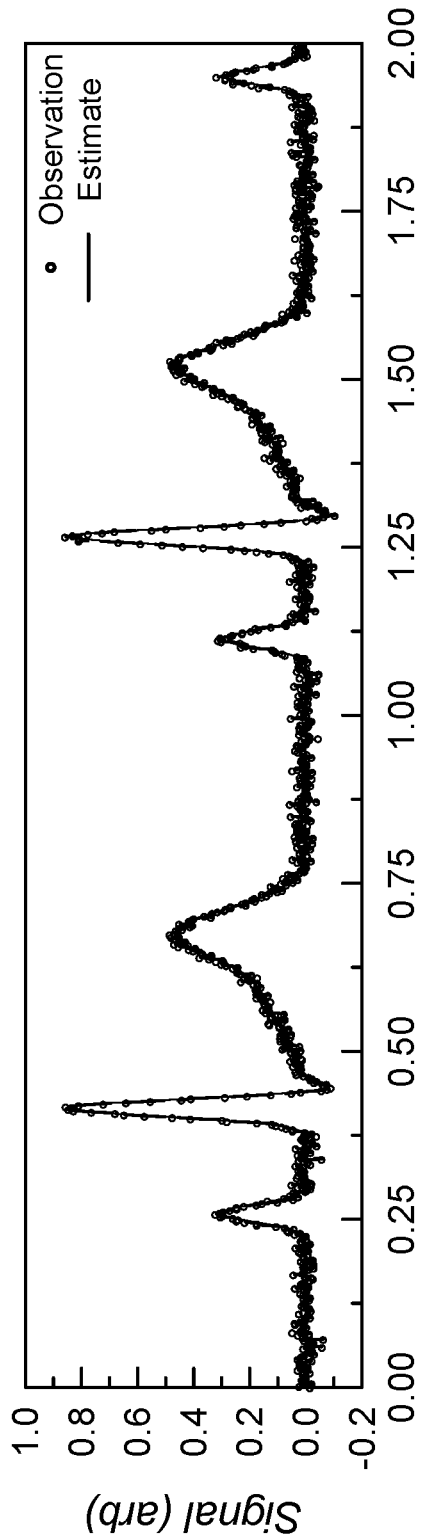
FIG. 12A illustrates noisy non-stationary ECG sensor data input and FIG. 12B illustrates processed heart rate and ECG output.
Figure 12B:
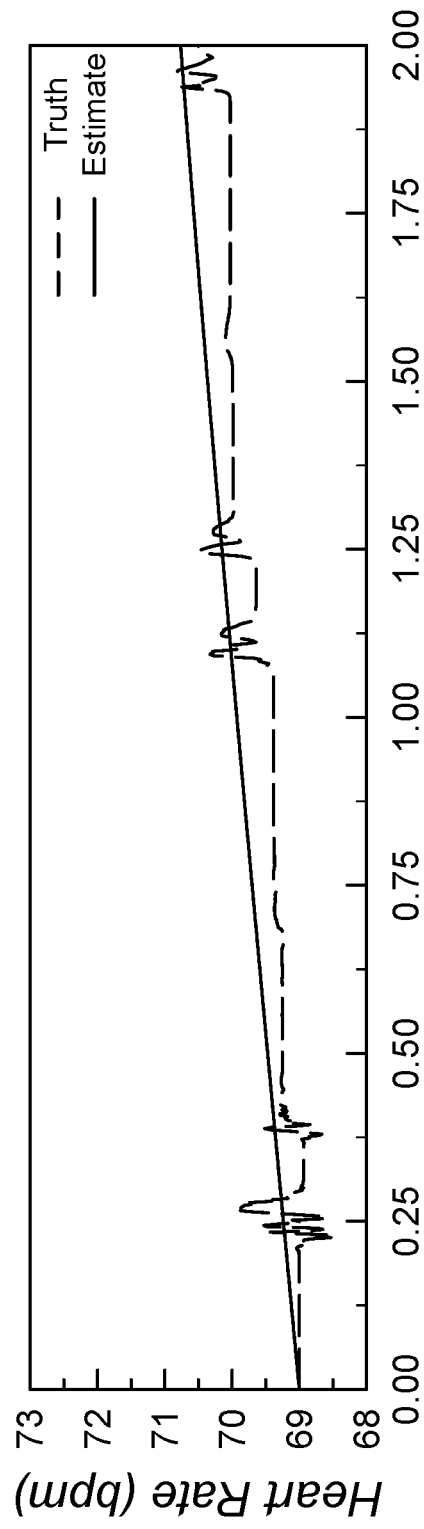
Figure 13A:
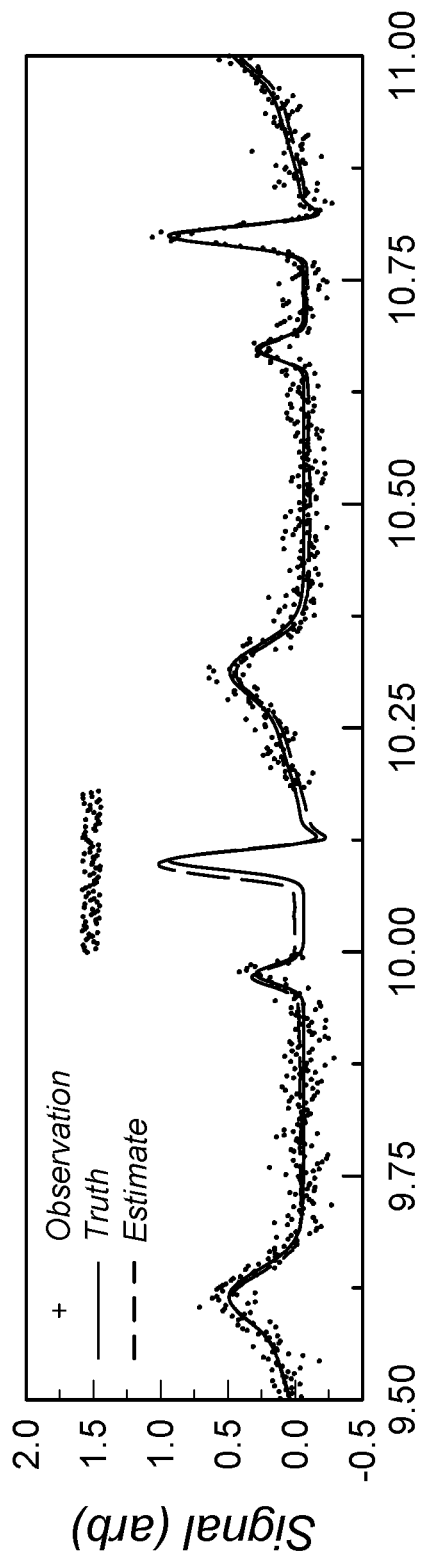
FIG. 13A and FIG. 13B are charts showing input ECG sensor data and comparing output data from a data processor according to the present invention with output data generating using a Savitzky-Golay FIR data processing algorithm.
Figure 13B:
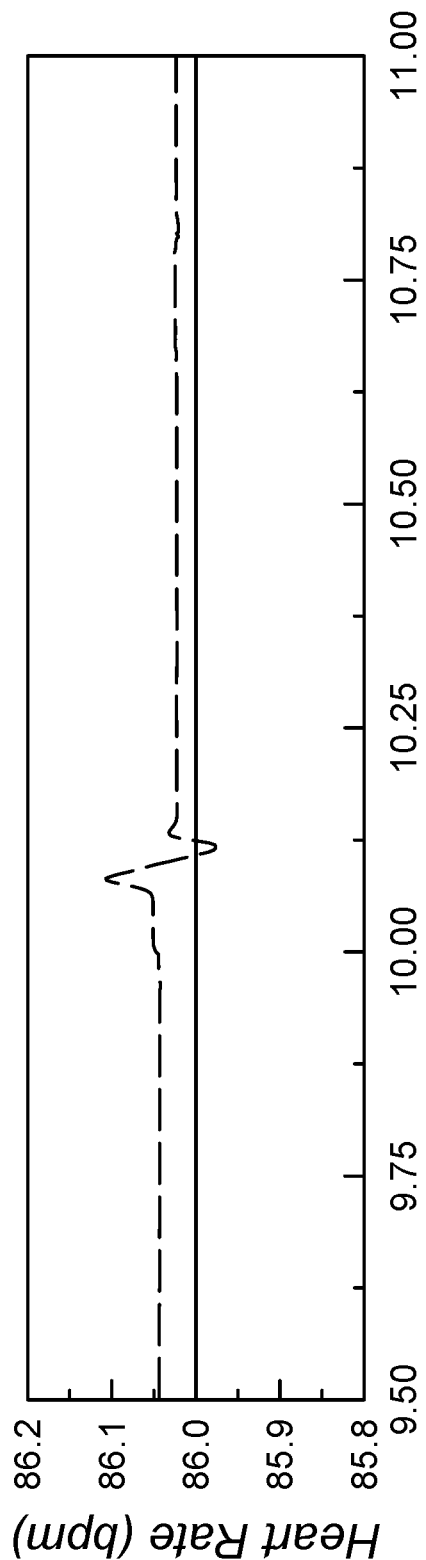

Referring now to FIG. 12A and FIG. 12B, the results of processing noisy non-stationary ECG signals are shown. Heart rate oscillations representative of normal respiratory sinus arrhythmia are present in the ECG. The processor accomplishes accurate, simultaneous estimation of the true ECG signal and a heart rate that follows closely the true values. Referring now to FIG. 13A and FIG. 13B, the performance of the processor using a noise and artifact-corrupted signal is shown. A clean ECG signal representing one heart beat was contaminated with additive noise and an artifact in the form of a plateau at R and S peaks (beginning at time=10 sec). Estimates by the processor remain close to the true signal despite the noise and artifact.

Fusion Model

Optionally, inputs from multiple data sources, such as sensors or medical instruments, are fused and used in the probabilistic digital signal processor 200.

The fused data often include partially overlapping information, which is shared between models, used in a fused model, and/or is used in a global model to enhance parameter estimation. The overlapping information results in benefits of the fused model, including:

enhanced accuracy of an estimated parameter;
enhanced precision of an estimated parameter;
noise artifact reduction in a data stream; and/or
an additionally determined metric.

Herein, fusion of data from biomedical sensors is used to illustrate the benefits of sensors fusion in combination with a physical model. However, the concept extends to cover mechanical systems using sensors.

Data Fusion

Figure 14:
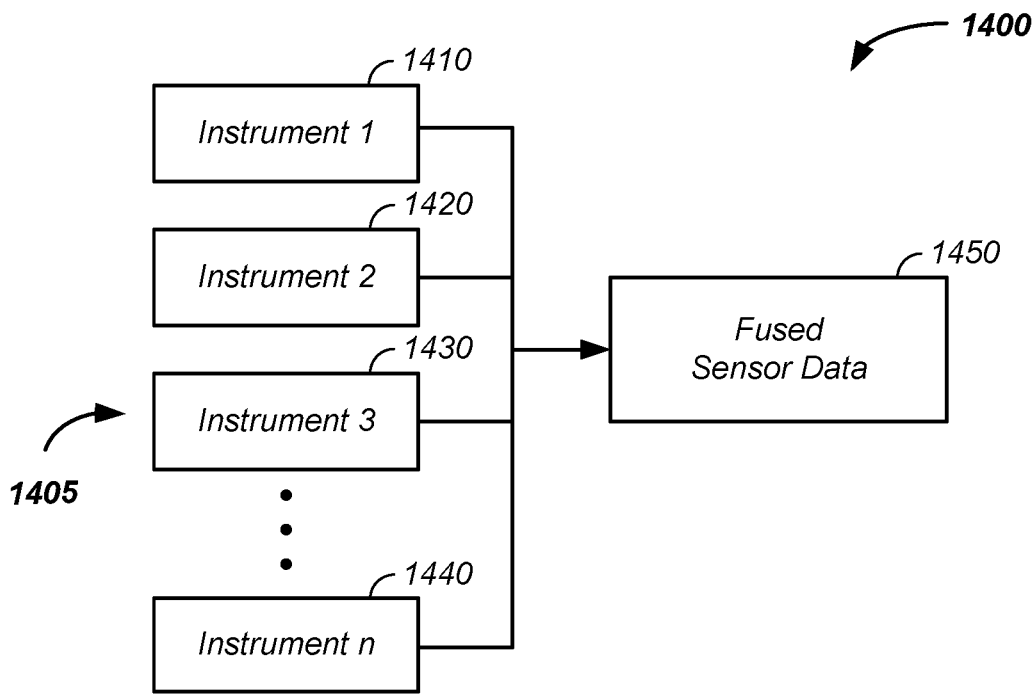
FIG. 14 illustrates fusion of data from multiple instruments.

Referring now to FIG. 14, an overview of a sensor fusion system 1400 in combination with at least one physical model and a probabilistic processor 200 is provided. Generally, data from multiple instruments 1405 is provided to the probabilistic processor 200, such as to the probabilistic updater 220, dual or joint estimator 222, state parameter updater 224, and/or the model parameter updater 226. More particularly, data from a first instrument 1410, second instrument 1420, third instrument 1430, and/or $n^{th}$ instrument 1440 is provided to the probabilistic processor 200, where n is a positive integer, such as at least 2, 3, 4, or 5. One or more of the n instruments 1405 optionally include readings from multiple sensors. As a first example, if the first instrument 1410 is a pulse oximeter, then output from the pulse oximeter as input to the probabilistic processor 200 optionally includes one or more of: raw sensor data, voltage data, processed spectral intensity data, or pulse oximeter generated output data, such as a blood oxygen saturation percentage. As a second example, if the second instrument 1420 is an electrocardiograph device, then output from the electrocardiograph device as input to the probabilistic processor 200 optionally includes one or more of: raw sensor data, current, voltage, resistance, processed electrocardiograph device signal, and/or an outcome, such as an indication of a previous heart attack. In a third example, output from an instrument includes environmental information, such as temperature, pressure, vibration, and humidity. Herein, time readings are optionally input along with any of the sensor data from any of the multiple instruments 1405, but time is not considered a sensed value nor does time count as one of the multiple data sources fused with the probabilistic processor 200. The fused sensor data 1450 refers to any form, matrix, concatenation, combination, union, representation, or mathematical combination of the data from the multiple instruments 1405. The fused sensor data 1450 is preferably fused by use of the probabilistic processor 200 but is optionally fused prior to input into the probabilistic processor 200.

Figure 15:
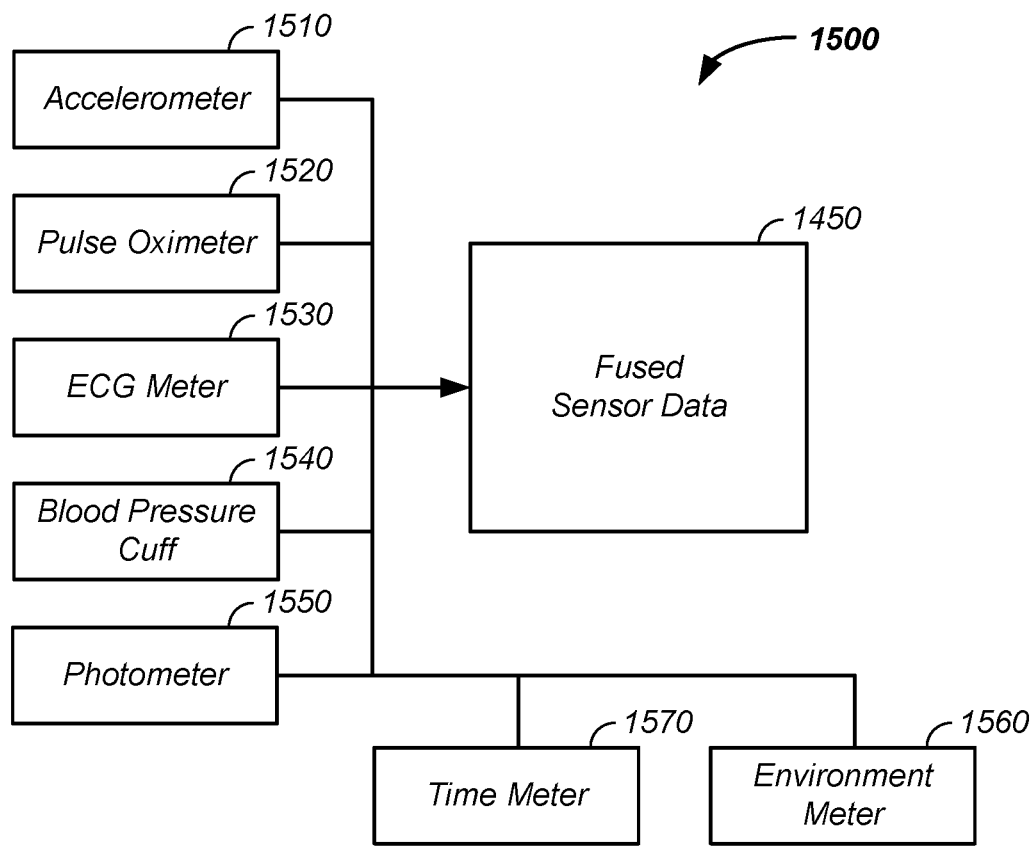
FIG. 15 illustrates fusion of biomedical data, accelerometer data, and/or environmental data.

Referring now to FIG. 15, an example of a pulse oximeter 1520 and an electrocardiograph meter or device 1530 used as inputs to the probabilistic processor 200 is provided. The pulse oximeter 1520 provides time dependent values to the probabilistic processor 200, such as raw sensor data, voltage data, processed spectral intensity data, or pulse oximeter generated output data, such as a blood oxygen saturation percentage. The electrocardiograph meter 1530 additionally provides time dependent values to the probabilistic processor 200, such as raw sensor data, current, voltage, resistance, processed electrocardiograph device signal, and/or an outcome, such as a previous heart attack indication. The pulse oximeter 1520 data and electrocardiograph device output, such as from an ECG meter 1530 or electrocardiograph meter, are optionally fused, as described supra. As discussed, infra, additional input data is provided to the probabilistic processor 200, such as data from an accelerometer 1510, blood pressure cuff 1540, data from a photometer 1550, such as a spectrometer, time meter 1560, data from an environment meter 1570, such as temperature, pressure, vibration, humidity, and/or position information, and/or data from the user. The data is at least partially fused into fused sensor data 1450, as described supra.

Integration of Fused Data with Probabilistic Processor

Figure 16:
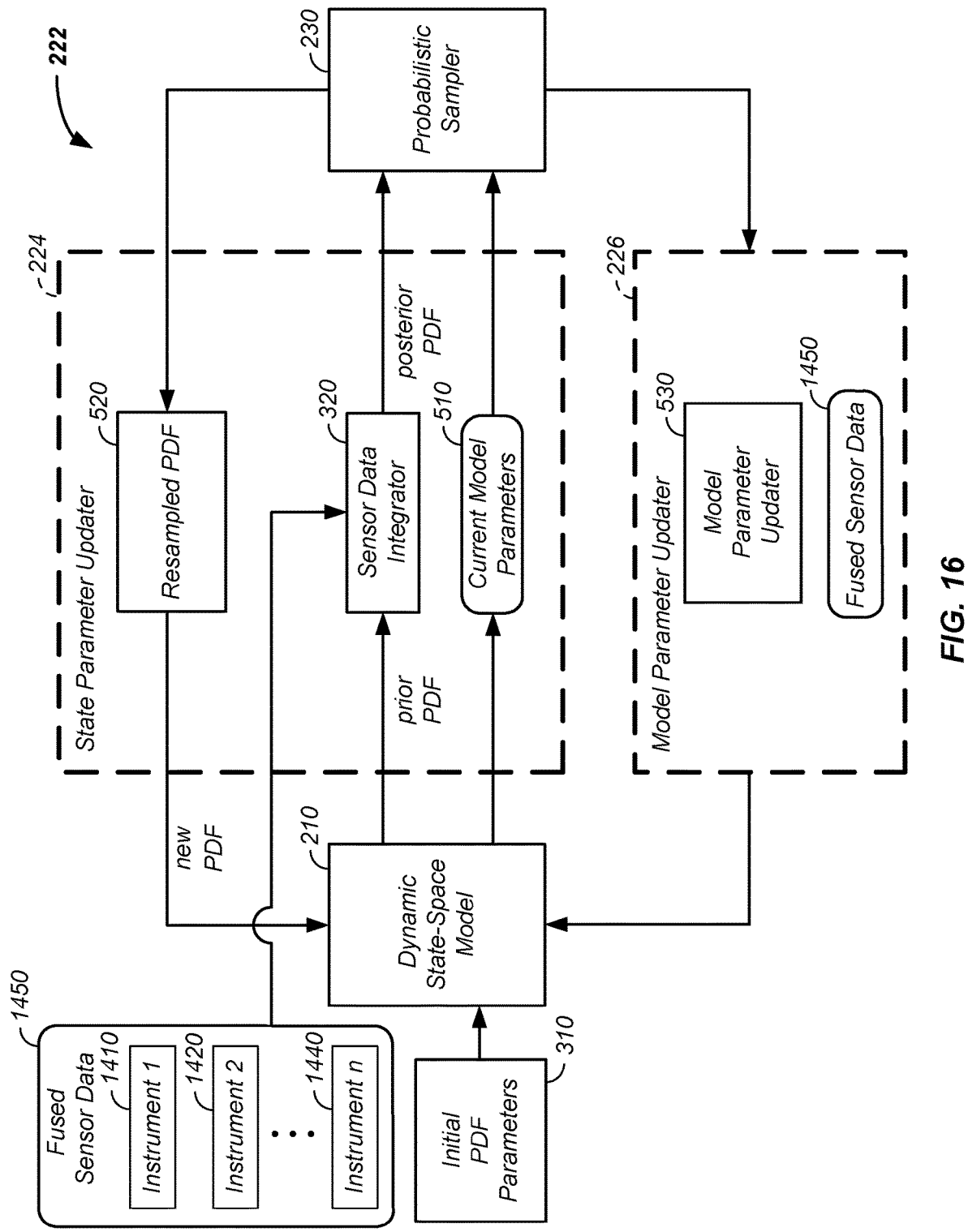
FIG. 16 shows integration of multiple data streams into a joint processor.

Referring now to FIG. 16, an example of data originating from the multiple instruments 1405 as input to the dual or joint estimator 222 is provided. As illustrated, the data from the multiple instruments 1405, described supra, is optionally input into the state parameter updater 224 or into the model parameter updater 226. As described, supra, the data from the multiple instruments 1405 is optionally fused prior to and/or after entry into any of the probabilistic processor 200 sub-components or software algorithms. Similarly, the initial probability distribution function parameters 310 optionally include initial values/probabilities for each of the multiple instruments 1405.

Fusion Configured Dynamic State-Space Model

Figure 17:
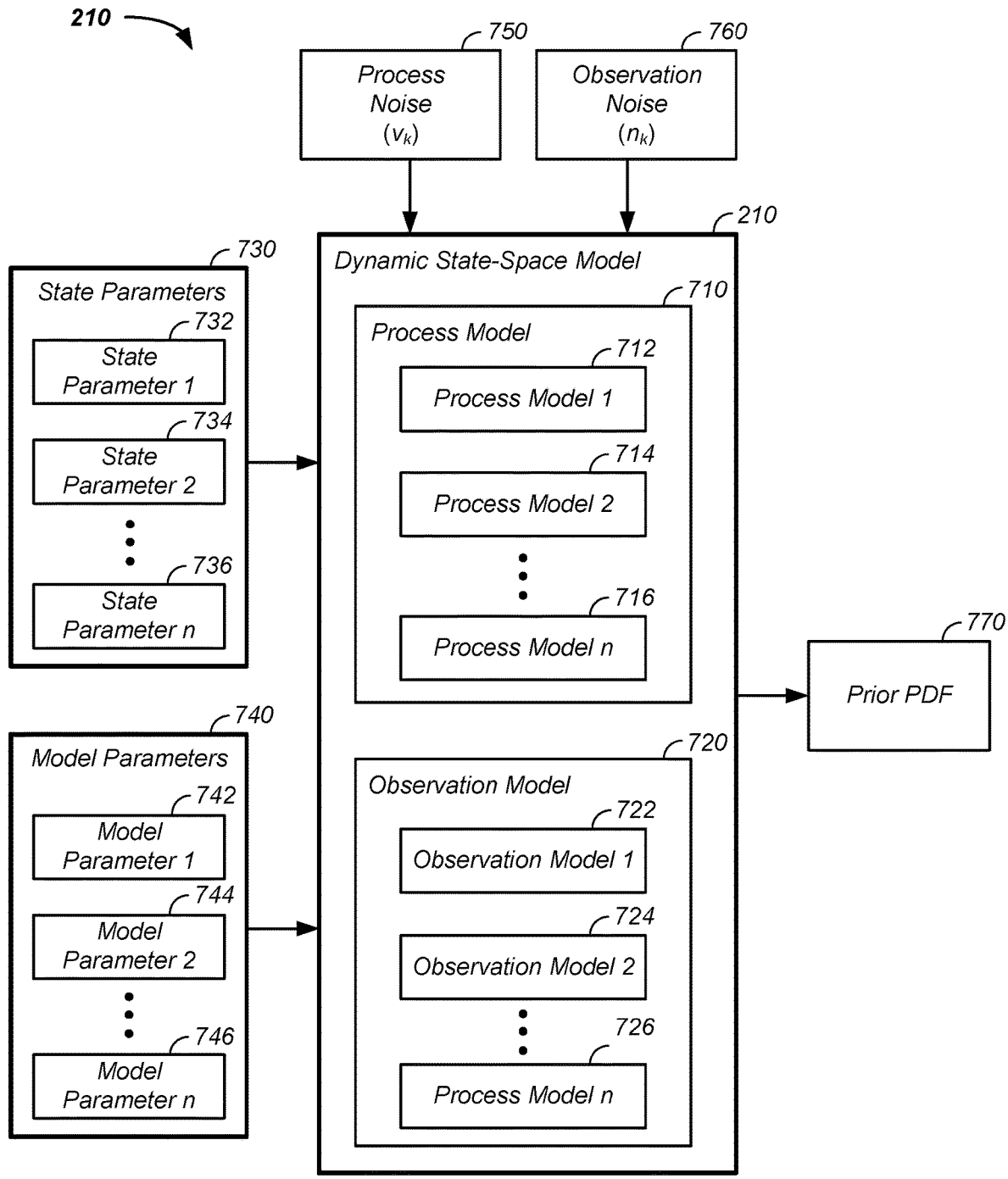
FIG. 17 illustrates a fusion dynamic state-space model.

Referring now to FIG. 17, an example of a dynamic state-space model 210 configured for use with data from the multiple instruments 1405 is provided.

Process Model

For example, the process model 710 of the dynamic state-space model 210, optionally includes a first process model 712 related to data from the first instrument 1410 and a second process model 714 configured to use and represent data from the second instrument 1420. Generally, there are about n process models 716 related to the n instruments 1440, though 1, 2, 3, or more process models are optionally configured to represent or process the data from the n instruments.

Observation Model

Similarly, the observation model 720 of the dynamic state-space model 210, optionally includes a first observation model 722 related to data from the first instrument 1410 and a second observation model 724 configured to use and represent data from the second instrument 1420. Generally, there are about n observation models 716 related to the n instruments 1440, though 1, 2, 3, or more observation models are optionally configured to represent or process the data from the n instruments.

State and Model Parameters

The dynamic state-space model optionally receives state parameter 730 inputs. Examples of DSSM inputs include:
- a first state parameter 732, such as a parameter from the first instrument 1410;
- a second state parameter 734, such as a value measured by the second instrument 1420; and
- an $n^{th}$ state parameter 736, such as a parameter determined by the dynamic state-space model 210.

Similarly, the dynamic state-space model 210 optionally receives model parameter 740 inputs. Examples of model parameter inputs include:
- a first model parameter 742, such as a parameter from the first instrument 1410;
- a second model parameter 744, such as a modeled value; and
- an $n^{th}$ state parameter 746, such as a parameter determined by the dynamic state-space model 210.

The dynamic state-space model 210 optionally receives fusion process noise 750 input and/or fusion observation noise 760 input.

Pulse Oximeter/Electrocardiograph Fusion

The non-limiting example of fusion of information from a pulse oximeter and an electrocardiogram device is further described to clarify model fusion and/or information combination.

A pulse oximeter and an electrocardiograph meter both provide information on the heart. Hence, the pulse oximeter and the electrocardiograph meter provide overlapping information, which is optionally shared, such as between the hemodynamics dynamic state-space model 805 and the electrocardiogram dynamic state-space model 1105. Similarly, a fused model incorporating aspects of both the hemodynamics dynamic state-space model 805 and the electrocardiogram dynamic state-space model 1105 is created, which is an example of a fused model. Particularly, in an electrocardiogram the left-ventricular stroke volume is related to the power spent during systolic contraction, which is, in turn, related to the electrical impulse delivered to that region of the heart. Indeed, the R-wave amplitude is optionally correlated to contractility. It is readily seen that other features of the electrocardiogram also have relationships with the cardiac output function. As described, supra, the pulse oximeter also provides information on contractility, such as heart rate, stroke volume, cardiac output flow rate, and/or blood oxygen saturation information. Since information in common is present, the system is over determined, which allows outlier analysis and/or calculation of a heart state or parameter with increased accuracy and/or precision.

Example I

Figure 18:
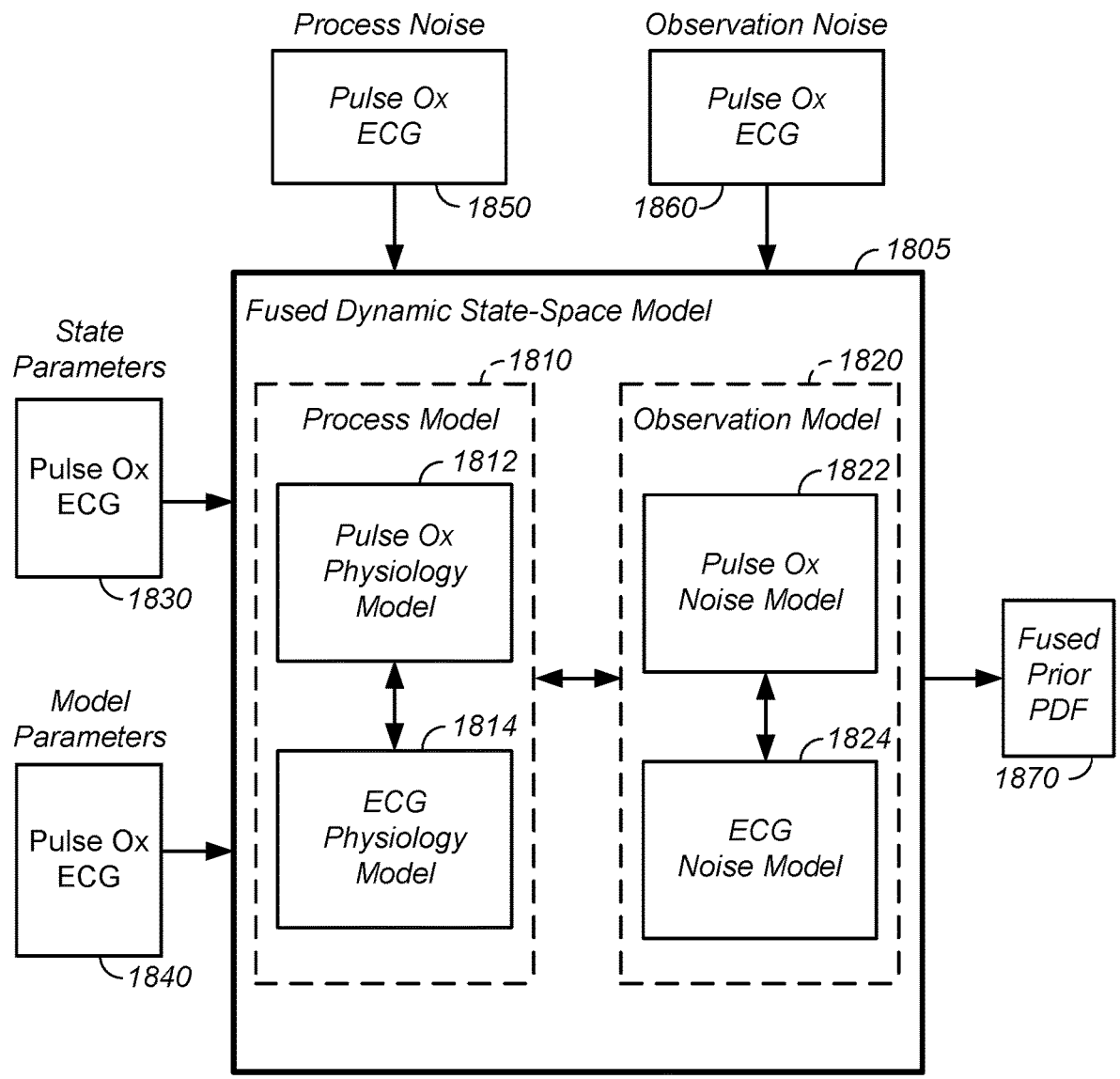
FIG. 18 illustrates combination of medical data streams into a physics based model.

Referring now to FIG. 18, a particular example of a fused dynamic state-space model 1805 is presented. In this example, output from a traditional pulse oximeter 1520 and/or from a photometer 1550, such as a pulse oximeter using at least green light, such as 530±10, 20, or 30 nm, and near-infrared light, such as 960±10, 20, or 30 nm is fused with output from a traditional electrocardiogram device 1530. In this example, the fused dynamic state-space model 1805 incorporates models covering both hemodynamics and heart electrodynamics. Generally, a fused dynamic state-space model 1805 incorporates one or more models modeling information from the multiple instruments 1405.

In this example, a fused process model 1810, of the fused dynamic state-space model 1805, includes one or more of a pulse oximeter physiology process model 1812, the hemodynamics process model 810, an electrocardiograph physiology model 1814, and/or the heart electrodynamics model 1110. For instance, the pulse oximeter physiology process model 1812 optionally incorporates one or more of the hemodynamics heart model 812, the hemodynamics vascular model 814, and/or the light scattering and/or absorbance model 816. Similarly, the electrocardiogram physiology process model 1814 optionally incorporates one or more of the heart electrodynamics model 1112 and/or the wave propagation model 1114.

In this example, a fused observation model 1820, of the fused dynamic state-space model 1805, includes one or more of a pulse oximeter observation noise model 1822, the hemodynamics observation model 820, an electrocardiograph noise model 1824, and/or the electrodynamics observation model 1120. For instance, the pulse oximeter observation noise model 1822 optionally incorporates one or more of the sensor dynamics and noise model 822 and the spectrometer signal transduction noise model 824. Similarly, the electrocardiograph observation noise model 1824 optionally incorporates one or more of the sensor noise and interference model 1122, the sensor dynamics model 1124, and/or the electrode placement model 1126. Any of the process model 1810 sub-models, such as the pulse oximeter physiology model 1812 and electrocardiogram physiology model 1814 share information or data with any of: another process model 1810 sub-model, the process model 1810, the observation model 1820, or any observation model 1820 sub-model, such as the pulse oximeter model 1822 and/or the electrocardiogram noise model 1824.

Generally, in a fused dynamic state-space model, the process model and observation model are optionally combined into a single model or are separate and share information. Further, any sub-model of the process model or sub-model of the observation model shares information or data with any other sub-model of the process model or observation model.

As described, supra, for the dynamic state-space model 210, the fused dynamic state-space model 1805 for the heart optionally receives inputs, including one or more of:
- pulse oximeter and electrocardiograph device state parameters 1830;
- pulse oximeter and electrocardiograph device model parameters 1840;
- pulse oximeter and electrocardiograph device process noise values 1850; and
- pulse oximeter and electrocardiograph device observation noise values 1860.

For example, the pulse oximeter and electrocardiograph device state parameters 1830 optionally include one or more of:
- pulse oximeter related values of:
  - a radial pressure ($P_w$);
  - an aortic pressure ($P_{ao}$);
  - time (t);
  - a spectral intensity (I) or a related absorbance value;
  - a reflectance or reflectance ratio, such as a red reflectance (R r) or an infrared reflectance ($R_{ir}$); and/or a spectral intensity ratio ($I_R$); and
electrocardiograph device related values of:
an atrium signal (AS); and/or
a ventricle signal (VS).

Example II

In another example, the electrocardiograph device observation parameters 1840 optionally include one or more of:
pulse oximeter related values of:
a heart rate (HR);
a stroke volume (SV); and/or
a whole-blood oxygen saturation ($SpO_2$); and
electrocardiograph device related values of:
a permittivity, (c);
an autonomic nervous system (ANS) tone; and/or
a heart rate variability (HRV).

Fusion Benefits

Several non-limiting examples of the benefits of sensor fusion using at least one physiological model and a probabilistic processor 200 are provided.

Stroke Volume and Contractility

In a first case, fused, fusion, or fusing of sensor data from multiple instruments in combination with physical models of body systems yields additional information not present from any given instrument of the multiple instruments 1405. Without loss of generality, an example of generating a measure of stroke volume, a contractility, and/or a heart filling rate using data from a pulse oximeter and an electrocardiograph meter is used to demonstrate the indirect parameter estimation.

Herein, benefits of combining hemodynamic information with electrodynamic information in a fusion model is described. As described, supra, a pulse oximeter plethysmograph in combination with a hemodynamics physical model is used to determine a physical parameter not traditionally achieved from the pulse oximeter, such as a heartbeat stroke volume. Similarly, as described, supra, an electrocardiogram in combination with an electrodynamics physical model is used to determine a physical parameter not traditionally achieved from the electrocardiograph meter, such as contractility. Stroke volume and contractility are related, such as according to equation 34, $$SV \approx FR \cdot C \quad (34)$$

where SV is stroke volume, FR, is the heart filing rate, and C is contractility. Here, the filling rate is determined using information indirectly measured by two systems (SV from the pulse oximeter and C from the ECG). Further, given a known or approximated filling rate, the electrocardiogram determined contractility gives information on the pulse oximeter determined stroke volume, and vise-versa.

In another case, fusing sensor data results in increased information for parameters determined with individual sensor data when the sensed data overlaps in terms of physiology and/or models thereof. For example, as stroke volume is an element of the heart model 812, which is tied to additional hemodynamic models in the hemodynamics dynamic state-space model, such as the vascular model 814, and the stroke volume is related to electrocardiograph data, as described supra, then the electrocardiograph signal optionally aids in determination of parameters directly or indirectly measured by the pulse oximeter and vise-versa. Generally, the electrodynamic signal is related to the hemodynamic signal through the use of one or more models, such as the hemodynamics dynamic state-space model 805, the electrocardiograph dynamic state-space model 1105, or a heart model combining two or more elements of the hemodynamics DSSM model 805 and the electrocardiograph DSSM model 1105.

Arrhythmia

As described, supra, in some systems, such as the heart, hemodynamic information and electrodynamic information are related. As described, supra, the hemodynamic information of stroke volume is related to the electrodynamic information of contractility. Hence, the hemodynamic information of the pulse oximeter yields additional information to any of the parameters measured by the electrocardiogram, such as an arrhythmia. Logically, if the heart is experiencing an arrhythmia, which is being detected by the electrocardiogram probabilistic model, then the heart is experiencing diminished stroke volume, as detected by the pulse oximeter. Hence, the hemodynamic information originating with the pulse oximeter provides supporting or combinatorial information to the electrocardiograph probabilistic model.

Similarly, a blood pressure meter yields information on blood pressure, which is related to heart function. Hence, blood pressure meter information is synergistic with electrocardiograph information and vise-versa. Further, blood pressure meter information is synergistic with hemodynamic, photoplethysmograph, and/or pulse oximeter information and vise-versa Motion Artifact In yet another example, patient movement results in a motion artifact in the sensed data of a given sensor. In many of the observation models 720 of the dynamic state-space model 210, a model is used that relates to sensor movement and/or movement of the body. As a first example, the hemodynamics dynamic state-space model 805 optionally uses the hemodynamics sensor dynamics and noise model 822. As a second example, the electrocardiogram dynamic state-space model 1105 optionally uses the sensor dynamic model 1124. Each of these models relate to movement of the sensor relative to the sensed element, such as the body. Hence, if the body moves, twitches, and/or experiences a bump in transport, such as in transport by an ambulance, the body movement may be detected as a motion artifact with a plurality of sensors. For example, the pulse oximeter and the electrocardiograph device may each detect the same motion artifact. Hence, fusion of the sensed data from multiple instruments allows the identification of an outlier signal or motion artifact signal in data from a first sensor through detection of the same motion artifact with a second sensor. Therefore, identification of a motion artifact with a first sensor is used to remove the same motion artifact from data from a second sensor. Optionally, an accelerometer is used to detect motion artifacts. The fusion of input sensor data from the accelerometer with data streams from one, two, or more additional devices allows removal of the motion artifact data from the one, two, or more additional devices.

Heart Rate Variability

In another example, sensor fusion is used to enhance a measure of heart rate variability. Generally, use of multiple sensors yields: (1) an over-determined system for outlier analysis and/or (2) varying sensor types where not all of the sensors are affected by a noise source. Herein, heart rate variability or variation in beat-to-beat interval of a heart is used to demonstrate each of these cases.

Heart rate variability is measured using a blood pressure meter, a photoplethysmograph derived from a pulse oximeter, or an electrocardiogram device. However, each of the blood pressure meter, pulse oximeter, and electrocardiogram device are subject to noise and/or patient motion artifacts, which result in false positive heartbeats and/or missed heartbeats.

Using a combination of sensors, such as the blood pressure meter, pulse oximeter, and/or electrocardiogram device, results in an over-determined system. The over-determined system allows for outlier analysis. By fusing the signals, an ambiguous signal from the first device is detected and overcome by use of the signal from the second measuring device.

Further, noise sources affecting a first measuring device, such as a pulse oximeter, are often separate from noise sources affecting a second measuring device, such as an electrocardiogram meter. For instance, electrical interference may affect an electrodynamic signal, such as the electrocardiograph, while not impacting a hemodynamic signal, such as a photoplethysmograph. By fusing the signals, noise is recognized in one sensor data stream at a given time as the noise source is not present in the second sensor data stream at the same time due to the noise source type not affecting both sensor types.

Environment Meter

In still yet another case, sensor output from one, two, or more instruments is additionally fused with output from an environmental meter. Herein, an environment meter senses one or more of: temperature, pressure, vibration, humidity, and/or position information, such as from a global positioning system. The environment meter information is used for outlier determination, error correction, calibration, and/or quality control or assurance.

Generally, fusion of signals or sensor data from a plurality of devices allows:
- detection of a false positive or false negative signal from a first device with a second device;
- noise recognized in data from a first sensor type as the noise is not present in a second sensor type;
- fusion of environmental data with medical data;
- determination of an additional parameter not measured or independently measured with individual data types of the fused data;
- electrocardiograph data to aid in analysis of photoplethysmograph data and vise-versa; and/or
- electrodynamic information to aid in analysis of hemodynamic information and vise-versa.

Hardware

The above description describes an apparatus for generation of a physiological estimate of a physiological process of an individual from input data, where the apparatus includes a biomedical monitoring device having a data processor configured to run a dual estimation algorithm, where the biomedical monitoring device is configured to produce the input data and where the input data includes at least one of: a photoplethysmogram and an electrocardiogram. The dual estimation algorithm is configured to use a dynamic state-space model to operate on the input data using both an iterative state estimator and an iterative model parameter estimator in generation of the physiological estimate, where the dynamic state-space model is configured to mathematically represent probabilities of physiological processes that generate the physiological estimate and mathematically represent probabilities of physical processes that affect collection of the input data. Generally, the algorithm is implemented using a data processor, such as in a computer, operable in or in conjunction with a biomedical monitoring device. The method and apparatus are optionally implemented in a rack system in a hospital intensive care unit, such as in connection, combination, and/or alongside other biomedical devices monitoring a patient and connected to a database system, alert station, monitoring station, recording system, nurse station, or a doctor interface.

More generally, the probabilistic digital signal processor is a physical processor, is integrated into a processor, such as in a computer, and/or is integrated into an analyzer. The analyzer is a physical device used to process data, such as sensor data 122. Optionally, the analyzer includes an input device, a power supply, a central processing unit, a memory storage unit, an output display screen, a communication port, and/or a wireless connector, such as Bluetooth. Preferably, the analyzer is integrated with a sensor, such as integrated into any of:
- a pulse oximeter;
- an electrocardiogram device;
- a biomedical device;
- a medical rack system;
- a mechanical sensing system;
- a complex machine;
- a car;
- a plane;
- a fluid monitoring system; and/or
- an oil transport line.

Optionally, the analyzer is configured to receive information from one or more sensors or instruments. Generally, the analyzer is configured for signal processing, filtering data, monitoring a parameter, generating a metric, estimating a parameter value, determining a parameter value, quality control, and/or quality assurance.

In another example, a cardiac stroke volume analyzer comprises a system processor, where the system processor comprises: (1) a probabilistic processor and (2) a dynamic state-space model. The cardiac stroke volume analyzer receives discrete first cardiovascular input data, related to a first sub-system of the biomedical system, from a first blood pressure instrument, such as a pulse oximeter, an electrocardiogram instrument, or a blood pressure analyzer, such as a blood pressure meter with a digital output operating on command, periodically, and/or in a semi-automated mode. The cardiac stroke volume analyzer receives discrete second cardiovascular input data, related to a second sub-system of the biomedical system, from a second electrocardiogram instrument, such as a pulse oximeter, an electrocardiogram instrument, or a blood pressure analyzer. Optionally, the cardiac stroke volume analyzer is an analyzer that, with or without stroke volume analysis, determines contractility or heart filling rate. Optionally and preferably, a system processor, of said cardiac stroke volume analyzer, fuses the first input data and the second input data into fused data, where the system processor comprises: (1) the probabilistic processor converting the fused data into at least two probability distribution functions and (2) at least one probabilistic model, of the dynamic state-space model, operating on the at least two probability distribution functions. Optionally and preferably, the system processor iteratively circulates at least two probability distribution functions in the dynamic state-space model in synchronization with receipt of at least one of: (1) updated first input data and (2) updated second input data. Generally, the system processor processes the probability distribution functions to generate an output related to the state of the biomedical system, such as a left ventricle stroke volume of a heart of a patient, a measure of contractility, and/or a measure of filling rate.

Additional Embodiments

In yet another embodiment, the method, system, and/or apparatus using a probabilistic model to extract physiological information from a biomedical sensor, described supra, optionally uses a sensor providing time-dependent signals. More particularly, pulse ox and ECG examples were provided, supra, to describe the use of the probabilistic model approach. However, the probabilistic model approach is more widely applicable.

The above description describes an apparatus for generation of a physiological estimate of a physiological process of an individual from input data, where the apparatus includes a biomedical monitoring device having a data processor configured to run a dual estimation algorithm, where the biomedical monitoring device is configured to produce the input data, and where the input data comprises at least one of: a photoplethysmogram and an electrocardiogram. The dual estimation algorithm is configured to use a dynamic state-space model to operate on the input data using both an iterative state estimator and an iterative model parameter estimator in generation of the physiological estimate, where the dynamic state-space model is configured to mathematically represent probabilities of physiological processes that generate the physiological estimate and mathematically represent probabilities of physical processes that affect collection of the input data. Generally, the algorithm is implemented using a data processor, such as in a computer, operable in or in conjunction with a biomedical monitoring device.

In yet another embodiment, the method, system, and/or apparatus using a probabilistic model to extract physiological information from a biomedical sensor, described supra, optionally uses a sensor providing time-dependent signals. More particularly, pulse ox and ECG examples were provided, infra, to describe the use of the probabilistic model approach. However, the probabilistic model approach is more widely applicable.

Some examples of physiological sensors used for input into the system with a corresponding physiological model include:

an ECG having about two to twelve leads yielding an ECG waveform used to determine an RR-interval and/or various morphological features related to arrhythmias;

pulse photoplethysmography yielding a PPG waveform for determination of hemoglobins and/or total hemoglobin;

a multi-frequency PPG including multiple wavelengths to measure a variety of gas concentration;

capnography or IR absorption yielding a real time waveform for carbon dioxide determination, end-tidal $CO_2$, an inspired minimum, and/or respiration rate;

a temperature sensor for continuous determination of core body temperature and/or skin temperature;

an anesthetic gas sensor including nitrous oxide, $N_2O$, and carbon dioxide, $CO_2$, used to determine minimum alveolar concentration of an inhaled anesthetic;

a heart catheter yielding a thermodilution curve for determination of a cardiac index and/or a blood temperature;

an impedance cardiography sensor yielding a thoracic electrical bioimpedance reading for determination of thoracic fluid content, accelerated cardiac index, stroke volume, cardiac output, and/or systemic vascular resistance;

a mixed venous oxygen saturation catheter for determination of $SvO_2$;

an electroencephalogram (EEG) yielding an EEG waveform and characteristics thereof, such as spectral edge frequency, mean dominant frequency, peak power frequency, compressed spectral array analysis, color pattern display, and/or delta-theta-alpha-beta band powers, any of which are used for analysis of cardiac functions described herein;

electromyography (EMG) yielding an EMG waveform including frequency measures, event detection, and/or amplitude of contraction;

auscultation yielding sound pressure waveforms;

transcutaneous blood gas sensors for determination of carbon dioxide, $CO_2$, and oxygen, $O_2$;

a pressure cuff yielding a pressure waveform for determination of systolic pressure, diastolic pressure, mean arterial pressure, heart rate, and/or hemodynamics;

spirometry combining capnography and flow waveforms for information on respiratory rate, tidal volume, minute volume, positive end-expiratory pressure, peak inspiratory pressure, dynamic compliance, and/or airway resistance;

fetal and/or maternal sensors, such as ECG and sound (auscultatory) sensors for determination of fetal movement, heart rate, uterine activity, and/or maternal ECG;

laser Doppler flowmetry yielding a velocity waveform for capillary blood flow rate;

an ultrasound and/or Doppler ultrasound yielding a waveform, such as a two-dimensional or three-dimensional image, for imaging and/or analysis of occlusion of blood vessel walls, blood flow velocity profile, and/or other body site dependent measures;

a perspirometer yielding a continuous or semi-continuous surface impedance for information on skin perspiration levels; and/or a digital medical history database to calibrate the model or to screen the database for patient diseases and/or conditions.

Some examples of non-physiological sensors used for input into the system with a corresponding physiological model include:

an accelerometer;

a three axes accelerometer;

a gyroscope;

a compass;

light or a light reading;

a global positioning system, for air pressure data, ambient light, humidity, and/or temperature;

a microphone; and/or an ambient temperature sensor.

While specific dynamic state-space models and input and output parameters are provided for the purpose of describing the present method, the present invention is not limited to examples of the dynamic state-space models, sensors, biological monitoring devices, inputs, and/or outputs provided herein.

Diagnosis/Prognosis

Figure 19:
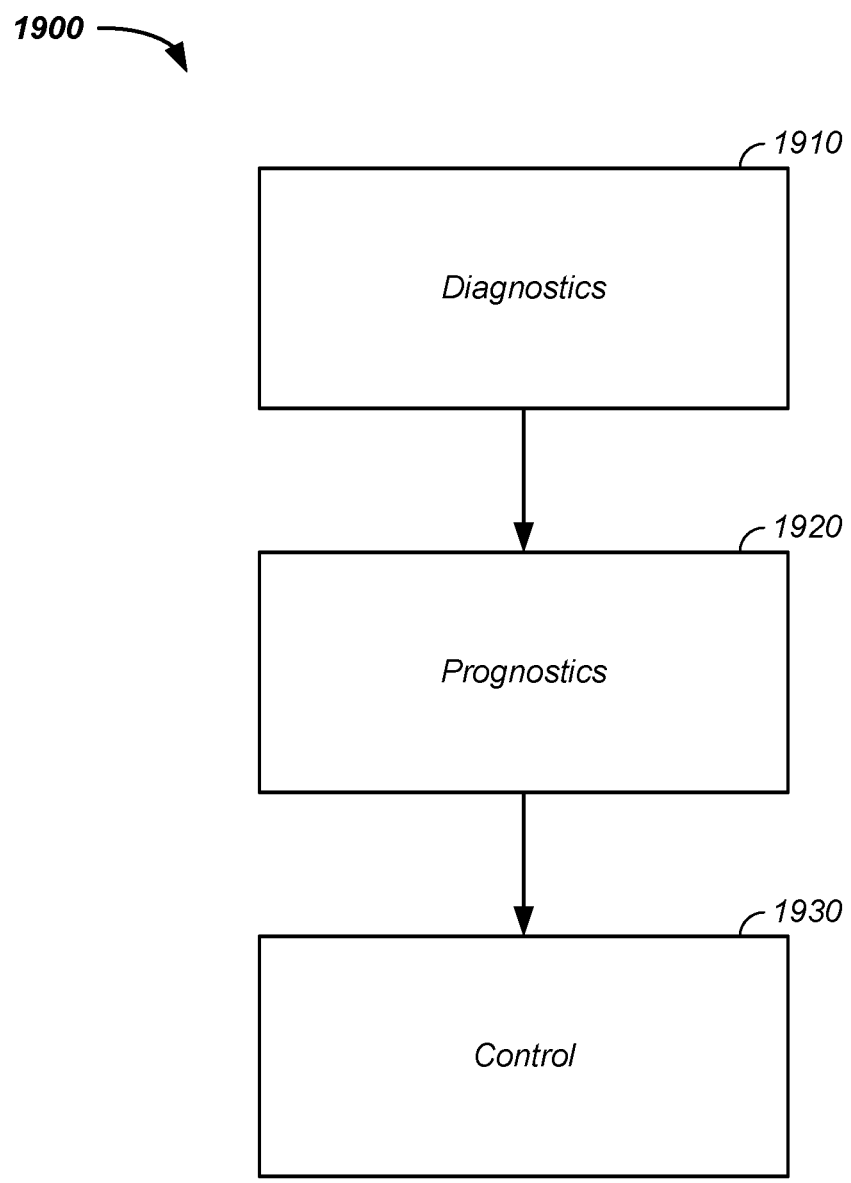
FIG. 19 provides a flowchart of dynamic state-space model diagnostics used as prognosis and control.

Referring now to FIG. 19, the output of the probabilistic digital signal processor 200 optionally is used to diagnose 1910 a system element or component. The diagnosis 1910 is optionally used in a process of prognosis 1920 and/or in control 1930 of the system.

Integrated Blood Pressure Analyzer

In another embodiment of the invention, the blood pressure sensor is integrated into/with the cardiac stroke volume analyzer. Generally, an apparatus and/or method of use thereof is used for estimating state of a cardiovascular system of a person having a limb, comprising the steps of: (1) providing a cardiac stroke volume analyzer, comprising: (a) a blood pressure sensor, the blood pressure sensor generating a time-varying pressure state waveform output from a limb of the person; (b) a system processor connected to the blood pressure sensor; and (c) a dynamic state-space model; (2) the system processor receiving cardiovascular input data, from the blood pressure sensor, related to a transient pressure state of the cardiovascular system; (3) at least one probabilistic model, of the dynamic state-space model, operating on the time-varying pressure state waveform output to generate a probability distribution function to a non-pressure state of the cardiovascular system; (4) iteratively updating the probability distribution function using synchronized updated time-varying pressure state waveform output from the blood pressure sensor; and (5) the system processor processing the probability distribution function to generate a non-pressure state output related to at least one of a stroke volume of a heart of the person, central venous pressure, and arterial compliance of the person, the output displayed to at least one of the person and a doctor. Herein, central venous pressure is a measure of pressure in the superior vena cava, which can be used as an estimation of preload and right atrial pressure. Central venous pressure is often used as an assessment of hemodynamics in a patient, particularly in intensive care units. Traditionally, the central venous pressure can be measured using a central venous catheter placed in the superior vena cava near the right atrium. A normal central venous pressure reading is between 8 to 12 mmHg. This value can be changed depending on a patient's volume status or venous compliance.

In a first case, the blood pressure sensor comprises a blood pressure cuff, such as a traditional blood pressure cuff, coupled to a pressure transducer generating a pressure waveform output, where the pressure transducer is positioned between at least a portion of an inflatable blood pressure cuff circumferentially placed around a limb and the skin. Optionally and preferably, the blood pressure cuff is used to measure blood pressure using cuff pressures that are less than a systolic pressure, such as less than 95, 90, 80, 70, 60, 50, 40, or 30 percent of systolic pressure of a given individual, such as at pressures of less than 200, 175, 150, 140, 130, 120, 110, 100, 90, or 80 millimeters of mercury (mm Hg). Optionally and preferably at least two pressure waveforms are obtained, such as a first pressure waveform as a function of time at a first applied pressure, a second pressure waveform as a function of time at a second applied pressure, and/or an $n^{th}$ pressure waveform as a function of time at an $n^{th}$ pressure, where n comprises a positive integer of at least 1, 2, 3, 4, 5, or more. The n applied pressures differ from one another by at least 2, 4, 6, 8, 10, 20, 30, or 40 percent. Optionally, the lowest pressure is equal to a diastolic pressure and/or is within 10, 20, 30, or 40 percent of the diastolic pressure, where the systolic pressure and diastolic pressure for the individual are known, determined from a first measurement, use of a reference device, and/or are assumed to be in the range of systolic and diastolic pressures for a group of humans, such as all humans, Americans, males, females, in a given weight range, and/or for a given age. Optionally and preferably, the blood pressure cuff is an automated blood pressure cuff programmed to partially inflate and partially deflate in an alternating fashion at regular time intervals, on demand, or at irregular time periods, where the partial inflation pressures are any of the above described sub-peristaltic pressures and the partial deflation pressures are any of the above described pressures that are less than the most recent or any prior pressure for a given period of wearing the blood pressure cuff. Optionally, the blood pressure cuff is used to determine blood pressure of the individual using a non-inflated form of the blood pressure cuff, such as using passive pressure against the blood pressure transducer.

In a second case, an optical system is used to determine blood pressure, where the optical system uses 1, 2, 3, or more wavelengths of light, such as in a pulse oximeter. In the second case, the optical system is optionally integrated into the blood pressure sensor system. Optionally and preferably, the pulse oximeter generates an optical waveform as a function of time, for each of 1, 2, 3, or more wavelengths of light or combinations thereof, where the blood pressure system uses the photonic signal(s) as a function of time to determine the blood pressure. When using the pulse oximeter/optical waveform continuous input approach, calibrating the resultant blood pressure using an inflatable/deflatable blood pressure cuff, as in the first case described supra is optionally and preferably used.

In either case, the time-varying pressure waveform(s) are related to blood volume and then the blood volume is related to cardiovascular state, such as stroke volume, heart stroke volume, left ventricular stroke volume, arterial compliance, and/or aortic compliance. Any of the mathematical relationships described herein of the cardiovascular system are used to link the waveform outputs to the state parameters along with or separately with any mathematical description of a pressure, force, flow, or shape of an artery, capillary bed, vein, and/or heart component, such as using an equation with a first term related to a pressure to inflate an artery and a second term related to a second pressure radially stretch the artery.

The inventor/applicant notes that the method and apparatus for determination of a left ventricle stroke volume is deemed to be statutory subject matter under 35 U.S.C. § 101 as the method and apparatus, as claimed, is not a known technique and is certainly not: (1) routinely practiced in the art, (2) well-understood, (3) routine, (4) conventional, or (5) a basic building block of human knowledge.

Further, the method and apparatus are not an implementation of a long standing, fundamental, and well-known practice. Particularly, the combination of additional elements, of: (1) a dynamic state-space model, (2) fusing sensor data, (3) a probabilistic updater, (4) iterative updating, and (5) the actual outcome of a measure not achievable by the individual medical device data, viewed in combination, amount to significantly more than the exception by meaningfully limiting the judicial exception.

Integrated Cardiac Monitor—Controllable Component

Figure 20A:
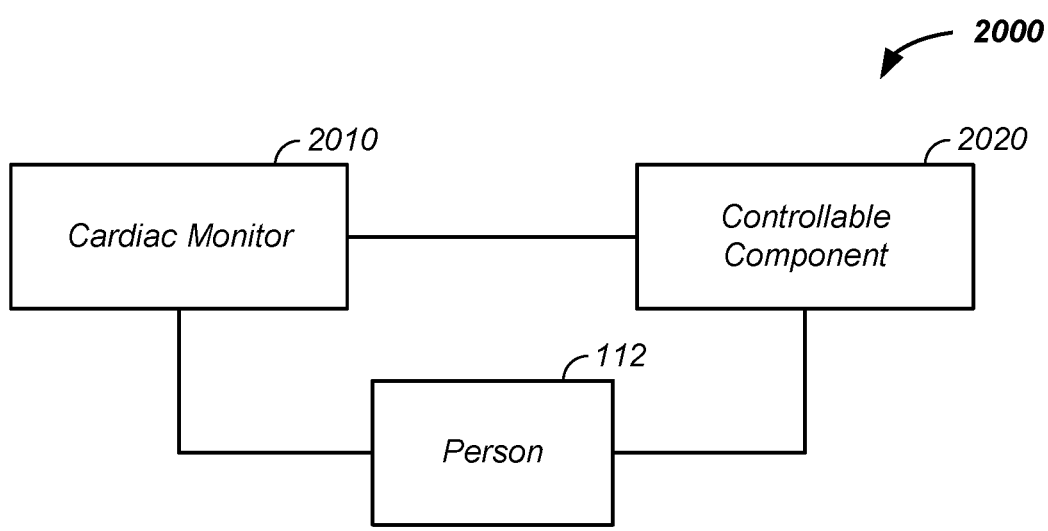
FIG. 20A, FIG. 20B, and FIG. 20C illustrate a cardiac monitor controlled device, a cardiac monitor controlling a cardiac assist pump, and input of the cardiac monitor/flow rate adjustments, respectively.

Referring now to FIG. 20A, in another embodiment, a cardiac feedback control system 2000 is described, where a cardiac monitor 2010 monitors a person 112 and output of the cardiac monitor 2010 is used to control a component 2020, such as in a feedback loop. For clarity of presentation and without loss of generality, several examples are provided, such as to feedback control of a cardiac assist pump and/or controlling a dosing pump.

Example I

Figure 20B:
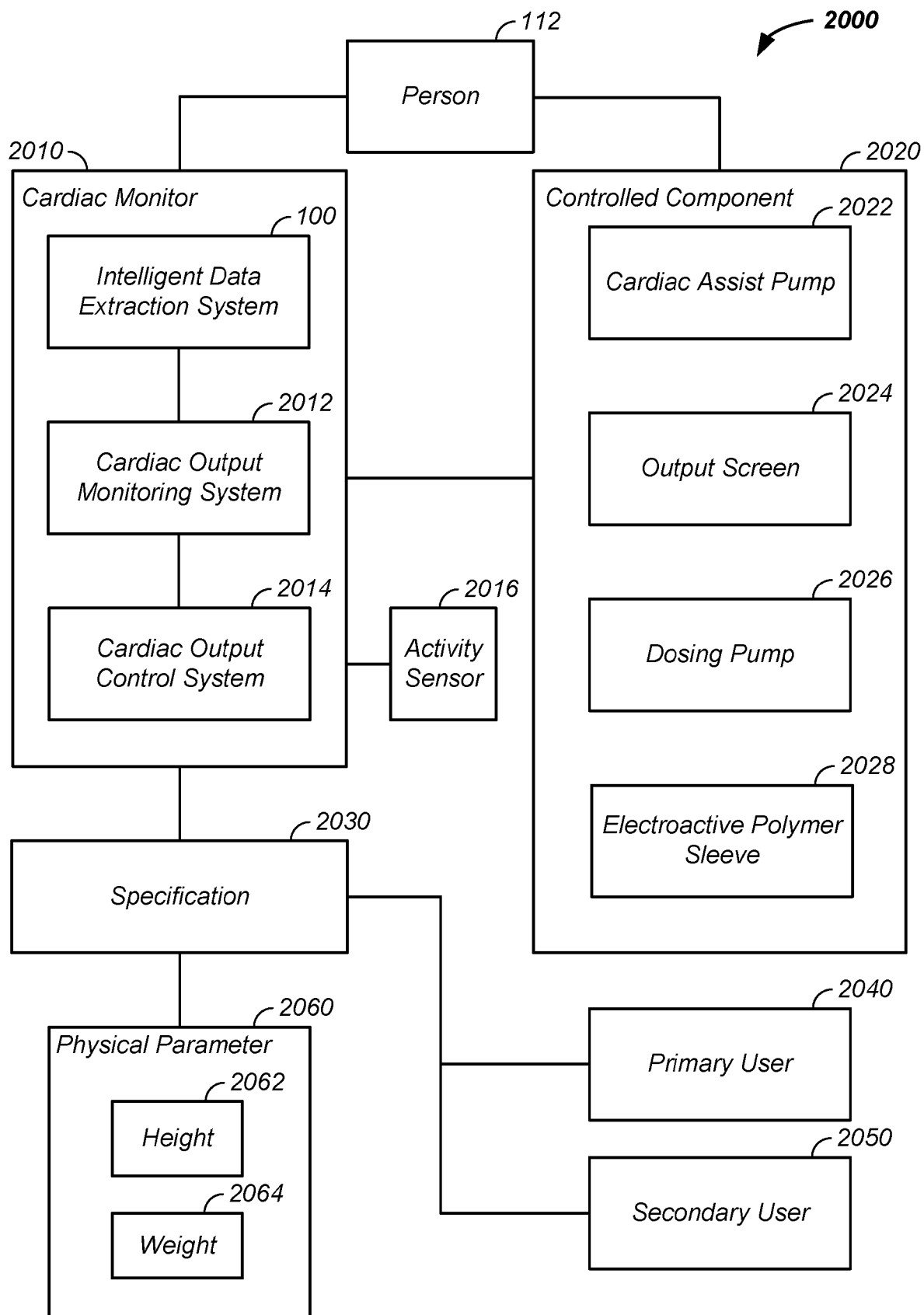

Referring now to FIG. 20B, a first example of the cardiac feedback control system 2000 is described. In this example, the cardiac monitor 110 monitors the person 112 and cardiac monitor output is provided as input to a cardiac assist pump 2022, which is an example of the controlled component 2020. The process is optionally and preferably repeated, such as in a closed control loop. The cardiac assist pump 2022 is optionally one or more of: a heart assist pump, a left ventricular assist device, and an electroactive polymer sleeve 2028. The heart assist pump and the left ventricular assist device are both commercially available. The electroactive polymer sleeve 2028 is further described, infra. Generally, the cardiac monitor 2010 includes the intelligent data extraction system 100, described supra, a cardiac output monitoring system 2012, and/or a cardiac output control system 2014. The cardiac output monitoring system 2012 monitors the cardiac state of the person 112, such as blood pressure, pulse rate, contractility, and/or left ventricle stroke volume, such as via use of at least two of: the pulse oximeter 1520, the ECG meter 1530, the blood pressure cuff 1540, and the photometer 1550, as described supra. The cardiac output control system 2014 sends a control signal to the cardiac assist pump 2022, where the control signal comprises directions and/or power to control and/or change at least one of: a pump rate, a flow rate, a pressure, a voltage, and/or timing of the cardiac assist pump 2022. Optionally and preferably, the cardiac monitor 2010 receives an input specification 2030, such as from a primary user 2040, such as the person 112, and/or a secondary user 2050, such as a doctor or health professional. Optionally and preferably, the input specification of the cardiac monitor 2010 includes one or more physical parameters 2060 of the person 112, such as a height 2062, weight 2064, and/or body mass index (BMI) of the person 112.

Figure 20C:
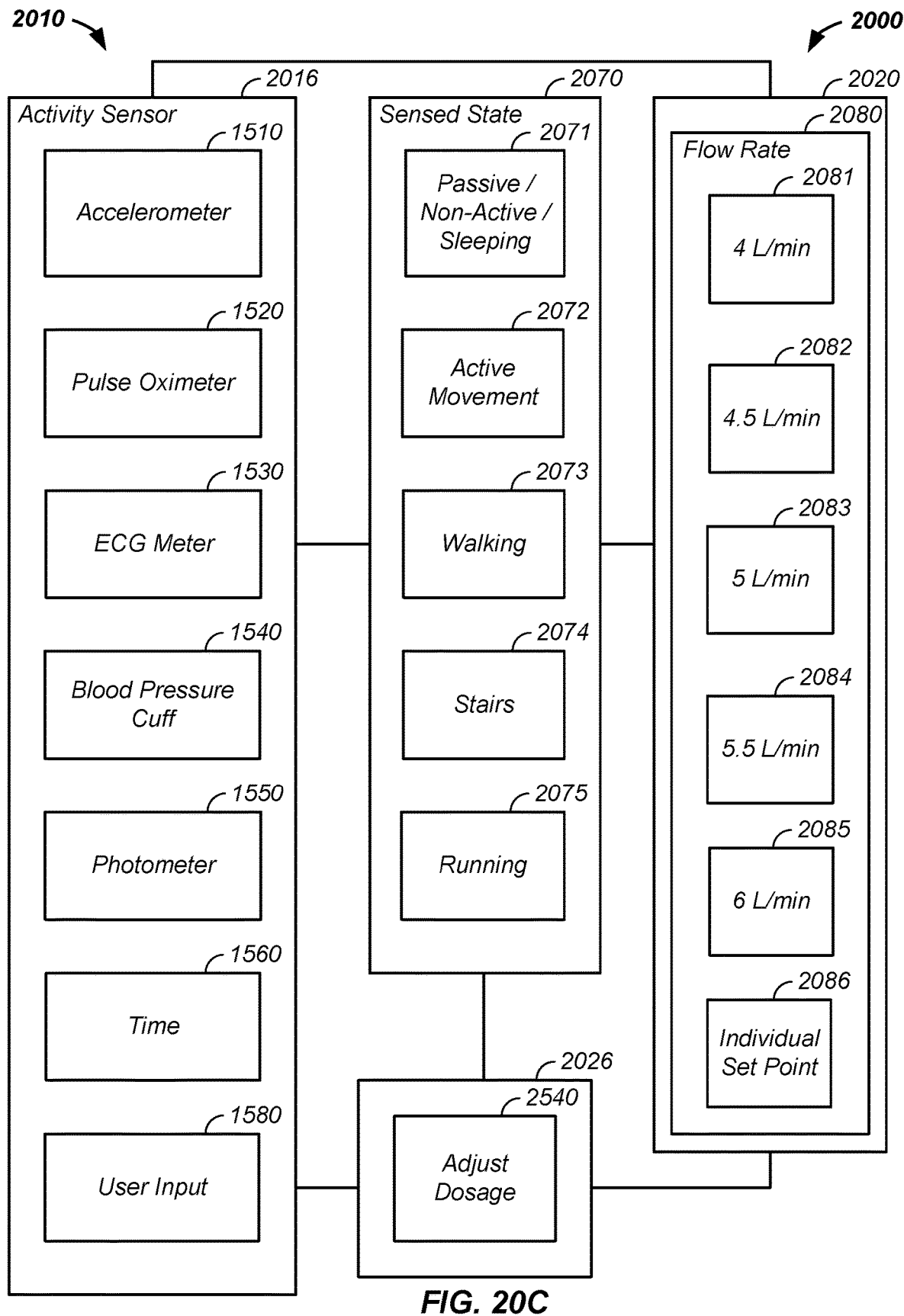

Referring still to FIG. 20B and referring now to FIG. 20C, the cardiac monitor 2010 optionally and preferably receives input from an activity sensor 2016 worn on, implanted in, worn by, and/or attached to the person 112. The activity sensor 2016 optionally and preferably includes an accelerometer 1510. Output of any one or more of the accelerometer 1510, the pulse oximeter 1520, the ECG meter 1530, the blood pressure cuff 1540, and the photometer 1550 is used as input to the cardiac monitor 2010 as a function of time 1560.

Example II

Referring now to FIGS. 20(A-C), an example of the cardiac feedback control system 2000 using a sensed state 2070 to adjust flow 2080 of blood in the person 112, such as via controlling the cardiac assist pump 2022 is described. Generally, the activity sensor 2016 is used to sense a state 2070 of the person 112. For instance, patterns of output as a function of time from the accelerometer 1510 are matched to a common activity, such as (1) sensing an inactive state at a first time, such as: a sleeping state, a resting state, a laying state, a sitting state, and a passive state and/or (2) active movement 2072, such as: an exercise state, walking 2073, a walking state, climbing stairs 2074, a climbing state, or running 2075. Particularly, observed patterns include: a repeating shallow to no movement of x/y-position repeating in time matches sleeping 2071; a randomized change in x/y-position is indicative of active movement 2072 or active motion, where the degree of x/y-position change with time is a measure of a degree of activity; a repeating slow change in x/y-position with an intervening bump in z-axis position matches walking 2073; climbing stairs 2074 includes a larger net upward vector than downward vector of movement on a repeating basis, where the difference in vector z-axis heights match that of a common stair riser; and running 2075 includes a repeating larger g-force correlated with repeating z-axis minima along with larger x/y-position changes compared to walking 2073. Further, the sensed state is optionally provided as a set point 2076, such as provided by the person 112 for a time duration, such as greater than 1, 5, 10, or 60 minutes and/or less than 60, 120, or 600 minutes. Individual sensed states 2070 of activity level of the person 112 correlate with preferred flow rates 2080 of blood, such as through the heart, a main artery, and/or a main vein. For clarity of presentation and without loss of generality, a preferred flow rate for each sensed activity is provided in Table 1. For example, a sensed state of passive, walking, and running have target blood flow rates of 4, 5, and 6 liters per minute through the left ventricle and/or aorta, respectively. Optionally, the sensed state is simply provided by the person 112, such as via an application linked to the cardiac feedback control system 2000 where the person 112 simply enters, via keyboard, text, or verbal command, a current and/or an intended activity. The input is optionally provided via a personal communication device, such as a cell phone or tablet in any wired or wireless format. Optionally, a future period of time that the intended activity will be pursued is entered. For example, the person 112 may enter that they will be walking for 30 minutes and the cardiac feedback control system 2000 will then adjust the person's flow rate to a level supporting walking for 30 minutes, with a preferable override if the cardiac feedback control system 2000 senses a change in state of the person 112, such as to a passive state 2071. Flow rates are optionally set to the individual. For instance, each flow rate in Table 1 is increased or decreased for the individual. Key is a change in targeted flow rate with a change in sensed or input activity.

TABLE 1

Exemplary Target Flow Rates

| Sensed State | Flow Rate (L/min) |
| --- | --- |
| Passive/Sleeping | 4.0 |
| Active Movement | 4.5 |
| Walking | 5.0 |
| Stairs | 5.5 |
| Running | 6.0 |
| user set | user set |

Still referring to FIG. 20C, the flow rate 2080 is an overall flow rate. Essentially, the cardiac feedback control system 2000 assists the flow rate of the person 112. For instance, if the targeted flow rate is 5 L/min and the person is only achieving 4.0 L/min, then the cardiac feedback control system 2000 directs the cardiac assist pump 2022 to assist in blood flow until the person's total flow rate is increased to the targeted flow rate, such as by adding 1.0 L/min to the overall flow rate. As the cardiac feedback control system 2000 is dynamic, it is a feedback controlled system, then if the person after a period of time is achieving 4.5 L/min on their own, then the cardiac feedback control system 2000 tapers back to a level of adding a lesser 0.5 L/min to the overall flow rate.

Example III

In the prior two examples, the cardiac feedback control system 2000 altered the flow rate, such as a blood flow rate, of the person 112 to dynamically achieve a targeted flow rate, such as by adjusting the flow rate of the cardiac assist device/cardiac assist pump 2022, such as adjusting the flow rate at times exceeding every 0.5, 1, 2, 5, 10, 30, 60, or more seconds. Optionally, the cardiac feedback control system 2000 controls a dosing pump, where the delivered dosing agent increases or decreases a heart rate or blood flow rate. As dosing involves a response time, the cardiac feedback control system 2000 optionally and preferably alters the delivered dose at time intervals greater than 0.5, 1, 2, 6, 12, or 24 hours.

Example IV

In any example provided herein, output of the cardiac feedback control system 2000 is optionally provided as a data file and/or is provided graphically to an output screen 2024, such as on the controlled unit 2020, on the cardiac monitor 2010, and/or on a remote screen, such as on a tablet or cell phone application.

Example V

In another example, output from the cardiac monitor 2010 is used to direct/control/alter output/adjust dosage 2540 of a dosing pump 2026. Optionally and preferably, a dosing pump, such as a commercially available pump, is additionally configured with the cardiac monitor 2010 and the output of the dosing pump 2026 is adjusted based upon a sensed state of a person or subject. For instance, a method for operating a drug delivery system, comprises the steps of:
  receiving to the drug delivery system a first time-varying cardiovascular input waveform from at least one of:
    a pulse oximeter; and
    a blood pressure monitor;
  operating on the time-varying cardiovascular input waveform to generate transient cardiovascular state information, comprising at least one of:
    a current left ventricle stroke volume;
    a current blood pressure;
    a current arterial compliance; and
    a current blood flow rate; and
  directing the drug delivery system to deliver a drug based on the generated transient cardiovascular state information.

Example VI

Referring now to FIGS. 21-24, in another example, the cardiac feedback control system 2000 controls a sleeve, such as an electroactive polymer sleeve 2028 comprising one or move electroactive polymers. In this example of a heart assist device, the heart assist device comprises a compressible sleeve about a body part, where one or more portions of the sleeve compress to provide a force on a body part, which generates a blood flow or pulse in the human circulatory system. In one case, the sleeve is external to the body, such as about a limb or a body extremity. In another case, the sleeve is internal to the body, such as about the heart, a section of the heart, an artery, or a vein. In still another case, two or more sleeves cooperatively function in parallel and/or in series. For instance, a method for aiding function of a heart, comprising the steps of:
  sensing a pulse;
  providing a blood flow assist device, comprising:
    a first electroactive polymer sleeve segment circumferentially positioned about a portion of a first body part; and
    a second electroactive polymer sleeve segment circumferentially positioned about a segment of a second body part;
  sequentially constricting, timed to the pulse, the first electroactive polymer sleeve segment and the second electroactive polymer sleeve segment to aid the heart in circulation of blood; and
  repeating the step of sensing the pulse and the step of constricting.

Example VII

With a heart transplant, nerves leading to the heart are cut. As a result, natural body responses to stimuli that would drive heart rate are not effective. In one embodiment, one or more responses from the activity sensor 2016 are used to bump up blood flow rate 2080, such as by greater than 1, 2, 5, 10, 20, 40, 50, 60, 80, or 100 percent, of an artificial heart or the cardiac assist pump 2022, such as for a period of greater than or equal to 5, 10, or 30 seconds or 1, 2, 5, 10, 20, or 30 minutes. For clarity of presentation and without loss of generality, several sensors are described, where the output of the sensor is used to drive blood flow with the cardiac feedback control system 2000. In a first case, a sound sensor upon sensing a sharp or loud sound, such as an explosion, kicked in door, or dropped pan, is used to temporarily drive an elevated blood flow rate, which simulates a natural body response to an audible shock sensed by the body. In a second case, output from a lactic acid sensor sensing an increased or increasing lactic acid concentration in the blood is used to increase a blood flow rate as the increased lactic acid is a result of muscle movement and/or muscle strain depleting oxygen in the blood. In a third case, output from an blood oxygen sensor, such as sensing hypoxemia, is used to increase the blood flow rate as low blood oxygen concentrations are indicative of poor circulation and/or physical exertion. In a fourth case, output of a blood adrenaline sensor is used to temporarily increase blood flow. Generally, one or more blood sensors, sensing a blood constituent/analyte concentration, and/or one of more environmental sensors, sensing or responding to an environmental change that would normally drive up a heart rate, are used to temporarily provide a boost to the flow rate provided by the cardiac assist pump 2022.

Heart Assist Device

A blood circulation device 2100 is optionally an artificial heart or a heart assist device. For clarity of presentation and without loss of generality, the heart assist device is further described herein. However, the elements of the heart assist device 2110 and their uses also apply to use as an artificial heart.

Figure 21:
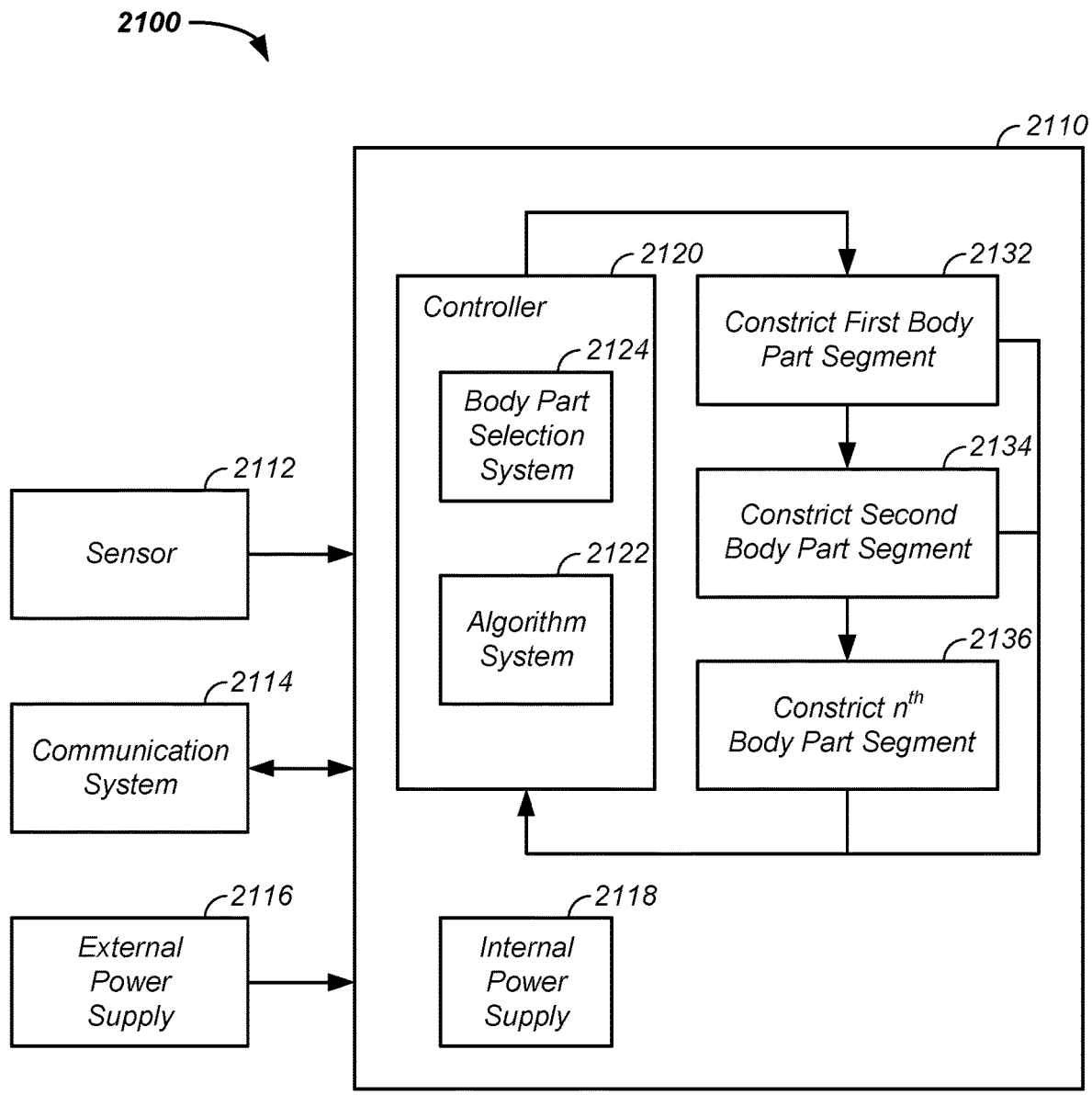
FIG. 21 illustrates major components and operation of a heart assist device.
Figure 22A:
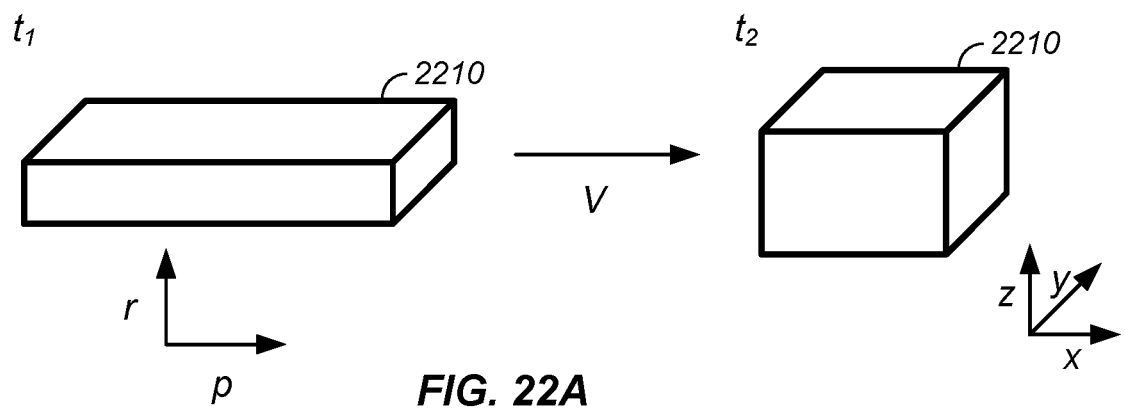
FIG. 22A and FIG. 22B illustrate an electroactive polymer and an electroactive polymer sleeve, respectively.
Figure 22B:
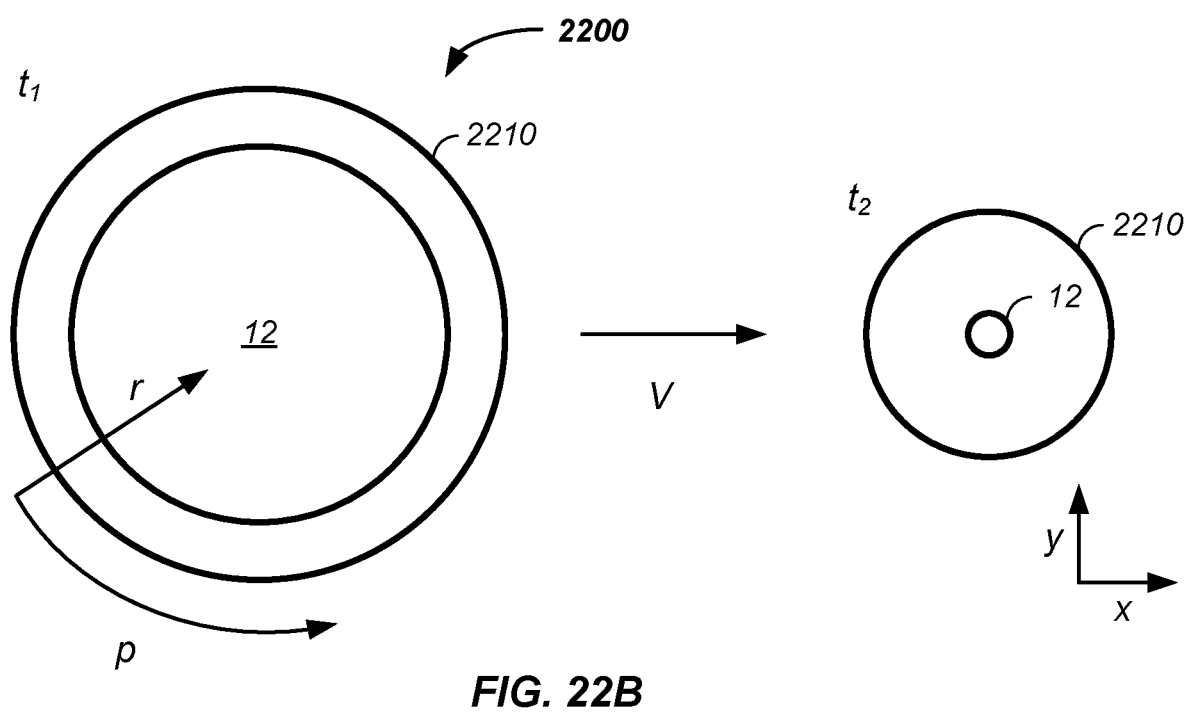
Figure 23A:
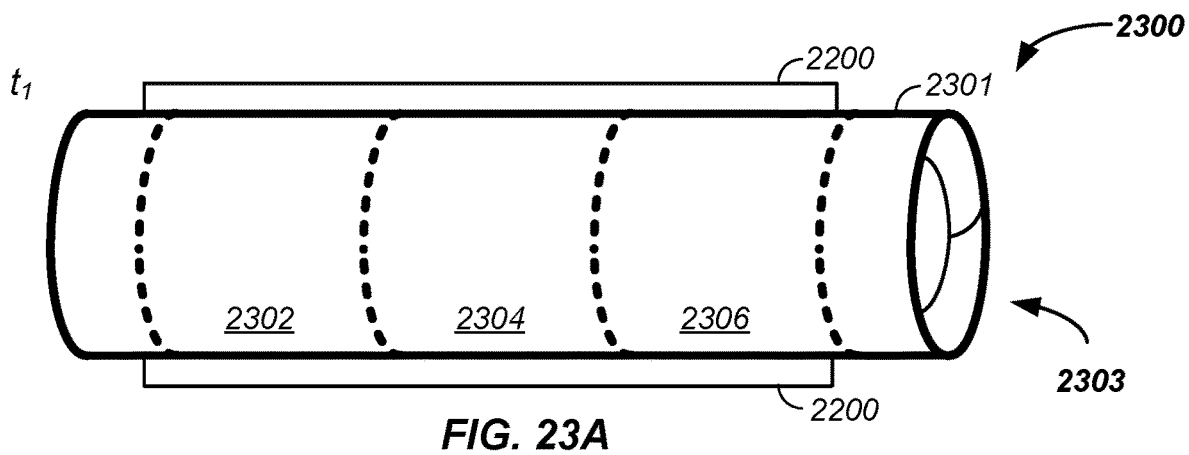
FIGS. 23(A-D) illustrate a series of electroactive sleeve segments operating in time series on a body part at a first time, FIG. 23A; at a second time, FIG. 23B, at a third time, FIG. 23C; and at a fourth time, FIG. 23D.
Figure 23B:
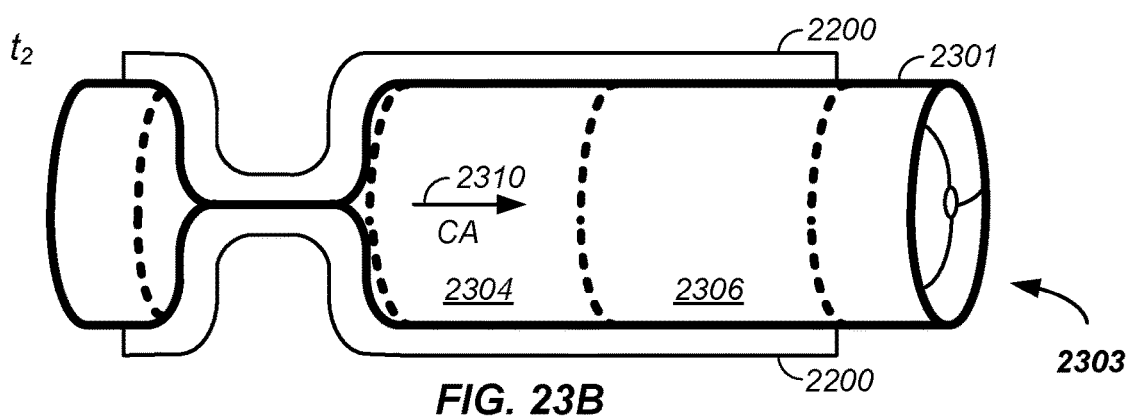
Figure 23C:
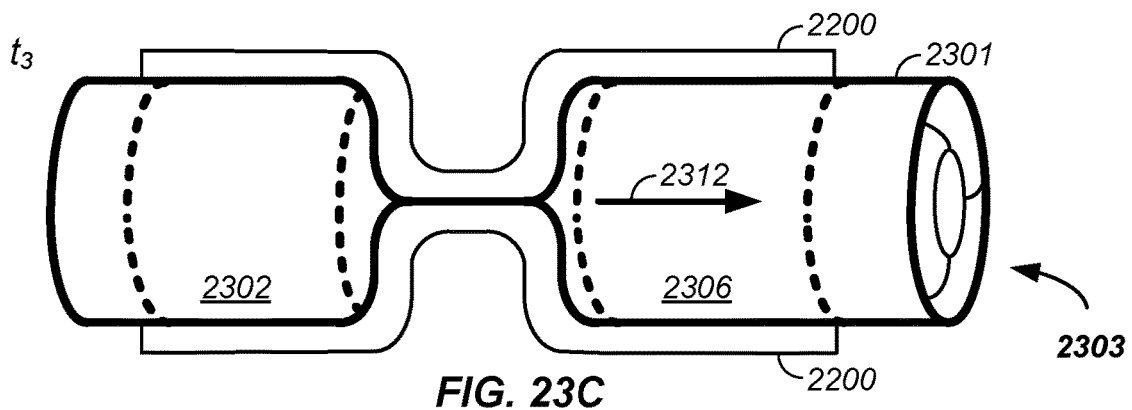
Figure 23D:
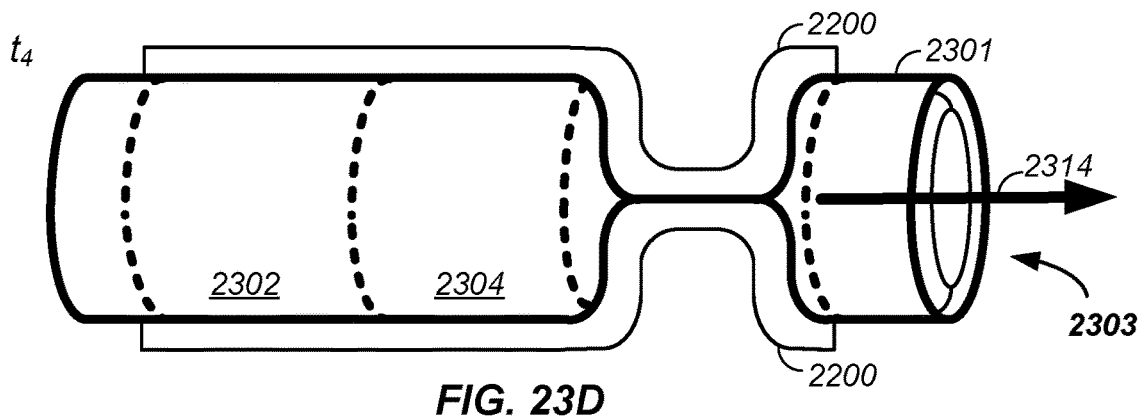

Referring now to FIG. 21 and FIG. 22B, an example of a heart assist device 2110 is provided. Generally, the heart assist device 2110 includes a heart assist device controller 1120 and a sleeve 2200, where an inner cross-sectional area 2134 of the sleeve 2200 is controlled by the heart assist device controller 1120 as a function of time. As the inner diameter of the sleeve 2200 about the body part constricts, blood is forced from the body part to an adjoining body part, such as through the circulatory system.

Still referring to FIG. 21, the heart assist device controller 1120 of the heart assist device 2110 controls: (1) timing of constriction of the sleeve 2200 and (2) position of constriction of the sleeve 2200. In a first case, the heart assist device controller 1120 controls constriction of the sleeve 2200 about a body part. In a second case, the heart assist device controller 1120 controls a series of constrictions of a series of segments of the sleeve 120 about a series of segments about a single body part to force blood in a forward direction through the circulatory system of the body. For example, the sleeve segments are serially constricted about an artery along the axis of blood flow to force blood in the artery through the circulatory system of the body. The second case is further described, infra, when referring to FIG. 23. In a third case, the heart assist device controller 1120 controls a set of constrictions of a set of sleeves about two or more body parts. For example, two or more sleeves 2200 are positioned on the arms and/or legs of the body and the controller constricts the individual sleeves at a single time, in a rhythm, in a repeating and/or repetitive pattern, in series, in parallel and/or under the control of the heart assist device controller 1120. The third case is further described, infra, when referring to FIG. 24. In a fourth case, the heart assist device 2110 constricts a series of segments of each of two or more sleeves 200, which is a combination of the second case with the third case. Generally, the controller directs constriction of one or more sleeves about a first body segment 2132, about a second body segment 2134, and/or about an $n^{th}$ body segment 2136 as a function of time, where n is a positive integer. Optionally, two or more sleeve segments are constricted at essentially the same time, such as within less than 1, 0.5, 0.25, or 0.1 seconds apart; having overlapping constriction periods; and/or have time periods of initiation of constriction at least 0.05, 0.1, 0.25, or 0.5 seconds apart.

In one case, a first sleeve is worn around the left leg of the person 112 and a second sleeve is worn around the right leg of the person 112. In some instances, the person 112 has poorer circulation in one leg, such as the right leg, compared to the other leg, such as results from taking arteries from one leg in bypass surgery. In this case, the cardiac feedback control system 2000 provides a greater assistance to blood flow in the second sleeve worn around the circulation impeded right leg compared to a lesser assistance or no assistance to circulation of the left leg. For instance, one sleeve, such as about the right leg, provides greater than 1, 2, 5, 10, 25, 50, or 100 percent additional boosted blood flow compared to another sleeve, such as about the left leg.

In another case, a first sleeve worn about a first section of a return vein provides greater blood flow assistance than a second sleeve worn about a second section of a return vein, where the first sleeve is further from the heart than the second vein along a longitudinal vein path to the heart. In any case, each of n sleeves optionally provide a corresponding blood flow assistance that optionally differ from each other by greater than 1, 2, 5, 10, 25, 50, or 100 percent, where n is a positive integer of at least 2, 3, 4, 5, or more.

In another case, a series of sleeves worn around the heart are used to contract heart sections, such as an atrium or ventricle section. In addition, the series of sleeves not only duplicate and assist pumping of each heart section, but also assist the natural twisting, vertical, and/or horizontal motion of the heart with successive heartbeats.

Generally, in addition to the heart assist device controller 1120 with an optional algorithm system 2122 and/or a body part selection system 2124, the heart assist device 2110 optionally includes any of: a sensor 2112, such as a hemodynamic sensor and/or an electrodynamic sensor, a communication system 2114, an external power supply 2116, and/or an internal power supply 2118. The sensor 2112 and the communication system 2114 are preferably external to the body, but are optionally implanted into the body.

Referring now to FIG. 22, the sleeve 2200 of the heart assist device 2110 is further described. Herein for clarity of presentation and without loss of generality, an electroactive polymer is used to illustrate function of the sleeve. For example, the sleeve 2200 is optionally a mechanical peristaltic pump, a pneumatic system, and/or an artificial muscle. The electroactive polymer is optionally an ionic polymer-metal composite, a dielectric polymer, an ionic polymer, an electrostrictive polymer, and/or a liquid crystalline polymer. Optionally, the electroactive polymer is configured as fibers or fiber bundles formed into a ring to enhance range of motion. Generally, the sleeve 2200 uses any material, mechanical system, biomechanical system, and/or electrodynamic system that changes shape as a function of time to move blood in the circulatory system of the body. Similarly, the sleeve 2200 material is optionally any natural material, synthetic material, and/or polymer that changes shape as a function of time to move blood in the circulatory system of the body.

Referring now to FIG. 22A, an electroactive polymer 2210 is further described. An electroactive polymer changes shape when stimulated by an electric field. Typically, an electroactive polymer is capable of a large amount of deformation while sustaining large forces. In FIG. 22A, the electroactive polymer 2210 is depicted in a first geometry at a first point in time, $t_1$, and in a second geometry at a second point in time, $t_2$, after application of a voltage, V, to the electroactive polymer 2210. In the geometry depicted, the electroactive polymer reduces length along the x-axis and increases thickness along the z-axis upon application of the electric field. For clarity, the x-axis is also labeled as the perimeter, p, axis and the z-axis is also labeled as the radius, r, axis. While the electroactive polymer 2210 is depicted as increasing in thickness and shrinking in length as a function of an applied electric field, generally independent control of each axis shape of the electroactive polymer 2210 is made possible through the chemical choice of monomer units of the polymer, control of the electric field, and manufacturing process. In addition, while the applied force to the electroactive polymer 2210 is depicted as a voltage, optionally the applied force is any current, pressure, magnetic field, or induced field acting on the sleeve material that results in a changed shape as a function of time.

Referring now to FIG. 22B, the electroactive polymer depicted in FIG. 22A is formed as a ring or as the sleeve 2200 about a body part 12. As orientated, the x-axis of FIG. 22A is now the perimeter axis, p, in FIG. 2B and the z-axis of FIG. 22A is now the radius axis in FIG. 22B. With application of the electric field to the electroactive polymer 2210, the x-axis reduces in size. The reduced x-axis length shrinks the outer perimeter of the sleeve 2200. Similarly, the z-axis of FIG. 22A is now the radius axis, r, of the sleeve 2200 in FIG. 22B. With application of the electric field to the electroactive polymer 2210, the z-axis increases in size. The increased z-axis length shrinks the inner perimeter of the sleeve 2200. The decreased perimeter of the sleeve 2200 and/or the increased radial thickness of the sleeve 2200 reduces or constricts the size of the body part 12 within the sleeve. For example, an artery is constricted by the electroactive polymer upon application of an electric field to the electroactive polymer 2210. With removal of the electric field, the electroactive polymer will revert back to its original shape or vice versa. The process of cyclical, periodic, rhythmic, or controlled time series application of the electric field to the electroactive polymer 2210 by the heart assist device controller 1120 is repeated in a manner resulting in the circulation of blood in the circulatory system of the body.

Referring now to FIG. 23, a vein 2300 having an outer wall 2301, a circulation axis 2310, CA, and a valve 2303 is illustrated, where the vein 2300 is also representative of an artery, a heart, or an extremity of the body, such as an arm or leg. The sleeve 2200 or electroactive polymer 2210 in the shape of a sleeve is circumferentially positioned about the artery 2300, such as in proximate contact with the wall 2301 of the artery 300. Referring now to FIG. 23A, at a first point in time, $t_1$, the sleeve 2200 is maintained in a non-constricted state, which is optionally a relaxed state of the electroactive polymer 2210. Referring now to FIG. 23B, at a second point in time, $t_2$, a first segment 2302 of the sleeve 2200 is constricted, which forces blood forward along the circulation axis at a first velocity or pressure 310. Optionally, at a third point in time, $t_3$, a second segment 304 of the sleeve 2200 is constricted, which, in combination with the prior constriction of the first segment 2302, forces the blood forward along the circulation axis at a second velocity or pressure 2312. Optionally, at a fourth point in time, $t_4$, a third segment 2306 of the sleeve 2200 is constricted, which, in combination with the prior constriction of the first segment 2302 and second segment 3204, forces the blood forward along the circulation axis at a third velocity or pressure 2314. Optionally, the sleeve 2200 is positioned prior to the valve 2303, such as within less than 1, 2, 3, 4, or 5 inches of the valve 2303 to use the valve 2303 as a natural backflow prohibited to the blood flow. Two of more segments are optionally simultaneously constricted. For example, the first segment 2302 is optionally constricted until the second segment 2304 is constricted to force the displaced blood forward along the circulation axis. Generally, the sleeve 2200 optionally contains n segments, where n is a positive integer of at least one and the sleeve is sequentially constricted along the circulation axis 310 through the n segments.

Figure 24:
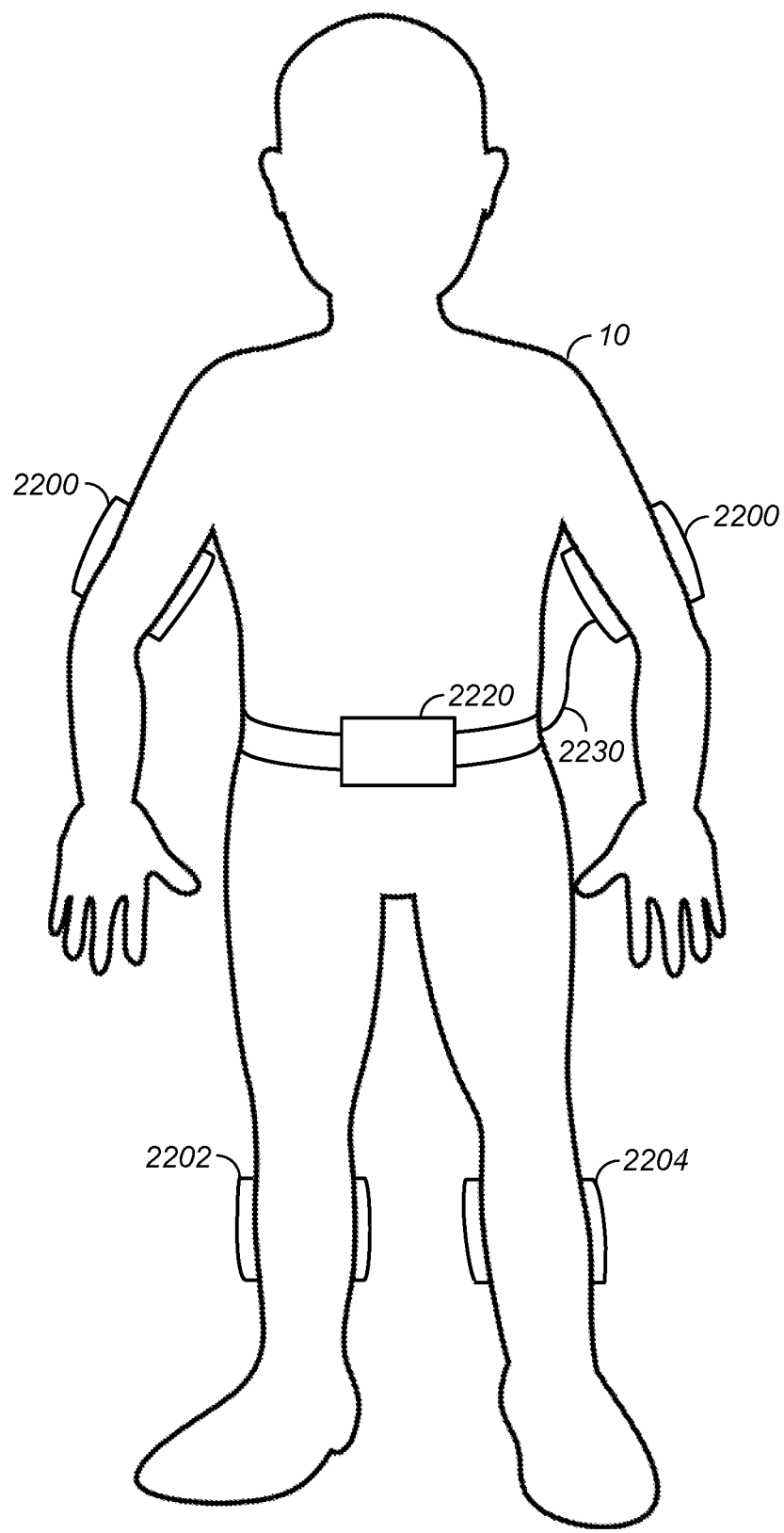
FIG. 24 illustrates two or more cooperatively operating heart assist devices.

Referring now to FIG. 24, the heart assist device 2110 is depicted as using two or more sleeves 2200 on arms and legs of a subject 10. However, the description of use of two or more sleeves, as illustrated about arms and legs of the subject 10, also applies to the use of two or more sleeves about arteries or veins of the subject 10.

Still referring to FIG. 24, the heart assist device 2110 need not replace a heart of the subject 10, patient, or person. The heart assist device 2110 optionally assists the heart for a short duration, such as for minutes or hours as in a medical emergency when the heart stops, as for example sensed by a pulse sensor, or longer term such as days, weeks, months, or years to aid a failing heart. As such, the sleeve 2200 is optionally worn externally to the subject 10, such as along an arm or leg of the subject 10. For clarity of presentation, an example of multiple sleeves on legs is used. A first sleeve 2202 compresses a portion of a first leg and/or foot which forces the pooling or poorly circulating blood up the first leg and/or foot in the circulatory system. The resulting force on the blood may be sufficient to be used independently. Optionally, a second sleeve 2204 about a second leg or foot is also similarly used. The heart assist device controller 1120 optionally constricts the first sleeve 2202 and the second sleeve 2204 at the same time, within one, two, or three seconds of each other, or at different times. Similarly, the first sleeve 2202 and the second sleeve 2204 are optionally worn on the same leg, a leg and an arm, or on two arms. Any number of sleeves 2200 are optionally used and the controller optionally constricts any one or any combination of the sleeves at the same or different times to achieve circulating blood flow in the subject 10. An optional embodiment of the sleeve 2200 is in the form of a sock. Optionally, the sensor 2112 is integrated into the sock.

Still referring to FIG. 24, the blood circulation device optionally uses a power supply and/or user communication system worn as a belt 2220 that is optionally directly wired using a wire 2230 to the sleeve 2200.

As described, supra, the blood circulation device 2100 is optionally used with a sensor 2112. The electrodynamic and/or hemodynamic sensor is optionally used to provide information about pulse, temperature, and/or blood pressure to the heart assist device controller 1120 where the algorithm system 2122 determines a need to increase, maintain, or decrease the blood flow.

Optionally, a sensor is used as part of the heart assist device, such as to determine timing of a function related to the heart, such as timing of a blood pulse, measurement of a ventricular stroke volume, measurement of a ventricle filling rate, determination of a radial pulse, and/or determination of a radial blood flow. Optionally, the sensor or set of sensors is used to time function of the ventricular assist device, such as to time initiation of an induced pulse, median time of an induced pulse, or mean time of an induced pulse to lag a pulse initiation of the heart by more than 0.01, 0.05, 0.1, 0.2, 0.3, 0.5, 0.75, or 1 second to time the assist of the induced pulse with the heart pulse passing through the ventricular assist device pumping mechanism, so as to enhance and not impede the heart pulse.

Emergency Use

The sensor 2112 or set of sensors, such as the electrodynamic and/or hemodynamic sensor are also optionally configured with the controller for use in an emergency situation, such as with an arrhythmia or with stoppage of the heart. In such an event, the sensor 2112 is used to detect the emergency situation and to initiate start-up of the blood circulation device 2100. In this case, the blood circulation device 2100 was worn by the subject 10 in the event of an emergency.

For example, the blood circulation device 2100 is optionally developed into socks and worn daily in old age in the event of a heart attack. In another example, the blood circulation device 2100 is worn by a patient as a security measure during an operation or while sleeping. In yet another example, the blood circulation device is configured with an audible alarm and/or a verbal alarm notifying the user and/or people proximate the user of a prognosticated or current emergency medical situation. For example, the sensor 2112 or set of sensors optionally determines a partial circulatory system blockage, abnormal oxygen levels in the blood, and/or a blood pressure rise while at rest and prognosticates a heart event due to decreased oxygen to the heart muscles.

Communication System

Generally, a communication system operating in conjunction with the heart assist device 2110 communicates state of the subject 10 to the subject 10 and/or to a remote system, such as to an emergency network system and/or to a medical practitioner.

In one case, the communication system is a link to a smartphone. The smartphone herein also refers to a feature phone, a tablet, a phablet, a mobile phone, a portable phone, and/or a cell phone. The smartphone contains a number of hardware and software features, which are optionally usable in combination with the blood circulation device 2100, such as a hardware port, a communication system, a user interface system, a global positioning system, a memory system, a secure section, an identification system, and/or a power inlet or power supply.

The hardware port of the smartphone typically optionally contains one or more electro-mechanical connectors designed to physically link to the blood circulation device. Examples of connectors include a power supply port, a universal serial bus (USB) port, an audio port, a video port, a data port, a port for a memory card, and a multi-pin connector, such as a 30-pin connector. Further, integration of the heart assist device 2110 with a smartphone reduces need for an integrated computer system and communication system. Still further, integration of the heart assist device 2110 with a smartphone provides a back-up or redundant system, which is helpful in a life-saving/life-maintaining apparatus.

Each of the communication system, the personal communication device, the user interface system, the global positioning system, and/or the memory of the smartphone is optionally used as part of the blood circulation device 2100. In a first example, the subject 10 uses the smartphone to call an authority system to report the individual's location, using the communication system, user interface system, and global positioning system, where the smartphone is used to confirm identity, medical state, and position of the individual. In a second example, the cell phone automatically communicates position and medical state of the individual to an emergency system without interaction of the individual 10. Herein, for clarity of presentation the smartphone is used to describe a generic digital communication device, such as a phone, a tablet computer, and/or a computer.

Personal Monitor

In another embodiment, the blood circulation device 2100, described supra, is used as a part of a process of relaying personal data to an external network. For example, a sensor is used to read a body parameter of the subject 10 and to relay the data directly and/or through the communication device to an external network. For example, the blood circulation device and smartphone combination is used as part of a personal health monitoring system. In the personal health monitoring system, the user 10 wears the blood circulation device 2100 and data from the sensor 2112 and/or the blood circulation device 2100 is sent through the communication device to a remote service, such as a health monitoring company, the user's personal computing system, a medical monitoring service, friends, family, and/or an emergency response agency. Examples of the sensor 2112 include any of: an alcohol monitor, a drug monitor, a temperature monitor, a pacemaker monitor, a heart rate monitor, a blood pressure monitor, an electrode affixed to a body part, a force meter, a temperature probe, a pH reader, a hydration monitor, or a biomedical sensor element. For example, the wearable biomedical sensor monitors a pacemaker and in the event of an abnormality relays the abnormality and location of the individual through the communication device to a remote service, such as to a dispatcher, for medical service and/or to a medical professional.

Still yet another embodiment includes any combination and/or permutation of any of the elements described herein.

Herein, a set of fixed numbers, such as 1, 2, 3, 4, 5, 10, or 20 optionally means at least any number in the set of fixed number and/or less than any number in the set of fixed numbers.

Herein, any number optionally includes a range of numbers such as the number, n, ±1, 2, 3, 4, 5, 10, 20, 25, 50, or 100% of that number.

The particular implementations shown and described are illustrative of the invention and its best mode and are not intended to otherwise limit the scope of the present invention in any way. Indeed, for the sake of brevity, conventional manufacturing, connection, preparation, and other functional aspects of the system may not be described in detail. Furthermore, the connecting lines shown in the various figures are intended to represent exemplary functional relationships and/or physical couplings between the various elements. Many alternative or additional functional relationships or physical connections may be present in a practical system.

In the foregoing description, the invention has been described with reference to specific exemplary embodiments; however, it will be appreciated that various modifications and changes may be made without departing from the scope of the present invention as set forth herein. The description and figures are to be regarded in an illustrative manner, rather than a restrictive one and all such modifications are intended to be included within the scope of the present invention. Accordingly, the scope of the invention should be determined by the generic embodiments described herein and their legal equivalents rather than by merely the specific examples described above. For example, the steps recited in any method or process embodiment may be executed in any order and are not limited to the explicit order presented in the specific examples. Additionally, the components and/or elements recited in any apparatus embodiment may be assembled or otherwise operationally configured in a variety of permutations to produce substantially the same result as the present invention and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. A method for operating a cardiac assist pump, comprising the steps of:
    providing a cardiac monitor comprising:
        a cardiac output sensor comprising at least two of:
            a pulse oximeter;
            an electrocardiogram meter; and
            a blood pressure monitor; and
        an activity sensor;
    receiving first input data comprising time-varying cardiovascular input data, from said cardiac output sensor, related to a transient hemodynamic state of a cardiovascular system;
    receiving second input data comprising time-varying activity input data, from said activity sensor;

operating on the time-varying cardiovascular input data to generate transient cardiovascular state information, comprising at least one of:
    a current left ventricle stroke volume;
    a current blood pressure; and
    a current blood flow rate;
generating a target cardiovascular state with said time-varying activity input data;
repeating: (1) said step of receiving first input data, said step of receiving second input data, and said step of operating to update said transient cardiovascular state information and (2) said step of sensing to update the target cardiovascular state; and
directing said cardiac assist pump to adjust assisted blood flow, yielding the updated transient cardiovascular state, toward the target cardiovascular state,
controlling, with said cardiac monitor, at least one of: said step of receiving first input data, said step of receiving second input data, and said step of directing.

2. The method of claim 1, further comprising the step of:
receiving via said activity sensor a user input setting.

3. The method of claim 2, said step of receiving further comprising the steps of:
receiving into a cardiac feedback control system a first user input setting to an inactive state at a first time, said inactive state comprising at least one of: a sleeping state, a resting state, a laying state, a sitting state, and a passive state; and
receiving into the cardiac feedback control system a second user input setting to an active state at a second time, said active state comprising at least one of a walking state, an exercise state, and a climbing state, said cardiac feedback control system comprising said cardiac monitor.

4. The method of claim 2, said step of receiving further comprising the step of:
receiving a set blood flow rate.

5. The method of claim 1, said step of sensing activity, further comprising at least one of the steps of:
sensing walking; and
sensing climbing stairs.

6. The method of claim 1, said step of sensing activity further comprising the step of:
sensing an inactive state at a first time, said inactive state comprising at least one of: a sleeping state, a resting state, a laying state, a sitting state, and a passive state; and
sensing an active state at a second time, said active state comprising at least one of a walking state, an exercise state, a climbing state.

7. The method of claim 1, said step of sensing activity further comprising the step of:
detecting a mean x/y-position change of less than two meters per minute at a first time; and
detecting a mean x/y-position change of greater than two meters per minute at a second time, where an x/y-plane is perpendicular to a z-axis aligned with gravity.

8. The method of claim 1, said step of sensing activity, further comprising the steps of:
sensing a change in state; and
adjusting assisted blood flow delivered by said cardiac assist pump in response to said sensed change in state.

9. The method of claim 8, said step of adjusting further comprising the step of:
increasing an assisted blood flow from said cardiac assist device from a rate of less than one-half liter per minute to a rate in excess of three-quarters liter per minute, wherein the assisted blood flow from said cardiac assist device and an unassisted heart blood flow each comprises a fraction of a total blood flow.

10. The method of claim 1, further comprising the step of:
increasing an operational rate of said cardiac assist pump in response to a falling percent oxygen saturation detected by at least one of: said pulse oximeter and said step of operating.

11. The method of claim 1, further comprising the step:
directing an infusion pump to deliver a medication in addition to said step of directing said cardiac assist pump to adjust assisted blood flow.

12. The method of claim 1, further comprising the step of:
dynamically adjusting said cardiac assist pump to maintain a percent oxygen saturation in a set range, said percent oxygen saturation dynamically measured by at least one of said pulse oximeter and said step of operating.

13. The method of claim 1, further comprising the step of:
assisting blood flow with a first electroactive sleeve, said cardiac assist pump further comprising said first electroactive polymer sleeve.

14. The method of claim 13, further comprising the step of:
assisting blood flow with a second electroactive polymer sleeve, said cardiac assist pump further comprising said second electroactive polymer sleeve.

15. The method of claim 14, said step of directing further comprising the step of:
directing said first electroactive polymer sleeve to operate at a flow assist rate at least ten percent greater than said second electroactive polymer sleeve.

16. The method of claim 1, further comprising the step of:
measuring pressure from an alternating partial inflation of a blood pressure cuff and a partial deflation of said blood pressure cuff with a pressure transducer output of said blood pressure monitor.

17. The method of claim 1, further comprising the step of:
measuring pressure, using a blood pressure cuff alternatingly at a first partially inflated pressure in excess of 100 mm Hg and a second partially deflated pressure of less than 100 mm Hg, directly as a function of time to yield a time varying pressure state waveform provided to said blood pressure monitor.

18. The method of claim 1, further comprising the step of:
measuring, with said pulse oximeter, as a function of time at least one of:
    a pressure waveform;
    a photoplethysmogram;
    a percent oxygen saturation; and
    a heart rate.

\* \* \* \* \*